US009067938B2

(12) United States Patent
Schiemann et al.

(10) Patent No.: US 9,067,938 B2
(45) Date of Patent: Jun. 30, 2015

(54) PYRAZOLOPYRIDINONE DERIVATIVES AS LPA RECEPTOR ANTAGONISTS

(71) Applicant: Merck Patent GmbH, Darmstadt (DE)

(72) Inventors: Kai Schiemann, Seeheim-Jugenheim (DE); Wolfgang Staehle, Sr., Ingelheim (DE); Dirk Wienke, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 14/452,729

(22) Filed: Aug. 6, 2014

(65) Prior Publication Data
US 2014/0350046 A1 Nov. 27, 2014

Related U.S. Application Data

(62) Division of application No. 13/820,304, filed as application No. PCT/EP2011/003949 on Aug. 5, 2011, now Pat. No. 8,859,775.

(30) Foreign Application Priority Data

Sep. 2, 2010 (EP) .................................... 10009117

(51) Int. Cl.
C07D 471/02 (2006.01)
C07D 471/04 (2006.01)
A61K 45/00 (2006.01)
A61K 31/437 (2006.01)
C07D 487/04 (2006.01)

(52) U.S. Cl.
CPC .............. *C07D 471/04* (2013.01); *A61K 45/00* (2013.01); *A61K 31/437* (2013.01); *C07D 487/04* (2013.01)

(58) Field of Classification Search
CPC ..................................................... C07D 471/04
USPC ....................................................... 546/119
See application file for complete search history.

(56) References Cited

U.S. PATENT DOCUMENTS

| 6,605,617 B2 | 8/2003 | Renhowe et al. |
| 6,762,194 B2 | 7/2004 | Renhowe et al. |
| 7,071,337 B2 | 7/2006 | Kath et al. |
| 2004/0067908 A1 | 4/2004 | Nakade et al. |
| 2004/0167192 A1 | 8/2004 | Solow-Cordero et al. |
| 2008/0090783 A1 | 4/2008 | Miller et al. |
| 2008/0318901 A1 | 12/2008 | Lynch et al. |
| 2009/0029949 A1 | 1/2009 | Parrill-Baker et al. |
| 2010/0152257 A1 | 6/2010 | Hutchinson et al. |

FOREIGN PATENT DOCUMENTS

| WO | 03/062392 | 7/2003 |
| WO | 03/097615 | 11/2003 |
| WO | 2007/139946 | 12/2007 |
| WO | 2009/135590 | 11/2009 |

OTHER PUBLICATIONS

Freshney (Culture of Animal Cells, A Manual of Basic Technique, Alan R. Liss, Inc., 1983, New York, p4).*
Tsujiuchi et al. (J Toxicol Pathol 2011; 24: 143-148).*
Chen et al. Int. J. Cancer: 131, 789-802 (2012).*
International Search Report for PCT/EP2011/003949 (Oct. 17, 2011).
Third Party Observations filed on Jan. 6, 2014, by anonymous party to the EPO in the parallel EP Application No. 11741410.2. Forwarded by the EPO on Jan. 17, 2014 and received on Jan. 20, 2014. (3 pages).
Communication pursuant to Rule 114(2) EPC. Forwarded by the EPO on Jan. 17, 2014 and received on Jan. 20, 2014. (2 pages).
English Translation of the Opposition Brief filed against corresponding Ecuadorian patent application No. SP 2013-12408. (Apr. 2014) (7 pages).
Balicki, Roman "Studies in the field of Nitrogen Heterocyclic compounds, Parx XI. Abnormal Cyclocondensation of Ethyl 4,4,4-Trifluoroacetoacetate with Aminopyrazoles" Polish Journal of Chemistry, 56, 1273 (1982). (9 pages).
Patent Abstract EC 2003SP4548A. Publication Date: May 26, 2003. EC Application No. EC2003SP4548A. Filing Date: Apr. 8, 2003. Assignee: Chiron Corp. Language: Spanish. (Thomson Innovation).
Patent Abstract EC 2005SP5633A. Publication Date: Apr. 18, 2005. EC Application No. EC2005SP5633A. Filing Date: Feb. 28, 2005. Assignee: Pfizer Prod Inc. Language: Spanish. (Thomson Innovation).
Patent Abstract EC 2000SP3793A. Publication Date: Jun. 22, 2001. EC Application No. EC2000SP3793A. Filing Date: Nov. 30, 2000. Inventor: Joseph Peter Lyssikatos et al. Language: English. (Thomson Innovation).
English Translation of the third Ecuadorian Application No. EC SP2013-12408 cited in the Opposition of another another U.S. Application.
Letter dated Mar. 19, 2014, from the law firm Finnegan, Henderson, Farabow, Garrett & Dunner, LLP containing the Third Party Arguments discussed in the Jun. 9, 2014 Amendment.
Sonoda H, Aoki J, Hiramatsu T, Ishida M, Bandoh K et al.: 'A novel phosphatidic acid-selective phospholipase A1 that produces lysophosphatidic acid' J. Biol. Chem. vol. 277, 2002, pp. 34254-34263.
Janssens R, Boeynaems JM, Godart M, Communi D.: 'Cloning of a human heptahelical receptor closely related to the P2Y5 receptor' Biochem. Biophys. Res. Commun. vol. 236, 1997, pp. 106-112.
O'Dowd BF, Nguyen T, Jung BP, Marchese A, Cheng R et al.: 'Cloning and chromosomal mapping of four putative novel human G-protein-coupled receptor genes' Gene vol. 187, 1997, pp. 75-81.
Noguchi K, Ishii S, Shimizu T.: 'Identification of p2y9/GPR23 as a novel G protein-coupled receptor for lysophosphatidic acid, structurally distant from the Edg family' J. Biol. Chem. vol. 278, 2003, pp. 25600-25606.

(Continued)

*Primary Examiner* — Nizal Chandrakumar
(74) *Attorney, Agent, or Firm* — Millen, White, Zelano, Branigan, P.C.

(57) ABSTRACT

The present invention relates to novel pyrazolopyridinone derivatives according to formula (I) and a process of manufacturing thereof. These pyrazolopyridinone derivatives can be used as LPA receptor antagonists for the treatment of various herein disclosed diseases.

17 Claims, No Drawings

(56) References Cited

OTHER PUBLICATIONS

Lee CW, Rivera R, Dubin AE, Chun J.:'LPA(4)/GPR23 is a lysophosphatidic acid (LPA) receptor utilizing G(s)-, G(q)/G(i)-mediated calcium signaling and G(12/13)-mediated Rho activation' J. Biol. Chem. vol. 282, 2007, pp. 4310-4317.

Yanagida K, Ishii S, Hamano F, Noguchi K, Shimizu T.: 'LPA4/p2y9/GPR23 mediates rho-dependent morphological changes in a rat neuronal cell line' J. Biol. Chem. vol. 282, 2007, pp. 5814-5824.

Kotarsky K, Boketoft A, Bristulf J, Nilsson NE, Norberg A et al.: 'Lysophosphatidic acid binds to and activates GPR92, a G protein-coupled receptor highly expressed in gastrointestinal lymphocytes' J. Pharmacol. Exp. Ther. vol. 318, 2006, pp. 619-628.

Lee CW, Rivera R, Gardell S, Dubin AE, Chun J.: 'GPR92 as a new G12/13- and Gq-coupled lysophosphatidic acid receptor that increases cAMP, LPA5' J. Biol. Chem. vol. 281, 2006, pp. 23589-23597.

Oh Dy, Yoon JM, Moon MJ, Hwang JI, Choe H et al.: 'Identification of farnesyl pyrophosphate and N-arachidonylglycine as endogenous ligands for GPR92' J. Biol. Chem. vol. 283, 2008, pp. 21054-21064 • Williams J.

Williams Jr, Khandoga AL, Goyal P, Fells JI, Perygin DH et al.: 'Unique ligand selectivity of the GPR92/LPA5 lysophosphatidate receptor indicates role in human platelet activation' J. Biol. Chem. vol. 284, 2009, pp. 17304-17319.

Yin H, Chu A, Li W, Wang B, Shelton F et al.: 'Lipid G protein-coupled receptor ligand identification using (beta)-arrestin Path-HunterTM assay' J. Biol. Chem. vol. 284, 2009, pp. 12328-12338.

Murakami M, Shiraishi A, Tabata K, Fujita N.: 'Identification of the orphan GPCR, P2Y(10) receptor as the sphingosine-1-phosphate and lysophosphatidic acid receptor' Biochem. Biophys. Res. Commun. vol. 371, 2008, pp. 707-712.

Pasternack SM, Von Kugelgen I, Aboud KA, Lee YA, Ruschendorf F et al.: 'G protein-coupled receptor P2Y5 and its ligand LPA are involved in maintenance of human hair growth' Nat. Genet. vol. 40, 2008, pp. 329-334.

Shimomura Y, Wajid M, Ishii Y, Shapiro L, Petukhova L et al.: 'Disruption of P2RY5, an orphan G protein-coupled receptor, underlies autosomal recessive woolly hair' Nat. Genet. vol. 40, 2008, pp. 335-339.

Tabata K, Baba K, Shiraishi A, Ito M, Fujita N.: 'The orphan GPCR GPR87 was deorphanized and shown to be a lysophosphatidic acid receptor' Biochem. Biophys. Res. Commun vol. 363, 2007, pp. 861-866.

Yanagida K, Masago K, Nakanishi H, Kihara Y, Hamano F et al.: 'Identification and characterization of a novel lysophosphatidic acid receptor, p2y5/LPA6' J. Biol. Chem. vol. 284, 2009, pp. 17731-17741.

Jungbluth AA, Corrections, PNAS Feb. 18, 2003, vol.100, No. 4, 2163.

R. Ian Freshney: 'Culture of Animal Cells'; A Manual of Basic Technique; Alan R. Liss, Inc., New York, 1983.

Ruey-Jien Chen et al., 'Lysophosphatidic acid receptor 2/3-mediated IL-8-dependent antiogenesis in cervical cancer cells', Int. J. Cancer, vol. 131, pp. 789-802, 2012.

Toshifumi Tsujiuchi et al., 'Genetic and Epigenetic Alterations of Lysophosphatidic Acid Receptor Genes in Rodent Tumors by Experimental Models', J. Toxicol Pathol., vol. 24, pp. 143-148, 2011.

Hecht JH, Weiner JA, Post SR, Chun J.: 'Ventricular zone gene-1 (vzg-1) encodes a lysophosphatidic acid receptor expressed in neurogenic regions of the developing cerebral cortex' J. Cell. Biol. vol. 135, 1996, pp. 1071-1083.

Choi JW, Lee CW, Chun J.: 'Biological roles of lysophospholipid receptors revealed by genetic null mice: an update' Biochim. Biophys. Acta vol. 1781, 2008, pp. 531-539.

Lee Z, Cheng CT, Zhang H, Subler MA, Wu J et al: 'Role of LPA4/p2y9/GPR23 in negative regulation of cell motility' Mol. Biol. Cell vol. 19, 2008, pp. 5435-5445.

Lee M, Van Brocklyn J, Thangada S, Liu C, Hand A et al.: 'Sphingosine-1-phosphate as a ligand for the G protein-coupled receptor EDG-1' Science vol. 279, 1998, pp. 1552-1555.

Spiegel S, Milstien S: 'Sphingosine-1-phosphate: an enigmatic signalling Lipid' Nat. Rev.Mol. Cell.Biol. vol. 4, 2003, pp. 397-407.

Chun J, Rosen H.: 'Lysophospholipid receptors as potential drug targets in tissue transplantation and autoimmune diseases' Curr. Pharm. Des. vol. 12, 2006, pp. 161-171.

Aoki J: 'Mechanisms of lysophosphatidic acid production' Semin. Cell. Dev. Biol. vol. 15, 2004, pp. 477-489.

Sugiura T, Nakane S, Kishimoto S, Waku K, Yoshioka Y et al.: 'Occurrence of lysophosphatidic acid and its alkyl ether-linked analog in rat brain and comparison of their biological activities toward cultured neural cells' Biochim. Biophys. ACTA vol. 1440, 1999, pp. 194-204.

Sano T, Baker D, Virag T, Wada A, Yatomi Y et al.: 'Multiple mechanisms linked to platelet activation result in lysophosphatidic acid and sphingosine 1-phosphate generation in blood' J. Biol. Chem. vol. 277, 2002, pp. 21197-21206.

Umezu-Goto M, Kishi Y, Taira A, Hama K, Dohmae N et al.: 'Autotaxin has lysophospholipase D activity leading to tumor cell growth and motility by lysophosphatidic acid production' J. Cell. Biol. vol. 158, 2002, pp. 227-233.

Tokumura A, Majima E, Kariya Y, Tominaga K, Kogure K et al.: 'Identification of human plasma lysophospholipase D, a lysophosphatidic acid-producing enzyme, as autotaxin, a multifunctional phosphodiesterase' J. Biol. Chem. vol. 277, 2002, pp. 39436-39442.

Stracke ML, Krutzsch HC, Unsworth EJ, Arestad A, Cioce V et al.: 'Identification, purification, and partial sequence analysis of autotaxin, a novel motility-stimulating protein' J. Biol. Chem. vol. 267, 1992, pp. 2524-2529.

Murata J, Lee HY, Clair T, Krutzsch HC, Arestad AA et al.: 'cDNA cloning of the human tumor motility-stimulating protein, autotaxin, reveals a homology with phosphodiesterases' J. Biol. Chem. vol. 269, 1994, pp. 30479-30484.

Van Meeteren LA, Ruurs P, Stortelers C, Bouwman P, Van Rooijen MA et al.: 'Autotaxin, a secreted lysophospholipase D, is essential for blood vessel formation during development' Mol. Cell. Biol. vol. 26, 2006, pp. 5015-5022.

Tanaka M, Okudaira S, Kishi Y, Ohkawa R, Iseki S et al.: 'Autotaxin stabilizes blood vessels and is required for embryonic vasculature by producing lysophosphatidic acid.' J. Biol. Chem. vol. 281, 2006, pp. 25822-25830.

Fukushima N, Ishii I, Contos JJ, Weiner JA, Chun J.: 'Lysophospholipid receptors' Annu. Rev. Pharmacol Toxicol. vol. 41, 2001, pp. 507-534.

Ishii I, Fukushima N, Ye X, Chun J.: 'Lysophospholipid receptors: signaling and biology' Annu. Rev. Biochem. vol. 73, 2004, pp. 321-354.

Chun J: 'How the lysophospholipid got its receptor' Scientist vol. 21, 2007, pp. 48-54.

Contos JJ, Chun J.: 'Complete cDNA sequence, genomic structure, and chromosomal localization of the LPA receptor gene, IpA1/vzg-1/Gpcr26' Genomics vol. 51, 1998, pp. 364-378.

Contos JJ, Ishii I, Chun J.: 'Lysophosphatidic acid receptors' Mol. Pharmacol. vol. 58, 2000, pp. 1188-1196.

Ye X.: 'Lysophospholipid signaling in the function and pathology of the reproductive system' Hum. Reprod. Update vol. 14, 2008, pp. 519-536.

An S, Bleu T, Hallmark OG, Goetzl EJ.: 'Characterization of a novel subtype of human G-protein-coupled receptor for lysophosphatidic acid' J. Biol. Chem. vol. 273, 1998, pp. 7906-7910.

Ohuchi H, Hamada A, Matsuda H, Takagi A, Tanaka M et al.: 'Expression patterns of the lysophospholipid receptor genes during mouse early development' Dev. Dyn. vol. 237, 2008, pp. 3280-3294.

Weiner JA, Hecht JH, Chun J: 'Lysophosphatidic acid receptor gene vzg-1/IpA1/edg-2 is expressed by mature oligodendrocytes during myelination in the postnatal murine brain' J. Comp. Neurol. vol. 398, 1998, pp. 587-598.

Weiner JA, Chun J: 'Schwann cell survival mediated by the signaling phospholipid lysophosphatidic acid' Proc. Natl. Acad. Sci. USA vol. 96, 1999, pp. 5233-5238.

(56) References Cited

OTHER PUBLICATIONS

Fukushima N, Kimura Y, Chun J.: 'A single receptor encoded by vzg-1/lpA1/edg-2 couples to G proteins and mediates multiple cellular responses to lysophosphatidic acid' Proc. Natl. Acad. Sci. USA vol. 95, 1998, pp. 6151-6156.

Ishii I, Contos JJ, Fukushima N, Chun J.: 'Functional comparisons of the lysophosphatidic acid receptors, LP (A1)/VZG-1/EDG-2, LP(A2)/EDG-4, and LP(A3)/EDG-7 in neuronal cell lines using a retrovirus expression system' Mol. Pharmacol. vol. 58, 2000, pp. 895-902.

Contos JJ, Fukushima N, Weiner JA, Kaushal D, Chun J.: 'Requirement for the lpA1 lysophosphatidic acid receptor gene in normal suckling behavior' Proc. Natl. Acad. Sci. USA vol. 97, 2000, pp. 13384-13389.

Weiner JA, Fukushima N, Contos JJ, Scherer SS, Chun J.: 'Regulation of Schwann cell morphology and adhesion by receptor-mediated lysophosphatidic acid signaling' J. Neurosci. vol. 21, 2001, pp. 7069-7078.

Contos JJ, Ishii I, Fukushima N, Kingsbury MA, YE X et al.: 'Characterization of lpa(2) (Edg4) and lpa(1)/lpa(2) (Edg2/Edg4) lysophosphatidic acid receptor knockout mice: signaling deficits without obvious phenotypic abnormality attributable to lpa(2' Mol. Cell. Biol. vol. 22, 2002, pp. 6921-6929.

Estivill-Torrus G, LLebrez-Zayas P, Matas-Rico E, Santin L, Pedraza C et al.: 'Absence of LPA1 signaling results in defective cortical development' Cereb. Cortex vol. 18, 2008, pp. 938-950.

Ontos JJ, Chun J.: 'Genomic characterization of the lysophosphatidic acid receptor gene, lp(A2)/Edg4, and identification of a frameshift mutation in a previously characterized cDNA' Genomics vol. 64, 2000, pp. 155-169.

Bandoh K, Aoki J, Taira A, Tsujimoto M, Arai H et al.: 'Lysophosphatidic acid (LPA) receptors of the EDG family are differentially activated by LPA species. Structure-activity relationship of cloned LPA receptors' FEBS Lett vol. 478, 2000, pp. 159-165.

Goetzl EJ, Kong Y, Mei B.: 'Lysophosphatidic acid and sphingosine 1-phosphate protection of T cells from apoptosis in association with suppression of Bax' J. Immunol. vol. 162, 1999, pp. 2049-2056.

Deng W, Balazs L, Wang DA, Van Middlesworth L, Tigyi G et al.: 'Lysophosphatidic acid protects and rescues intestinal epithelial cells from radiation-and chemotherapy-induced apoptosis' Gastroenterology vol. 123, 2002, pp. 206-216.

Zheng Y, Kong Y, Goetzl EJ.: 'Lysophosphatidic acid receptor-selective effects on Jurkat T cell migration through a Matrigel model basement membrane' J. Immunol. vol. 166, 2001, pp. 2317-2322.

Zheng Y, Voice JK, Kong Y, Goetzl EJ.: 'Altered expression and functional profile of lysophosphatidic acid receptors in mitogen-activated human blood T lymphocytes' FASEB J. vol. 14, 2000, pp. 2387-2389.

Panchatcharam M, Miriyala S, Yang F, Rojas M, End C et al.: 'Lysophosphatidic acid receptors 1 and 2 play roles in regulation of vascular injury responses but not blood pressure' Circ. Res. vol. 103, 2008, pp. 662-670.

Yun CC, Sun H, Wang D, Rusovici R, Castleberry A et al.: 'LPA2 receptor mediates mitogenic signals in human colon cancer cells' Am. J. Physiol. Cell. Physiol. vol. 289, 2005, pp. C2-C11.

Yu S, Murph MM, Lu Y, Liu S, Hall HS et al.: 'Lysophosphatidic acid receptors determine tumorigenicity and aggressiveness of ovarian cancer cells' J. Natl. Cancer Inst. vol. 100, 2008, pp. 1630-1642.

Chen M, Towers LN, O'Connor KL: 'LPA2 (EDG4) mediates Rho-dependent chemotaxis with lower efficacy than LPA1 (EDG2) in breast carcinoma cells' Am. J. Physiol. Cell. Physiol. vol. 292, 2007, pp. C1927-C1933.

Lai YJ, Chen CS, Lin WC, Lin FT.: 'c-Src-mediated phosphorylation of TRIP6 regulates its function in lysophosphatidic acid-induced cell migration' Mol. Cell. Biol. vol. 25, 2005, pp. 5859-5868.

Lai YJ, Lin WC, Lin FT.: 'PTPL1/FAP-1 negatively regulates TRIP6 function in lysophosphatidic acid-induced cell migration' J. Biol. Chem. vol. 282, 2007, pp. 24381-24387.

Lin FT, Lai YJ.: 'Regulation of the LPA2 receptor signaling through the carboxyl-terminal tailmediated protein-protein interactions' Biochim. Biophys. Acta vol. 1781, 2008, pp. 558-562.

Komachi M, Tomura H, Malchinkhuu E, Tobo M, Mogi C et al.:'LPA1 receptors mediate stimulation, whereas LPA2 receptors mediate inhibition, of migration of pancreatic cancer cells in response to lysophosphatidic acid and malignant ascites' Carcinogenesis vol. 30, 2009, pp. 457-465.

Kingsbury MA, Rehen SK, Contos JJ, Higgins CM, Chun J.: 'Nonproliferative effects of lysophosphatidic acid enhance cortical growth and folding' Nat. Neurosci. vol. 6, 2003, pp. 1292-1299.

Bandoh K, Aoki J, Hosono H, Kobayashi S, Kobayashi T et al.: 'Molecular cloning and characterization of a novel human G-protein-coupled receptor, EDG7, for lysophosphatidic acid' J. Biol. Chem. vol. 274, 1999, pp. 27776-27785.

Im DS, Heise CE, Harding MA, George SR, O'Dowd BF et al.: 'Molecular cloning and characterization of a lysophosphatidic acid receptor, Edg-7, expressed in prostate' Mol. Pharmacol. vol. 57, 2000, pp. 753-759.

Ye X, Hama K, Contos JJ, Anliker B, Inoue A et al.: 'LPA3-mediated lysophosphatidic acid signalling in embryo implantation and spacing' Nature vol. 435, 2005, pp. 104-108.

Hama K, Aoki J, Bandoh K, Inoue A, Endo T et al.: 'Lysophosphatidic receptor, LPA3, is positively and negatively regulated by progesterone and estrogen in the mouse uterus' Life Sci. vol. 79, 2006, pp. 1736-1740.

* cited by examiner

PYRAZOLOPYRIDINONE DERIVATIVES AS LPA RECEPTOR ANTAGONISTS

TECHNICAL FIELD

The present invention relates to novel pyrazolopyridinone derivatives that act as LPA receptor antagonists and a process of manufacturing thereof.

PRIOR ART

Lysophosphatidic acid (LPA) is a small glycerophospholipid (molecular weight: 430-480 Da) that is present in all eukaryotic tissues at low concentrations, relative to major phospholipid species, and at higher concentrations (sub-micromolar range) in blood plasma. In 1996, the first high-affinity, cognate cell surface receptor for LPA was identified (LPA1) (1). This quickly led to the identification of two additional, closely related receptors (LPA2 and LPA3) and the recent identification of two more, somewhat divergent, receptors (LPA4 and LPA5). All five receptors are type I, rhodopsin-like G protein-coupled receptors (GPCRs) that differ in their tissue distribution and downstream signaling pathways (see Choi J W et al., Annu. Rev. Pharmacol. Toxicol. 2010, 50: 157-186).

Because of this heterogeneity of receptor subtypes, expression patterns, and effector pathways, the effects of LPA are diverse and widespread, regulating many biological processes. A great deal of information regarding these biological roles was derived from genetic deletion studies. To date, knockout mice have been reported for four of the five known receptors (LPA1-4), as well as the major LPA-generating enzyme, autotaxin (ATX) (2, 3). These mutant mice, in addition to emerging classes of chemical tools, have transitioned observations made through the use of in vitro studies into medically relevant contexts. It is difficult to discuss LPA without some mention of the structurally similar lipid sphingosine 1-phosphate (S1P). S1P was also discovered to be an extracellular signaling lipid when its first cognate receptor (S1P1) was deorphanized in 1998 (4). Although they represent distinct signaling systems, similarities between these two lipids extend to their tissue distribution and concentration, homology and effector pathways of their cognate receptors, and the broad range of their biological roles. However, because LPA and S1P signaling have become such a robust research area in recent years, this review focuses specifically on biological roles of LPA. Comprehensive reviews of S1P signaling can be found elsewhere (5, 6).

Since the early twentieth century, lysophospholipids have been known to have biological activity, but these effects were long thought to be the result of nonspecific detergent-like disruptions of the plasma membrane. These studies, however, were performed at very high, nonphysiological concentrations. It is now known that the effects of LPA at physiological concentrations are mediated by five bona fide, high-affinity cognate receptors (LPA1-LPA5) and perhaps by additional recently proposed or as yet unidentified receptors (16-18).

LPA1 is the first high-affinity receptor identified for LPA (1) (reviewed in 16, 17). The mammalian LPAR1 gene (human chromosomal locus 9q31.3) encodes an approximately 41-kDa protein consisting of 364 amino acids with 7 putative transmembrane domains. In mice, the open reading frame is encoded on two of five exons with a conserved intron (shared with Lpar2 and Lpar3) that interrupts transmembrane domain 6. One reported variant of Lpar1 (mrec1.3), which may be produced by alternative exon usage or splicing, results in an 18-amino-acid deletion of the N terminus (19). The biological significance of this variant has not been established.

Wide expression of Lpar1 is observed in adult mice, with clear presence in at least brain, uterus, testis, lung, small intestine, heart, stomach, kidney, spleen, thymus, placenta, and skeletal muscle (20, 21). LPAR1 is also widely expressed in humans (22). Expression of Lpar1 is more spatially restricted during embryonic development but is enriched in the brain (23). In particular, the developing nervous system is a major locus for Lpar1 expression, where it is spatially and temporally regulated (reviewed in 17, 20). During embryogenesis, central nervous system (CNS) expression is restricted to the neocortical neurogenic region called the ventricular zone (VZ) and superficially in a layer that includes the meninges (1). The VZ disappears at the end of cortical neurogenesis, just prior to birth, but Lpar1 expression continues in the postnatal brain, where it is apparent in cells present within developing white matter tracts and coincides with myelination (24). In situ hybridization reveals Lpar1 expression in oligodendrocytes and Schwann cells, the myelinating cells of the CNS and peripheral nervous system, respectively (24, 25).

LPA1 couples with and activates three types of Gproteins: G$\alpha$i/o, G$\alpha$q/11, and G$\alpha$12/13 (26, 27). LPA1 activation induces a range of cellular responses: cell proliferation and survival, cell migration, and cytoskeletal changes; altered cell-cell contact through serum-response element activation, Ca2+ mobilization, and adenylyl cyclase inhibition; and activation of mitogen-activated protein kinase, phospholipase C, Akt, and Rho pathways (reviewed in 16, 17, 20).

The targeted disruption of Lpar1 in mice revealed unanticipated in vivo functions of this receptor (28). Lpar1−/− mice show 50% perinatal lethality in a mixed (C57Bl/6J× 129) genetic background and further decreased survival in pure (C57Bl/6J or Balb/cByJ) genetic backgrounds (J. Chun, unpublished observations). Survivors have a reduced body size, craniofacial dysmorphism with blunted snouts, and increased apoptosis in sciatic nerve Schwann cells (28, 29). Defective suckling, attributed to olfactory defects, likely accounts for perinatal lethality. Small fractions of Lpar1−/− embryos have exencephaly (~5%) or frontal cephalic hemorrhage (~2.5%). Loss of LPA response in embryonic neuroblasts and fibroblasts demonstrates nonredundant functions and roles for Lpar1 in vivo (28, 30). In addition, during colony expansion of the original line (28), an Lpar1−/− substrain arose spontaneously, which was called the "Málaga variant" and exhibits more severe developmental brain defects (31).

Lpar2 was identified from GenBank searches of orphan GPCR genes because of its ~60% amino acid similarity to Lpar1. In humans, LPAR2 (chromosomal locus 19p12) encodes a protein that has a predicted amino acid sequence of 348 residues, yielding a calculated molecular mass of ~39 kDa (32).

The expression pattern of Lpar2 is relatively restricted spatiotemporally compared to that of Lpar1 (20, 22). In mouse, Lpar2 is highly expressed in kidney, uterus, and testis and moderately expressed in lung; and lower levels of expression are found in stomach, spleen, thymus, brain, and heart (20). Lpar2 is also expressed in embryonic brain but decreases within a week after birth (20). In human tissues, high expression of LPAR2 is detected in testis and leukocytes, with moderate expression found in prostate, spleen, thymus, and pancreas (22). In cancer cells, aberrant expression of LPAR2 has been reported in several cases, suggesting a tumor promoting role for LPA2.

LPA2 couples to the G$\alpha$i/o, G$\alpha$11/q, and G$\alpha$12/13 family of heterotrimeric G proteins. These G proteins convey signals through downstream molecules that include Ras, mitogen activated protein kinase, phosphatidylinositol 3-kinase, Rac, phospholipase C, diacylglycerol, and Rho, which is similar to LPA1 (28). LPA2 is a bona fide high affinity cognate LPA receptor (33). Activation of LPA2 signaling is generally associated with such processes as cell survival (34, 35) and cell migration (36-38). As a consequence, LPA2 signaling has emerged as a potential factor for cancer metastasis (see below) (39-41).

Interestingly, several reports have provided evidence for the interaction of LPA2 signaling with other pathways. For example, LPA2 promotes cell migration through interactions with focal adhesion molecule TRIP6 (42, 43), and several PDZ proteins and zinc finger proteins are also reported to interact directly with the carboxyl-terminal tail of LPA2 (44). In addition, LPA2-mediated signaling can provide inhibitory effects on the epidermal growth factor-induced migration and invasion of pancreatic cancer cells through the Gα12/13/Rho pathway (45). These studies provide evidence that LPA2 signaling has cross-regulation between classical G protein signaling cascades and other signaling pathways to regulate the efficiency and specificity of signal transduction.

Mouse knockout studies demonstrate that Lpar2−/− mutant animals are viable, grossly normal, and born at normal Mendelian ratios without sexual bias, but Lpar1−/−/Lpar2−/− mutants have an exacerbation of the frontal hematomas present in the Lpar1−/− mutant (28, 30). In addition, primary fibroblasts and embryonic cortical cells from the double-null mutants show vastly reduced responses to exogenous LPA (30, 46).

Lpar3 was discovered as an orphan GPCR gene using degenerate PCR-based cloning and homology searches (47, 48). LPAR3 (human chromosomal locus 1p22.3-p31.1) encodes a ~40-kDa GPCR that is ~50% identical to mouse LPA1 and LPA2 in amino acid sequence. Expression of LPAR3 has been observed in human heart, testis, prostate, pancreas, lung, ovary, and brain (47, 48) and is most abundant in mouse testis, kidney, lung, small intestine, heart, stomach, spleen, brain, and thymus (20). Interestingly, it has been shown that, in the murine uterus, Lpar3 mRNA is exclusively expressed in the luminal endometrial epithelium at the window of implantation (49) and that its expression is regulated by progesterone and estrogen (50).

Like LPA1 and LPA2, LPA3 can couple with Gαi/o and Gαq to mediate LPA-induced phospholipase C activation, Ca2+ mobilization, adenylyl cyclase inhibition and activation, and mitogen activated protein kinase activation (27). However, LPA3 is unable to couple with Gα12/13 and therefore does not mediate cell rounding in neuronal cells in which Gα12/13 and Rho are involved (27). Also, LPA3 is not as responsive as LPA1 and LPA2 to LPA species with saturated acyl chains but has a relatively high affinity for 2-acyl-LPA containing unsaturated fatty acids (47, 51).

Lpar3−/− mice are viable and grossly normal, but female nulls show a striking phenotype in the reproductive system (49) (see below). However, despite the fact that LPA3 is expressed in the frontal cortex, hippocampus, and amygdala (47, 48), no phenotypes related to LPA3 loss in the nervous system have been reported to date.

LPA4 was originally identified as a putative GPCR from an analysis of the expressed sequence tag database (52, 53) and was found to be a specific receptor for LPA through ligand screening (54). LPA4 is structurally distinct from classical LPA and S1P receptors that share significant homology and is more closely related to P2Y purinergic receptors. It does not, however, respond to any nucleotides or nucleosides tested (52, 54). In humans, the LPAR4 gene is located on chromosome X, region q13-q21.1, and contains an intronless open reading frame of 1113 base pairs encoding 370 amino acids with a calculated molecular mass of ~42 kDa (52, 53). LPA4 has a specific binding affinity to 18:1-LPA with a Kd value of 44.8 nM but not to other lysophospholipids and related lipids such as S1P and SPC (54). LPA4 prefers structural analogs of LPA with a rank order of 18:1->18:0->16:0->14:0->1-alkyl->1-alkenyl-LPA (54).

Among 16 human tissues examined with quantitative real-time PCR, LPAR4 mRNA is ubiquitously expressed and specifically abundant in the ovary (54). Among mouse tissues examined with Northern blot and real-time PCR, Lpar4 mRNA is expressed in heart, skin, thymus, ovary, developing brain, and embryonic fibroblasts (3, 55). Whole mount in situ hybridization detected Lpar4 mRNA in limb buds, somites, facial processes, and developing brain (23).

In LPA4-overexpressing cells, LPA induces morphological changes such as cell rounding and stress fiber formation through the Gα12/13 and Rho/Rho-kinase pathways (55, 56), as observed in LPA1-, LPA2-, and LPA5-expressing cells. Additionally, Rho-kinase-mediated cell aggregation and N-cadherin-dependent cell adhesion are observed in LPA4-expressing cells (56). LPA induces intracellular cAMP accumulation through Gαs, and Ca2+ mobilization through Gαq/11 and Gαi (55, 56). Notably, Gαs-coupling is not reported for classical LPA receptors. Recently, LPA4-deficient mice have been reported, although they display no apparent abnormalities (3). However, LPA4 has a suppressive effect on cell motility in that (a) LPA4 deficiency enhances migratory response to LPA in fibroblasts and (b) heterologous expression of LPA4 suppresses LPA1-dependent migration of B103 cells and LPA-induced migration and invasion of colon cancer cells (3).

Recently, an orphan GPCR (GPR92) was identified as an LPA receptor and was renamed LPA5 to reflect this identity (57, 58). Human LPAR5 is located on chromosome 12p13.31 and encodes a ~41 kDa protein consisting of 372 amino acids. Like other LPA receptors (LPA1-4), LPA5 also belongs to the rhodopsin-GPCR family and, although structurally different from LPA1-3, it shares 35% homology with LPA4 (58). Lpar5 is broadly expressed in murine tissues such as embryonic brain, small intestine, skin, spleen, stomach, thymus, lung, heart, liver, and embryonic stem cells (57, 58).

LPA induces neurite retraction and stress fiber formation in LPA5-expressing cells by coupling to Gα12/13 and increases intracellular calcium levels by activation of Gαq (58). Furthermore, LPA increases cAMP levels and inositol phosphate production in LPA5-expressing cells (57, 58). Recently, two other lipid-derived molecules (farnesyl pyrophosphate and N-arachidonylglycin) were characterized as LPA5 ligands (59). In this study, farnesyl-pyrophosphate activated Gαq/11- and Gαs-mediated signaling, whereas N-arachidonylglycin was able to activate only Gαq/11-mediated signaling. It has been suggested that those ligands interact differently with the ligand-binding pocket of LPA5 (59). However, subsequent studies confirm that LPA5 is a bona fide LPA receptor that can also be activated by farnesyl pyrophosphate at much higher concentrations relative to 18:1-LPA, leaving open the question of the biological relevance of these alternative ligands (60, 61).

Recently, three more orphan GPCRs have been published as new, putative LPA receptors: GPR87, P2Y5, and P2Y10 (62-64). Each of these orphan GPCRs belongs to the purinergic receptor P2Y family and is more closely related to LPA4 and LPA5 than to LPA1-3. Of these, P2Y5 is likely to join the LPA receptor family as LPA6, based on recent published and unpublished data. P2Y5 was identified as a critical mediator for human hair growth and is a causal gene of a rare familial form of human hair loss (63, 63a), and recent studies of this putative LPA6 support activation of this receptor by uncharacteristically high concentrations of LPA [EC50 in the low micromolar range for some assays (65)]. This suggests an identity of P2Y5 as a relatively low-affinity LPA receptor, distinct from LPA1-5 (65), perhaps requiring a distinct ligand or other explanations. GPR87 and P2Y10 were reported to increase intracellular Ca2+ mobilization using a promiscuous Gα16 fusion system (62, 64). P2Y10-Gα16 also can induce Ca2+ transients by S1P as well as LPA (EC50=53 and 130 nM, respectively) (62). More detailed investigations are required to confirm these three candidates as bona fide LPA receptors. Non-GPCR LPA receptors have been reported, but their validity remains to be established (66).

CITED LITERATURE

1. Hecht J H, Weiner J A, Post S R, Chun J. 1996. Ventricular zone gene-1 (vzg-1) encodes a lysophosphatidic acid receptor expressed in neurogenic regions of the developing cerebral cortex. *J. Cell. Biol.* 135:1071-83
2. Choi J W, Lee C W, Chun J. 2008. Biological roles of lysophospholipid receptors revealed by genetic null mice: an update. *Biochim. Biophys. Acta* 1781:531-39
3. Lee Z, Cheng C T, Zhang H, Subler M A, Wu J, et al. 2008. Role of LPA4/p2y9/GPR23 in negative regulation of cell motility. *Mol. Biol. Cell.* 19:5435-45
4. Lee M, Van Brocklyn J, Thangada S, Liu C, Hand A, et al. 1998. Sphingosine-1-phosphate as a ligand for the G protein-coupled receptor EDG-1. *Science* 279:1552-55
5. Spiegel S, Milstien S. 2003. Sphingosine-1-phosphate: an enigmatic signalling Lipid. *Nat. Rev. Mol. Cell. Biol.* 4:397-407
6. Chun J, Rosen H. 2006. Lysophospholipid receptors as potential drug targets in tissue transplantation and autoimmune diseases. *Curr. Pharm. Des.* 12:161-71
7. Aoki J. 2004. Mechanisms of lysophosphatidic acid production. *Semin. Cell. Dev. Biol.* 15:477-89
8. Sugiura T, Nakane S, Kishimoto S, Waku K, Yoshioka Y, et al. 1999. Occurrence of lysophosphatidic acid and its alkyl ether-linked analog in rat brain and comparison of their biological activities toward cultured neural cells. *Biochim. Biophys. Acta* 1440:194-204
9. Sano T, Baker D, Virag T, Wada A, Yatomi Y, et al. 2002. Multiple mechanisms linked to platelet activation result in lysophosphatidic acid and sphingosine 1-phosphate generation in blood. *J. Biol. Chem.* 277:21197-206
10. Umezu-Goto M, Kishi Y, Taira A, Hama K, Dohmae N, et al. 2002. Autotaxin has lysophospholipase D activity leading to tumor cell growth and motility by lysophosphatidic acid production. *J. Cell. Biol.* 158:227-33
11. Tokumura A, Majima E, Kariya Y, Tominaga K, Kogure K, et al. 2002. Identification of human plasma lysophospholipase D, a lysophosphatidic acid-producing enzyme, as autotaxin, a multifunctional phosphodiesterase. *J. Biol. Chem.* 277:39436-42
12. Stracke M L, Krutzsch H C, Unsworth E J, Arestad A, Cioce V, et al. 1992. Identification, purification, and partial sequence analysis of autotaxin, a novel motility-stimulating protein. *J. Biol. Chem.* 267:2524-29
13. Murata J, Lee H Y, Clair T, Krutzsch H C, Arestad A A, et al. 1994. cDNA cloning of the human tumor motility-stimulating protein, autotaxin, reveals a homology with phosphodiesterases. *J. Biol. Chem.* 269:30479-84
14. van Meeteren L A, Ruurs P, Stortelers C, Bouwman P, van Rooijen M A, et al. 2006. Autotaxin, a secreted lysophospholipase D, is essential for blood vessel formation during development. *Mol. Cell. Biol.* 26:5015-22
15. Tanaka M, Okudaira S, Kishi Y, Ohkawa R, Iseki S, et al. 2006. Autotaxin stabilizes blood vessels and is required for embryonic vasculature by producing lysophosphatidic acid. *J. Biol. Chem.* 281:25822-30
16. Fukushima N, Ishii I, Contos J J, Weiner J A, Chun J. 2001. Lysophospholipid receptors. *Annu. Rev. Pharmacol. Toxicol.* 41:507-34
17. Ishii I, Fukushima N, Ye X, Chun J. 2004. Lysophospholipid receptors: signaling and biology. *Annu. Rev. Biochem.* 73:321-54
18. Chun J. 2007. How the lysophospholipid got its receptor. *Scientist* 21:48-54
19. Contos J J, Chun J. 1998. Complete cDNA sequence, genomic structure, and chromosomal localization of the LPA receptor gene, lpA1/vzg-1/Gpcr26. *Genomics* 51:364-78
20. Contos J J, Ishii I, Chun J. 2000. Lysophosphatidic acid receptors. *Mol. Pharmacol.* 58:1188-96
21. Ye X. 2008. Lysophospholipid signaling in the function and pathology of the reproductive system. *Hum. Reprod. Update* 14:519-36
22. An S, Bleu T, Hallmark O G, Goetzl E J. 1998. Characterization of a novel subtype of human G-protein-coupled receptor for lysophosphatidic acid. *J. Biol. Chem.* 273:7906-10
23. Ohuchi H, Hamada A, Matsuda H, Takagi A, Tanaka M, et al. 2008. Expression patterns of the lysophospholipid receptor genes during mouse early development. *Dev. Dyn.* 237:3280-94
24. Weiner J A, Hecht J H, Chun J. 1998. Lysophosphatidic acid receptor gene vzg-1/lpA1/edg-2 is expressed by mature oligodendrocytes during myelination in the postnatal murine brain. *J. Comp. Neurol.* 398:587-98
25. Weiner J A, Chun J. 1999. Schwann cell survival mediated by the signaling phospholipid lysophosphatidic acid. *Proc. Natl. Acad. Sci. USA* 96:5233-38
26. Fukushima N, Kimura Y, Chun J. 1998. A single receptor encoded by vzg-1/lpA1/edg-2 couples to G proteins and mediates multiple cellular responses to lysophosphatidic acid. *Proc. Natl. Acad. Sci. USA* 95:6151-56
27. Ishii I, Contos J J, Fukushima N, Chun J. 2000. Functional comparisons of the lysophosphatidic acid receptors, LP(A1)/VZG-1/EDG-2, LP(A2)/EDG-4, and LP(A3)/EDG-7 in neuronal cell lines using a retrovirus expression system. *Mol. Pharmacol.* 58:895-902
28. Contos J J, Fukushima N, Weiner J A, Kaushal D, Chun J. 2000. Requirement for the lpA1 lysophosphatidic acid receptor gene in normal suckling behavior. *Proc. Natl. Acad. Sci. USA* 97:13384-89
29. Weiner J A, Fukushima N, Contos J J, Scherer S S, Chun J. 2001. Regulation of Schwann cell morphology and adhesion by receptor-mediated lysophosphatidic acid signaling. *J. Neurosci.* 21:7069-78
30. Contos J J, Ishii I, Fukushima N, Kingsbury M A, Ye X, et al. 2002. Characterization of lpa(2) (Edg4) and lpa(1)/lpa(2) (Edg2/Edg4) lysophosphatidic acid receptor knockout mice: signaling deficits without obvious phenotypic abnormality attributable to lpa(2). *Mol. Cell. Biol.* 22:6921-29
31. Estivill-Torrus G, Llebrez-Zayas P, Matas-Rico E, Santin L, Pedraza C, et al. 2008. Absence of LPA1 signaling results in defective cortical development. *Cereb. Cortex* 18:938-50
32. Contos J J, Chun J. 2000. Genomic characterization of the lysophosphatidic acid receptor gene, lp(A2)/Edg4, and identification of a frameshift mutation in a previously characterized cDNA. *Genomics* 64:155-69
33. Bandoh K, Aoki J, Taira A, Tsujimoto M, Arai H, et al. 2000. Lysophosphatidic acid (LPA) receptors of the EDG family are differentially activated by LPA species. Structure-activity relationship of cloned LPA receptors. *FEBS Lett.* 478:159-65
34. Goetzl E J, Kong Y, Mei B. 1999. Lysophosphatidic acid and sphingosine 1-phosphate protection of T cells from apoptosis in association with suppression of Bax. *J. Immunol.* 162:2049-56
35. Deng W, Balazs L, Wang D A, Van Middlesworth L, Tigyi G, et al. 2002. Lysophosphatidic acid protects and rescues intestinal epithelial cells from radiation- and chemotherapy-induced apoptosis. *Gastroenterology* 123:206-16
36. Zheng Y, Kong Y, Goetzl E J. 2001. Lysophosphatidic acid receptor-selective effects on Jurkat T cell migration through a Matrigel model basement membrane. *J. Immunol.* 166:2317-22
37. Zheng Y, Voice J K, Kong Y, Goetzl E J. 2000. Altered expression and functional profile of lysophosphatidic acid receptors in mitogen-activated human blood T lymphocytes. *FASEB J.* 14:2387-89
38. Panchatcharam M, Miriyala S, Yang F, Rojas M, End C, et al. 2008. Lysophosphatidic acid receptors 1 and 2 play roles in regulation of vascular injury responses but not blood pressure. *Circ. Res.* 103:662-70
39. Yun C C, Sun H, Wang D, Rusovici R, Castleberry A, et al. 2005. LPA2 receptor mediates mitogenic signals in human colon cancer cells. *Am. J. Physiol. Cell. Physiol.* 289:C2-11
40. Yu S, Murph M M, Lu Y, Liu S, Hall H S, et al. 2008. Lysophosphatidic acid receptors determine tumorigenicity and aggressiveness of ovarian cancer cells. *J. Natl. Cancer Inst.* 100:1630-42
41. Chen M, Towers L N, O'Connor K L. 2007. LPA2 (EDG4) mediates Rho-dependent chemotaxis with lower efficacy than LPA1 (EDG2) in breast carcinoma cells. *Am. J. Physiol. Cell. Physiol.* 292:01927-33
42. Lai Y J, Chen C S, Lin W C, Lin F T. 2005. c-Src-mediated phosphorylation of TRIP6 regulates its function in lysophosphatidic acid-induced cell migration. *Mol. Cell. Biol.* 25:5859-68
43. Lai Y J, Lin W C, Lin F T. 2007. PTPL1/FAP-1 negatively regulates TRIP6 function in lysophosphatidic acid-induced cell migration. *J. Biol. Chem.* 282:24381-87
44. Lin F T, Lai Y J. 2008. Regulation of the LPA2 receptor signaling through the carboxyl-terminal tail mediated protein-protein interactions. *Biochim. Biophys. Acta* 1781:558-62
45. Komachi M, Tomura H, Malchinkhuu E, Tobo M, Mogi C, et al. 2009. LPA1 receptors mediate stimulation, whereas LPA2 receptors mediate inhibition, of migration of pancreatic cancer cells in response to lysophosphatidic acid and malignant ascites. *Carcinogenesis* 30:457-65
46. Kingsbury M A, Rehen S K, Contos J J, Higgins C M, Chun J. 2003. Non-proliferative effects of lysophosphatidic acid enhance cortical growth and folding. *Nat. Neurosci.* 6:1292-99
47. Bandoh K, Aoki J, Hosono H, Kobayashi S, Kobayashi T, et al. 1999. Molecular cloning and characterization of a novel human G-protein-coupled receptor, EDG7, for lysophosphatidic acid. *J. Biol. Chem.* 274:27776-85
48. Im D S, Heise C E, Harding M A, George S R, O'Dowd B F, et al. 2000. Molecular cloning and characterization of a lysophosphatidic acid receptor, Edg-7, expressed in prostate. *Mol. Pharmacol.* 57:753-59
49. Ye X, Hama K, Contos J J, Anliker B, Inoue A, et al. 2005. LPA3-mediated lysophosphatidic acid signalling in embryo implantation and spacing. *Nature* 435:104-8
50. Hama K, Aoki J, Bandoh K, Inoue A, Endo T, et al. 2006. Lysophosphatidic receptor, LPA3, is positively and negatively regulated by progesterone and estrogen in the mouse uterus. *Life Sci.* 79:1736-40
51. Sonoda H, Aoki J, Hiramatsu T, Ishida M, Bandoh K, et al. 2002. A novel phosphatidic acid-selective phospholipase A1 that produces lysophosphatidic acid. *J. Biol. Chem.* 277:34254-63
52. Janssens R, Boeynaems J M, Godart M, Communi D. 1997. Cloning of a human heptahelical receptor closely related to the P2Y5 receptor. *Biochem. Biophys. Res. Commun.* 236:106-12
53. O'Dowd B F, Nguyen T, Jung B P, Marchese A, Cheng R, et al. 1997. Cloning and chromosomal mapping of four putative novel human G-protein-coupled receptor genes. *Gene* 187:75-81
54. Noguchi K, Ishii S, Shimizu T. 2003. Identification of p2y9/GPR23 as a novel G protein-coupled receptor for lysophosphatidic acid, structurally distant from the Edg family. *J. Biol. Chem.* 278:25600-6
55. Lee C W, Rivera R, Dubin A E, Chun J. 2007. LPA(4)/GPR23 is a lysophosphatidic acid (LPA) receptor utilizing G(s)-, G(q)/G(i)-mediated calcium signaling and G(12/13)-mediated Rho activation. *J. Biol. Chem.* 282:4310-17
56. Yanagida K, Ishii S, Hamano F, Noguchi K, Shimizu T. 2007. LPA4/p2y9/GPR23 mediates rho-dependent morphological changes in a rat neuronal cell line. *J. Biol. Chem.* 282:5814-24
57. Kotarsky K, Boketoft A, Bristulf J, Nilsson N E, Norberg A, et al. 2006. Lysophosphatidic acid binds to and activates GPR92, a G protein-coupled receptor highly expressed in gastrointestinal lymphocytes. *J. Pharmacol. Exp. Ther.* 318:619-28
58. Lee C W, Rivera R, Gardell S, Dubin A E, Chun J. 2006. GPR92 as a new G12/13- and Gq-coupled lysophosphatidic acid receptor that increases cAMP, LPA5. *J. Biol. Chem.* 281:23589-97
59. Oh D Y, Yoon J M, Moon M J, Hwang J I, Choe H, et al. 2008. Identification of farnesyl pyrophosphate and N-arachidonylglycine as endogenous ligands for GPR92. *J. Biol. Chem.* 283:21054-64
60. Williams J R, Khandoga A L, Goyal P, Fells J I, Perygin D H, et al. 2009. Unique ligand selectivity of the GPR92/LPA5 lysophosphatidate receptor indicates role in human platelet activation. *J. Biol. Chem.* 284:17304-19
61. Yin H, Chu A, Li W, Wang B, Shelton F, et al. 2009. Lipid G protein-coupled receptor ligand identification using {beta}-arrestin PathHunter™ assay. *J. Biol. Chem.* 284:12328-38
62. Murakami M, Shiraishi A, Tabata K, Fujita N. 2008. Identification of the orphan GPCR, P2Y(10) receptor as the sphingosine-1-phosphate and lysophosphatidic acid receptor. *Biochem. Biophys. Res. Commun.* 371:707-12
63. Pasternack S M, von Kugelgen I, Aboud K A, Lee Y A, Ruschendorf F, et al. 2008. G protein-coupled receptor P2Y5 and its ligand LPA are involved in maintenance of human hair growth. *Nat. Genet.* 40:329-34
63a. Shimomura Y, Wajid M, Ishii Y, Shapiro L, Petukhova L, et al. 2008. Disruption of P2RY5, an orphan G protein-coupled receptor, underlies autosomal recessive woolly hair. *Nat. Genet.* 40:335-39

64. Tabata K, Baba K, Shiraishi A, Ito M, Fujita N. 2007. The orphan GPCR GPR87 was deorphanized and shown to be a lysophosphatidic acid receptor. *Biochem. Biophys. Res. Commun.* 363:861-66

65. Yanagida K, Masago K, Nakanishi H, Kihara Y, Hamano F, et al. 2009. Identification and characterization of a novel lysophosphatidic acid receptor, p2y5/LPA6. *J. Biol. Chem.* 284:17731-41

66. McIntyre T M, Pontsler A V, Silva A R, St Hilaire A, Xu Y, et al. 2003. Identification of an intracellular receptor for lysophosphatidic acid (LPA): LPA is a transcellular PPAR-gamma agonist. *Proc. Natl. Acad. Sci. USA* 100:131-36

Further prior art is as follows:

Balicki R (Polish Journal of Chemistry 1983, 57: 789-797) relates to the abnormal cyclocondensation of ethyl-4,4,4-trifluoroacetoacetate with aminopyrazoles. The scientific paper discloses compound 2 of the present invention (page 792, scheme 4, compound 14). The article, however, does not disclose the application of the therein disclosed compounds as medicaments.

WO 2003/062392 discloses methods of treating conditions associated with an EDG receptor. The compounds disclosed structurally differ from the compounds of the present invention.

WO 2009/135590 describes acylamino-substituted fused cyclopentanecarboxylic acid derivatives and their use as pharmaceuticals. The compounds disclosed structurally differ from the compounds of the present invention.

The citation of any reference in this application is not an admission that the reference is relevant prior art to this application.

DESCRIPTION OF THE INVENTION

The present invention has the object to provide novel LPA receptor antagonists.

The object of the present invention has surprisingly been solved in one aspect by providing compounds of formula (I)

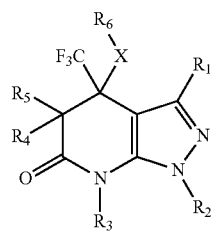

(I)

wherein:
$R_1$ denotes aryl, heteroaryl, cycloalkyl, heterocyclyl, arylalkyl, heteroarylalkyl, cycloalkylalkyl or heterocyclylalkyl, which can optionally be substituted with one or more substituents selected from alkyl, cycloalkyl, cycloalkylalkyl, heterocyclyl, heterocyclylalkyl, aryl, arylalkyl, heteroaryl, heteroarylalkyl, halogen, —F, —Cl, —Br, —I, —CN, —CF$_3$, —N$_3$, —NH$_2$, —NHZ1, —NZ2Z3, —NO$_2$, —OH, —OCF$_3$, —SH, —O—SO$_3$H, —OP(O)(OH)$_2$, —CHO, —COOH, —C(O)NH$_2$, —SO$_3$H, —P(O)(OH)$_2$, —C(O)—Z4, —C(O)O—Z5, —C(O)NH—Z6, —C(O)NZ7Z8, —O—Z9, —O(—Z10-O)$_a$—H (a=1, 2, 3, 4, 5), —O(—Z11-O)$_b$—Z12 (b=1, 2, 3, 4, 5), —OC(O)—Z13, —OC(O)—O—Z14, —OC(O)—NHZ15, —O—C(O)—NZ16Z17, —OP(O)(OZ18)(OZ19), —OSi(Z20)(Z21)(Z22), —OS(O$_2$)—Z23, —NHC(O)—NH$_2$, —NHC(O)—Z24, —NZ25C(O)—Z26, —NH—C(O)—O—Z27, —NH—C(O)—NH—Z28, —NH—C(O)—NZ29Z30, —NZ31-C(O)—O—Z32, —NZ33-C(O)—NH—Z34, —NZ35-C(O)—NZ36Z37, —NHS(O$_2$)—Z38, —NZ39S(O$_2$)—Z40, —S—Z41, —S(O)—Z42, —S(O$_2$)—Z43, —S(O$_2$)NH—Z44, —S(O$_2$)NZ45Z46, —S(O$_2$)O—Z47, —P(O)(OZ48)(OZ49), —Si(Z50)(Z51)(Z52), —C(NH)—NH$_2$, —C(NZ53)-NH$_2$, —C(NH)—NHZ54, —C(NH)—NZ55Z56, —C(NZ57)-NHZ58, —C(NZ59)-NZ60Z61, —NH—C(O)—NH—O—Z62, —NH—C(O)—NZ63-O—Z64, —NZ65-C(O)—NZ66-O—Z67, —N(—C(O)—NH—O—Z68)$_2$, —N(—C(O)—NZ69-O—Z70)$_2$, —N(—C(O)—NH—O—Z71)(-C(O)—NZ72-O—Z73), —C(S)—Z74, —C(S)—O—Z75, —C(S)—NH—Z76, —C(S)—NZ77Z78, —C(O)—NH—O—Z79, —C(O)—NZ80-O—Z81, —C(S)—NH—O—Z82, —C(S)—NZ83-O—Z84, —C(O)—NH—NH—Z85, —C(O)—NH—NZ86Z87, —C(O)—NZ88-NZ89Z90, —C(S)—NH—NH—Z91, —C(S)—NH—NZ92Z93, —C(S)—NZ94-NZ95Z96, —C(O)—C(O)—O—Z97, —C(O)—C(O)—NH$_2$, —C(O)—C(O)—NHZ98, —C(O)—C(O)—NZ99Z100, —C(S)—C(O)—O—Z101, —C(O)—C(S)—O—Z102, —C(S)—C(S)—O—Z103, —C(S)—C(O)—NH$_2$, —C(S)—C(O)—NHZ104, —C(S)—C(O)—NZ105Z106, —C(S)—C(S)—NH$_2$, —C(S)—C(S)—NHZ107, —C(S)—C(S)—NZ108Z109, —C(O)—C(S)—NH$_2$, —C(O)—C(S)—NHZ110, —C(O)—C(S)—NZ111Z112";

wherein Z1, Z2, Z3, Z4, Z5, Z6, Z7, Z8, Z9, Z10, Z11, Z12, Z13, Z14, Z15, Z16, Z17, Z18, Z19, Z20, Z21, Z22, Z23, Z24, Z25, Z26, Z27, Z28, Z29, Z30, Z31, Z32, Z33, Z34, Z35, Z36, Z37, Z38, Z39, Z40, Z41, Z42, Z43, Z44, Z45, Z46, Z47, Z48, Z49, Z50, Z51, Z52, Z53, Z54, Z55, Z56, Z57, Z58, Z59, Z60, Z61, Z62, Z63, Z64, Z65, Z66, Z67, Z68, Z69, Z70, Z71, Z72, Z73, Z74, Z75, Z76, Z77, Z78, Z79, Z80, Z81, Z82, Z83, Z84, Z85, Z86, Z87, Z88, Z89, Z90, Z91, Z92, Z93, Z94, Z95, Z96, Z97, Z98, Z99, Z100, Z101, Z102, Z103, Z104, Z105, Z106, Z107, Z108, Z109, Z110, Z111, Z112 are independently from each other selected from the group consisting of: "alkyl, cycloalkyl, cycloalkylalkyl, heterocyclyl, heterocyclylalkyl, aryl, arylalkyl, heteroaryl, heteroarylalkyl" and wherein alternatively Z7, Z8 and/or Z16, Z17 and/or Z29, Z30 and/or Z36, Z37 and/or Z45, Z46 and/or Z55, Z56 and/or Z60, Z61 and/or Z77, Z78 and/or Z86, Z87 and/or Z89, Z90 and/or Z92, Z93 and/or Z95, Z96 and/or Z99, Z100 and/or Z105, Z106 and/or Z108, Z109 and/or Z111, Z112 respectively together can also form, "heterocyclyl";

$R_2$ denotes H or alkyl,
$R_3$ denotes H or alkyl,
$R_4$, $R_5$ independently from each other denote H, alkyl, OH-alkyl, alkoxy, halogen, F, Cl, Br, I, CN, NHR, NH$_2$, NR$_2$, S-alkyl or NH-alkyl-OH, wherein R independently from each other denotes alkyl, aryl, heteroaryl, cycloalkyl or heterocyclyl; or
$R_4$ and $R_5$ together form cycloalkyl or heterocyclyl,
$R_6$ denotes H or alkyl,
X denotes O, NH or N-alky,
with the proviso that the following compound is excluded from formula (I):

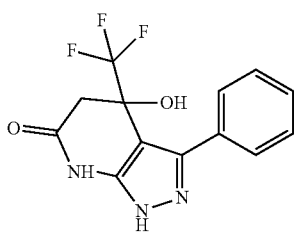 [SMILES: O=C1CC(O)(C(F)(F)F)c2c(-c3ccccc3)n[nH]c2N1]

and the physiologically acceptable salts, solvates, tautomers and stereoisomers thereof, including mixtures thereof in all ratios.

In a preferred embodiment, a compound according to formula (I) is provided, wherein:
$R_1$ denotes aryl, heteroaryl, cycloalkyl or arylalkyl, preferably phenyl, thiophenyl, furanyl, pyrazolyl, pyridinyl, indolyl or benzyl, which can optionally be substituted with one or more substituents selected from halogen, F, Cl, Br, I, $CF_3$, alkyl, methyl, alkoxy or methoxy, and the physiologically acceptable salts, solvates, tautomers and stereoisomers thereof, including mixtures thereof in all ratios.

In a preferred embodiment, a compound according to formula (I) and above embodiment is provided, wherein:
$R_2$ denotes H, methyl or ethyl, and the physiologically acceptable salts, solvates, tautomers and stereoisomers thereof, including mixtures thereof in all ratios.

In a preferred embodiment, a compound according to formula (I) and above embodiments is provided, wherein:
$R_3$ denotes H, methyl or ethyl, and the physiologically acceptable salts, solvates, tautomers and stereoisomers thereof, including mixtures thereof in all ratios.

In a preferred embodiment, a compound according to formula (I) and above embodiments is provided, wherein:
$R_4$, $R_5$ independently from each other denote H, alkyl, OH-alkyl, alkoxy, methyl, ethyl, hydroxy-ethyl or methoxy, and the physiologically acceptable salts, solvates, tautomers and stereoisomers thereof, including mixtures thereof in all ratios.

In a preferred embodiment, a compound according to formula (I) and above embodiments is provided, wherein:
$R_6$ denotes H, and the physiologically acceptable salts, solvates, tautomers and stereoisomers thereof, including mixtures thereof in all ratios.

In a preferred embodiment, a compound according to formula (I) and above embodiments is provided, wherein:
X denotes O, and the physiologically acceptable salts, solvates, tautomers and stereoisomers thereof, including mixtures thereof in all ratios.

In a preferred embodiment, a compound according to formula (I) and above embodiments is provided, wherein:
$R_1$ denotes aryl, heteroaryl, cycloalkyl or arylalkyl, preferably phenyl, thiophenyl, furanyl, pyrazolyl, pyridinyl, indolyl or benzyl, which can optionally be substituted with one or more substituents selected from halogen, F, Cl, Br, I, $CF_3$, alkyl, methyl, alkoxy or methoxy,
$R_2$ denotes H, methyl or ethyl,
$R_3$ denotes H, methyl or ethyl,
$R_4$, $R_5$ independently from each other denote H, alkyl, OH-alkyl, alkoxy, methyl, ethyl, hydroxy-ethyl or methoxy,
$R_6$ denotes H,
X denotes O, and the physiologically acceptable salts, solvates, tautomers and stereoisomers thereof, including mixtures thereof in all ratios.

In another aspect, the object of the present invention has surprisingly been solved by providing a compound selected from the group consisting of:

| | | |
|---|---|---|
| 1 | 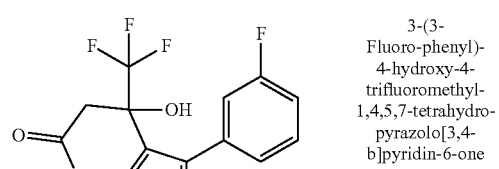 | 3-(3-Fluoro-phenyl)-4-hydroxy-4-trifluoromethyl-1,4,5,7-tetrahydro-pyrazolo[3,4-b]pyridin-6-one |
| 2 | 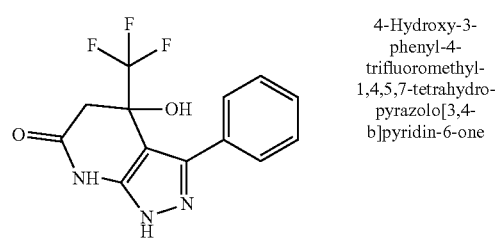 | 4-Hydroxy-3-phenyl-4-trifluoromethyl-1,4,5,7-tetrahydro-pyrazolo[3,4-b]pyridin-6-one |
| 3 | 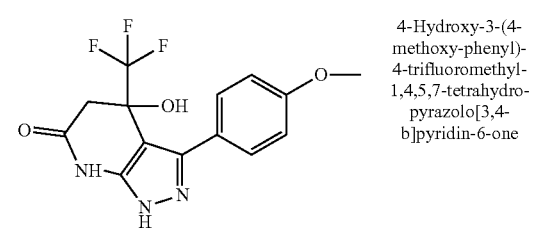 | 4-Hydroxy-3-(4-methoxy-phenyl)-4-trifluoromethyl-1,4,5,7-tetrahydro-pyrazolo[3,4-b]pyridin-6-one |
| 4 | 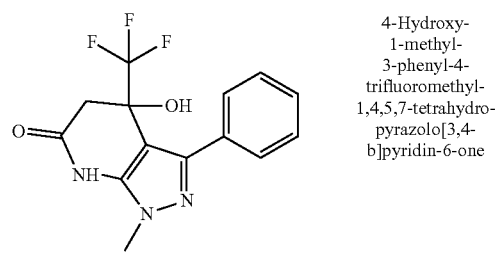 | 4-Hydroxy-1-methyl-3-phenyl-4-trifluoromethyl-1,4,5,7-tetrahydro-pyrazolo[3,4-b]pyridin-6-one |
| 5 | 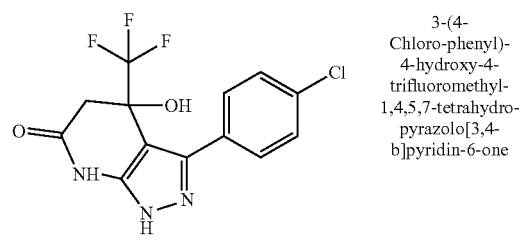 | 3-(4-Chloro-phenyl)-4-hydroxy-4-trifluoromethyl-1,4,5,7-tetrahydro-pyrazolo[3,4-b]pyridin-6-one |

| # | | Name |
|---|---|---|
| 6 | 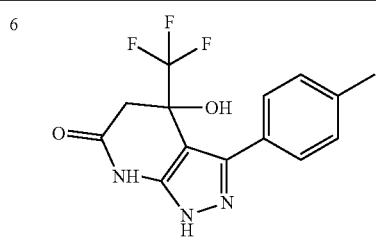 | 4-Hydroxy-3-p-tolyl-4-trifluoromethyl-1,4,5,7-tetrahydro-pyrazolo[3,4-b]pyridin-6-one |
| 7 | 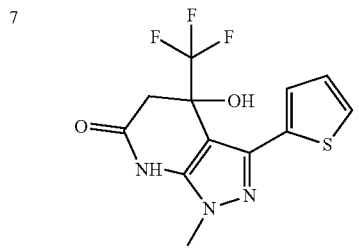 | 4-Hydroxy-1-methyl-3-thiophen-2-yl-4-trifluoromethyl-1,4,5,7-tetrahydro-pyrazolo[3,4-b]pyridin-6-one |
| 8 | 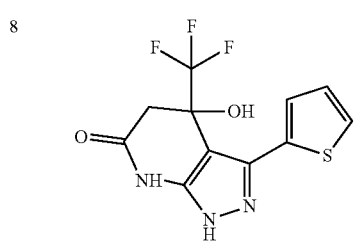 | 4-Hydroxy-3-thiophen-2-yl-4-trifluoromethyl-1,4,5,7-tetrahydro-pyrazolo[3,4-b]pyridin-6-one |
| 9 | 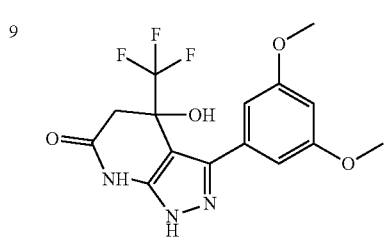 | 3-(3,5-Dimethoxy-phenyl)-4-hydroxy-4-trifluoromethyl-1,4,5,7-tetrahydro-pyrazolo[3,4-b]pyridin-6-one |
| 10 | 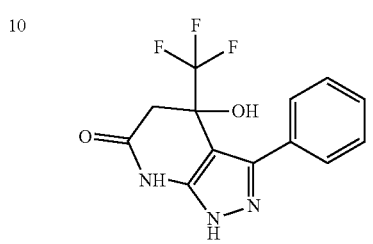 | (−)-4-Hydroxy-3-phenyl-4-trifluoromethyl-1,4,5,7-tetrahydro-pyrazolo[3,4-b]pyridin-6-one |
| 11 | 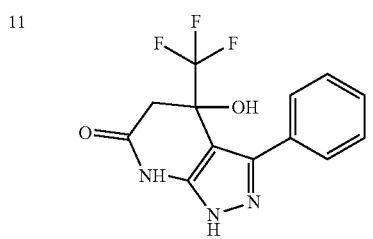 | (+)-4-Hydroxy-3-phenyl-4-trifluoromethyl-1,4,5,7-tetrahydro-pyrazolo[3,4-b]pyridin-6-one |
| 12 | 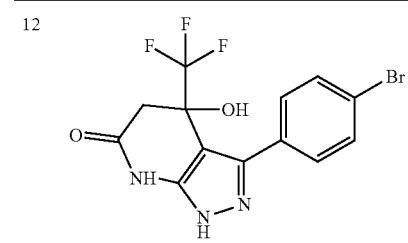 | 3-(4-Bromo-phenyl)-4-hydroxy-4-trifluoromethyl-1,4,5,7-tetrahydro-pyrazolo[3,4-b]pyridin-6-one |
| 13 | 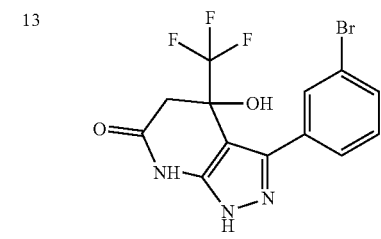 | 3-(3-Bromo-phenyl)-4-hydroxy-4-trifluoromethyl-1,4,5,7-tetrahydro-pyrazolo[3,4-b]pyridin-6-one |
| 14 | 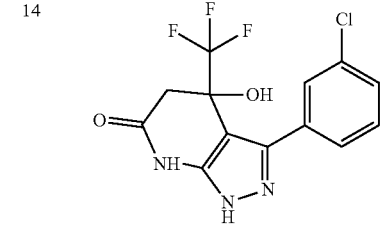 | 3-(3-Chloro-phenyl)-4-hydroxy-4-trifluoromethyl-1,4,5,7-tetrahydro-pyrazolo[3,4-b]pyridin-6-one |
| 15 | 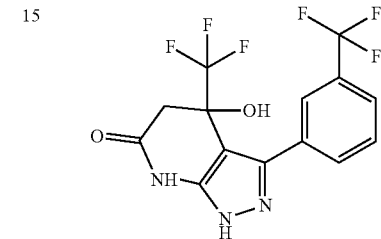 | 4-Hydroxy-4-trifluoromethyl-3-(3-trifluoromethyl-phenyl)-1,4,5,7-tetrahydro-pyrazolo[3,4-b]pyridin-6-one |
| 16 | 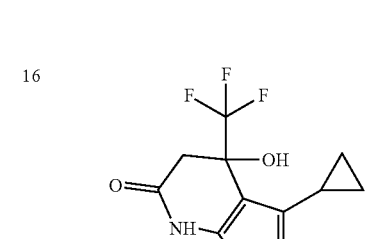 | 3-Cyclopropyl-4-hydroxy-4-trifluoromethyl-1,4,5,7-tetrahydro-pyrazolo[3,4-b]pyridin-6-one |
| 17 | 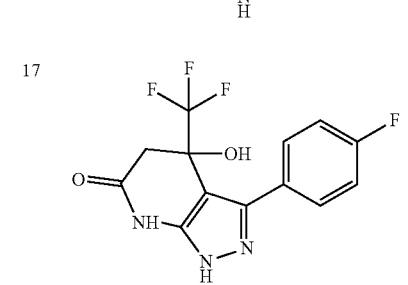 | 3-(4-Fluoro-phenyl)-4-hydroxy-4-trifluoromethyl-1,4,5,7-tetrahydro-pyrazolo[3,4-b]pyridin-6-one |

| # | Structure | Name |
|---|---|---|
| 18 | 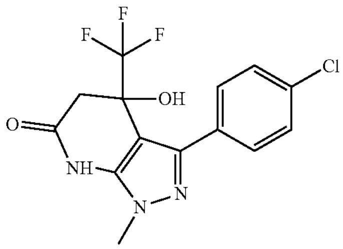 [SMILES: Cn1nc(-c2ccc(Cl)cc2)c2c1NC(=O)CC2(O)C(F)(F)F] | 3(4-Chloro-phenyl)-4-hydroxy-1-methyl-4-trifluoromethyl-1,4,5,7-tetrahydro-pyrazolo[3,4-b]pyridin-6-one |
| 19 | 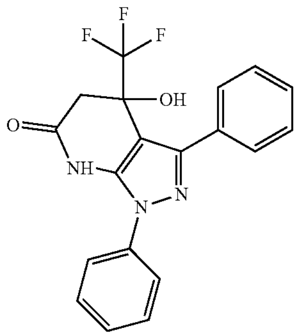 [SMILES: O=C1CC(O)(C(F)(F)F)c2c(-c3ccccc3)nn(-c3ccccc3)c2N1] | 4-Hydroxy-1,3-diphenyl-4-trifluoromethyl-1,4,5,7-tetrahydro-pyrazolo[3,4-b]pyridin-6-one |
| 20 | 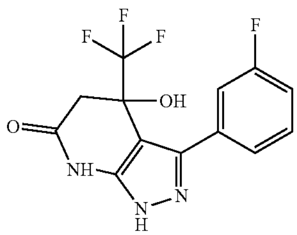 [SMILES: O=C1CC(O)(C(F)(F)F)c2c(-c3cccc(F)c3)n[nH]c2N1] | (−)-3-(3-Fluoro-phenyl)-4-hydroxy-4-trifluoromethyl-1,4,5,7-tetrahydro-pyrazolo[3,4-b]pyridin-6-one |
| 21 | 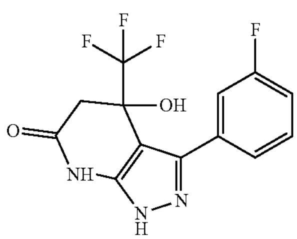 [SMILES: O=C1CC(O)(C(F)(F)F)c2c(-c3cccc(F)c3)n[nH]c2N1] | (+)-3-(3-Fluoro-phenyl)-4-hydroxy-4-trifluoromethyl-1,4,5,7-tetrahydro-pyrazolo[3,4-b]pyridin-6-one |
| 22 | 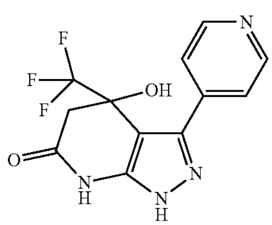 [SMILES: O=C1CC(O)(C(F)(F)F)c2c(-c3ccncc3)n[nH]c2N1] | 4-Hydroxy-3-pyridin-4-yl-4-trifluoromethyl-1,4,5,7-tetrahydro-pyrazolo[3,4-b]pyridin-6-one |
| 23 | 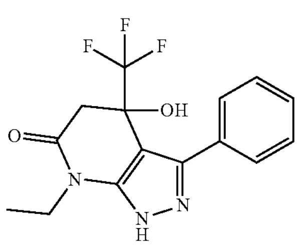 [SMILES: CCN1C(=O)CC(O)(C(F)(F)F)c2c(-c3ccccc3)n[nH]c21] | 4-Hydroxy-7-ethyl-3-phenyl-4-trifluoromethyl-1,4,5,7-tetrahydro-pyrazolo[3,4-b]pyridin-6-one |
| 24 | | 4-Hydroxy-5-methyl-3-phenyl-4-trifluoromethyl-1,4,5,7-tetrahydro-pyrazolo[3,4-b]pyridin-6-one |
| 25 | | 4-Hydroxy-5-ethyl-3-phenyl-4-trifluoromethyl-1,4,5,7-tetrahydro-pyrazolo[3,4-b]pyridin-6-one |
| 26 | | 4-Hydroxy-5-(2-hydroxy-ethyl)-3-phenyl-4-trifluoromethyl-1,4,5,7-tetrahydro-pyrazolo[3,4-b]pyridin-6-one |
| 27 | | 4-Hydroxy-5-methoxy-3-phenyl-4-trifluoromethyl-1,4,5,7-tetrahydro-pyrazolo[3,4-b]pyridin-6-one |
| 28 | | 3-Benzyl-4-hydroxy-4-trifluoromethyl-1,4,5,7-tetrahydro-pyrazolo[3,4-b]pyridin-6-one |
| 29 | | 4-Hydroxy-3-(1H-indol-3-yl)-4-trifluoromethyl-1,4,5,7-tetrahydro-pyrazolo[3,4-b]pyridin-6-one |

| | | |
|---|---|---|
| 30 | | 3-Furan-2-yl-4-hydroxy-4-trifluoromethyl-1,4,5,7-tetrahydro-pyrazolo[3,4-b]pyridin-6-one |
| 31 | | 3-(3,4-Dimethoxy-phenyl)-4-hydroxy-4-trifluoromethyl-1,4,5,7-tetrahydro-pyrazolo[3,4-b]pyridin-6-one |
| 32 | | 4-Hydroxy-3-(3-methoxy-phenyl)-4-trifluoromethyl-1,4,5,7-tetrahydro-pyrazolo[3,4-b]pyridin-6-one |
| 33 | | 3-(1,5-Dimethyl-1H-pyrazol-4-yl)-4-hydroxy-4-trifluoromethyl-1,4,5,7-tetrahydro-pyrazolo[3,4-b]pyridin-6-one |
| 34 | | 7-Ethyl-4-hydroxy-3-phenyl-4-trifluoromethyl-1,4,5,7-tetrahydro-pyrazolo[3,4-b]pyridin-6-one |
| 35 | | 4-(3,5-Bis-trifluoromethyl-phenyl)-4-hydroxy-3-phenyl-1,4,5,7-tetrahydro-pyrazolo[3,4-b]pyridin-6-one | and the physiologically acceptable salts, solvates, tautomers and stereoisomers thereof, including mixtures thereof in all ratios.

For the avoidance of doubt, if chemical name and chemical structure of the above illustrated compounds do not correspond by mistake, the chemical structure is regarded to unambiguously define the compound.

All the above generically or explicitly disclosed compounds, including preferred subsets/embodiments of the herein disclosed formula (I) and Compounds 1 to 35, are hereinafter referred to as compounds of the (present) invention.

The nomenclature as used herein for defining compounds, especially the compounds according to the invention, is in general based on the rules of the IUPAC organization for chemical compounds and especially organic compounds.

The terms indicated for explanation of the above compounds of the invention always, unless indicated otherwise in the description or in the claims, have the following meanings:

The term "unsubstituted" means that the corresponding radical, group or moiety has no substituents.

The term "substituted" means that the corresponding radical, group or moiety has one or more substituents. Where a radical has a plurality of substituents, and a selection of various substituents is specified, the substituents are selected independently of one another and do not need to be identical.

The terms "alkyl" or "A" as well as other groups having the prefix "alk" for the purposes of this invention refer to acyclic saturated or unsaturated hydrocarbon radicals which may be branched or straight-chain and preferably have 1 to 8 carbon atoms, i.e. $C_1$-$C_8$-alkanyls, $C_2$-$C_8$-alkenyls and $C_2$-$C_8$-alkynyls. Alkenyls have at least one C—C double bond and alkynyls at least one C—C triple bond. Alkynyls may additionally also have at least one C—C double bond. Examples of suitable alkyl radicals are methyl, ethyl, n-propyl, isopropyl, n-butyl, isobutyl, sec-butyl, tert-butyl, n-pentyl, iso-pentyl, neo-pentyl, tert-pentyl, 2- or 3-methyl-pentyl, n-hexyl, 2-hexyl, isohexyl, n-heptyl, n-octyl, n-nonyl, n-decyl, n-undecyl, n-dodecyl, n-tetradecyl, n-hexadecyl, n-octadecyl, n-icosanyl, n-docosanyl, ethylenyl (vinyl), propenyl (—$CH_2CH=CH_2$; —$CH=CH$—$CH_3$, —$C(=CH_2)$—$CH_3$), butenyl, pentenyl, hexenyl, heptenyl, octenyl, octadienyl, octadecenyl, octadec-9-enyl, icosenyl, icos-11-enyl, (Z)-icos-11-enyl, docosnyl, docos-13-enyl, (Z)-docos-13-enyl, ethynyl, propynyl (—$CH_2$—$C\equiv CH$, —$C\equiv C$—$CH_3$), butynyl, pentynyl, hexynyl, heptynyl, octynyl. Especially preferred is $C_{1-4}$-alkyl. A $C_{1-4}$-alkyl radical is for example a methyl, ethyl, propyl, isopropyl, butyl, isobutyl, tert-butyl.

The term "cycloalkyl" for the purposes of this invention refers to saturated and partially unsaturated non-aromatic cyclic hydrocarbon groups/radicals, having 1 to 3 rings, that contain 3 to 20, preferably 3 to 12, most preferably 3 to 8 carbon atoms. The cycloalkyl radical may also be part of a bi- or polycyclic system, where, for example, the cycloalkyl radical is fused to an aryl, heteroaryl or heterocyclyl radical as defined herein by any possible and desired ring member(s). The bonding to the compounds of the general formula can be effected via any possible ring member of the cycloalkyl radical. Examples of suitable cycloalkyl radicals are cyclopropyl, cyclobutyl, cyclopentyl, cyclohexyl, cycloheptyl, cyclooctyl, cyclodecyl, cyclohexenyl, cyclopentenyl and cyclooctadienyl. Especially preferred are $C_3$-$C_9$-cycloalkyl and $C_4$-$C_8$-cycloalkyl. A $C_4$-$C_8$-cycloalkyl radical is for example a cyclobutyl, cyclopentyl, cyclohexyl, cycloheptyl, cyclooctyl.

The term "heterocyclyl" or "heterocycle" for the purposes of this invention refers to a mono- or polycyclic system of 3 to 20, preferably 5 or 6 to 14 ring atoms comprising carbon atoms and 1, 2, 3, 4, or 5 heteroatoms, in particular nitrogen, oxygen and/or sulfur which are identical or different. The cyclic system may be saturated, mono- or polyunsaturated but may not be aromatic. In the case of a cyclic system consisting of at least two rings the rings may be fused or spiro- or otherwise connected. Such "heterocyclyl" radicals can be linked via any ring member. The term "heterocyclyl" also includes systems in which the heterocycle is part of a bi- or polycyclic saturated, partially unsaturated and/or aromatic system, such as where the heterocycle is fused to an "aryl", "cycloalkyl", "heteroaryl" or "heterocyclyl" group as defined herein via any desired and possible ring member of the heterocycyl radical. The bonding to the compounds of the general formula can be effected via any possible ring member of the heterocycyl radical. Examples of suitable "heterocyclyl" radicals are pyrrolidinyl, thiapyrrolidinyl, piperidinyl, piperazinyl, oxapiperazinyl, oxapiperidinyl, oxadiazolyl, tetrahydrofuryl, imidazolidinyl, thiazolidinyl, tetrahydropyranyl, morpholinyl, tetrahydrothiophenyl, dihydropyranyl, indolinyl, indolinylmethyl, imidazolidinyl, 2-aza-bicyclo[2.2.2]octanyl.

The term "aryl" for the purposes of this invention refers to a mono- or polycyclic aromatic hydrocarbon systems having 3 to 14, preferably 5 to 14, more preferably 5 to 10 carbon atoms. The term "aryl" also includes systems in which the aromatic cycle is part of a bi- or polycyclic saturated, partially unsaturated and/or aromatic system, such as where the aromatic cycle is fused to an "aryl", "cycloalkyl", "heteroaryl" or "heterocyclyl" group as defined herein via any desired and possible ring member of the aryl radical. The bonding to the compounds of the general formula can be effected via any possible ring member of the aryl radical. Examples of suitable "aryl" radicals are phenyl, biphenyl, naphthyl, 1-naphthyl, 2-naphthyl and anthracenyl, but likewise indanyl, indenyl, or 1,2,3,4-tetrahydronaphthyl. The most preferred aryl is phenyl.

The term "heteroaryl" for the purposes of this invention refers to a 3 to 15, preferably 5 to 14, more preferably 5-, 6- or 7-membered mono- or polycyclic aromatic hydrocarbon radical which comprises at least 1, where appropriate also 2, 3, 4 or 5 heteroatoms, preferably nitrogen, oxygen and/or sulfur, where the heteroatoms are identical or different. The number of nitrogen atoms is preferably 0, 1, 2, or 3, and that of the oxygen and sulfur atoms is independently 0 or 1. The term "heteroaryl" also includes systems in which the aromatic cycle is part of a bi- or polycyclic saturated, partially unsaturated and/or aromatic system, such as where the aromatic cycle is fused to an "aryl", "cycloalkyl", "heteroaryl" or "heterocyclyl" group as defined herein via any desired and possible ring member of the heteroaryl radical. The bonding to the compounds of the general formula can be effected via any possible ring member of the heteroaryl radical. Examples of suitable "heteroaryl" are acridinyl, benzdioxinyl, benzimidazolyl, benzisoxazolyl, benzodioxolyl, benzofuranyl, benzothiadiazolyl, benzothiazolyl, benzothienyl, benzoxazolyl, carbazolyl, cinnolinyl, dibenzofuranyl, dihydrobenzothienyl, furanyl, furazanyl, furyl, imidazolyl, indazolyl, indolinyl, indolizinyl, indolyl, isobenzylfuranyl, isoindolyl, isoquinolinyl, isoquinolyl, isothiazolyl, isoxazolyl, naphthyridinyl, oxadiazolyl, oxazolyl, phenazinyl, phenothiazinyl, phenoxazinyl, phthalazinyl, pteridinyl, purinyl, pyrazinyl, pyrazolyl, pyridazinyl, pyridinyl, pyridyl, pyrimidinyl, pyrimidyl, pyrrolyl, quinazolinyl, quinolinyl, quinolyl, quinoxalinyl, tetrazolyl, thiadiazolyl, thiazolyl, thienyl, thiophenyl, triazinyl, triazolyl.

For the purposes of the present invention, the terms "alkylcycloalkyl", "cycloalkylalkyl", "alkyl-heterocyclyl", "heterocyclylalkyl", "alkyl-aryl", "arylalkyl", "alkyl-heteroaryl" and "heteroarylalkyl" mean that alkyl, cycloalkyl, heterocycl, aryl and heteroaryl are each as defined above, and the cycloalkyl, heterocyclyl, aryl and heteroaryl radical is bonded to the compounds of the general formula via an alkyl radical, preferably $C_1$-$C_8$-alkyl radical, more preferably $C_1$-$C_4$-alkyl radical.

The term "alkyloxy" or "alkoxy" for the purposes of this invention refers to an alkyl radical according to above definition that is attached to an oxygen atom. The attachment to the compounds of the general formula is via the oxygen atom. Examples are methoxy, ethoxy and n-propyloxy, propoxy, isopropoxy. Preferred is "$C_1$-$C_4$-alkyloxy" having the indicated number of carbon atoms.

The term "cycloalkyloxy" or "cycloalkoxy" for the purposes of this invention refers to a cycloalkyl radical according to above definition that is attached to an oxygen atom. The attachment to the compounds of the general formula is via the oxygen atom. Examples are cyclopropyloxy, cyclobutyloxy, cyclopentyloxy, cyclohexyloxy, cycloheptyloxy, cyclooctyloxy. Preferred is "$C_3$-$C_9$cycloalkyloxy" having the indicated number of carbon atoms.

The term "heterocyclyloxy" for the purposes of this invention refers to a heterocyclyl radical according to above definition that is attached to an oxygen atom. The attachment to the compounds of the general formulae is via the oxygen atom. Examples are pyrrolidinyloxy, thiapyrrolidinyloxy, piperidinyloxy, piperazinyloxy.

The term "aryloxy" for the purposes of this invention refers to an aryl radical according to above definition that is attached to an oxygen atom. The attachment to the compounds of the general formula is via the oxygen atom. Examples are phenyloxy, 2-naphthyloxy, 1-naphthyloxy, biphenyloxy, indanyloxy. Preferred is phenyloxy.

The term "heteroaryloxy" for the purposes of this invention refers to a heteroaryl radical according to above definition that is attached to an oxygen atom. The attachment to the compounds of the general formula is via the oxygen atom. Examples are pyrrolyloxy, thienyloxy, furyloxy, imidazolyloxy, thiazolyloxy.

The term "carbonyl" or "carbonyl moiety" for the purposes of this invention refers to a —C(O)— group.

The term "alkylcarbonyl" for the purposes of this invention refers to a "alkyl-C(O)—" group, wherein alkyl is as defined herein.

The term "alkoxycarbonyl" or "alkyloxycarbonyl" for the purposes of this invention refers to a "alkyl-O—C(O)-" group, wherein alkyl is as defined herein.

The term "alkoxyalkyl" for the purposes of this invention refers to a "alkyl-O—alkyl-" group, wherein alkyl is as defined herein.

The term "haloalkyl" for the purposes of this invention refers to an alkyl group as defined herein comprising at least one carbon atom substituent with at least one halogen as defined herein.

The term "halogen", "halogen atom", "halogen substituent" or "Hal" for the purposes of this invention refers to one or, where appropriate, a plurality of fluorine (F, fluoro), bromine (Br, bromo), chlorine (Cl, chloro), or iodine (I, iodo) atoms. The designations "dihalogen", "trihalogen" and "perhalogen" refer respectively to two, three and four substituents, where each substituent can be selected independently from the group consisting of fluorine, chlorine, bromine and iodine. "Halogen" preferably means a fluorine, chlorine or bromine atom. Fluorine is most preferred, when the halogens are substituted on an alkyl (haloalkyl) or alkoxy group (e.g. $CF_3$ and $CF_3O$).

The term "hydroxyl" or "hydroxy" means an OH group.

The term "composition", as in pharmaceutical composition, for the purposes of this invention is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

The terms "administration of" and "administering a" compound should be understood to mean providing a compound of the invention or a prodrug of a compound of the invention to the individualist need.

As used herein, the term "effective amount" refers to any amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

All stereoisomers of the compounds of the invention are contemplated, either in a mixture or in pure or substantially pure form. The compounds of the invention can have asymmetric centers at any of the carbon atoms. Consequently, they can exist in the form of their racemates, in the form of the pure enantiomers and/or diastereomers or in the form of mixtures of these enantiomers and/or diastereomers. The mixtures may have any desired mixing ratio of the stereoisomers.

Thus, for example, the compounds of the invention which have one or more centers of chirality and which occur as racemates or as diastereomer mixtures can be fractionated by methods known per se into their optical pure isomers, i.e. enantiomers or diastereomers. The separation of the compounds of the invention can take place by column separation on chiral or nonchiral phases or by recrystallization from an optionally optically active solvent or with use of an optically active acid or base or by derivatization with an optically active reagent such as, for example, an optically active alcohol, and subsequent elimination of the radical.

The compounds of the invention may be present in the form of their double bond isomers as "pure" E or Z isomers, or in the form of mixtures of these double bond isomers.

Where possible, the compounds of the invention may be in the form of the tautomers, such as keto-enol tautomers.

It is likewise possible for the compounds of the invention to be in the form of any desired prodrugs such as, for example, esters, carbonates, carbamates, ureas, amides or phosphates, in which cases the actually biologically active form is released only through metabolism. Any compound that can be converted in vivo to provide the bioactive agent (i.e. compounds of the invention) is a prodrug within the scope and spirit of the invention.

Various forms of prodrugs are well known in the art and are described for instance in:
 (i) Wermuth C G et al., Chapter 31: 671-696, The Practice of Medicinal Chemistry, Academic Press 1996;
 (ii) Bundgaard H, Design of Prodrugs, Elsevier 1985; and
 (iii) Bundgaard H, Chapter 5: 131-191, A Textbook of Drug Design and Development, Harwood Academic Publishers 1991.
Said references are incorporated herein by reference.

It is further known that chemical substances are converted in the body into metabolites which may where appropriate likewise elicit the desired biological effect—in some circumstances even in more pronounced form.

Any biologically active compound that was converted in vivo by metabolism from any of the compounds of the invention is a metabolite within the scope and spirit of the invention.

The compounds of the invention can, if they have a sufficiently basic group such as, for example, a secondary or tertiary amine, be converted with inorganic and organic acids into salts. The pharmaceutically acceptable salts of the compounds of the invention are preferably formed with hydrochloric acid, hydrobromic acid, iodic acid, sulfuric acid, phosphoric acid, methanesulfonic acid, p-toluenesulfonic acid, carbonic acid, formic acid, acetic acid, sulfoacetic acid, trifluoroacetic acid, oxalic acid, malonic acid, maleic acid, succinic acid, tartaric acid, racemic acid, malic acid, embonic acid, mandelic acid, fumaric acid, lactic acid, citric acid, taurocholic acid, glutaric acid, stearic acid, glutamic acid or aspartic acid. The salts which are formed are, inter alia, hydrochlorides, chlorides, hydrobromides, bromides, iodides, sulfates, phosphates, methanesulfonates, tosylates, carbonates, bicarbonates, formates, acetates, sulfoacetates, triflates, oxalates, malonates, maleates, succinates, tartrates, malates, embonates, mandelates, fumarates, lactates, citrates, glutarates, stearates, aspartates and glutamates. The stoichiometry of the salts formed from the compounds of the invention may moreover be an integral or non-integral multiple of one.

The compounds of the invention can, if they contain a sufficiently acidic group such as, for example, the carboxy, sulfonic acid, phosphoric acid or a phenolic group, be converted with inorganic and organic bases into their physiologically tolerated salts. Examples of suitable inorganic bases are ammonium, sodium hydroxide, potassium hydroxide, calcium hydroxide, and of organic bases are ethanolamine, diethanolamine, triethanolamine, ethylenediamine, t-butylamine, t-octylamine, dehydroabietylamine, cyclohexylamine, dibenzylethylene-diamine and lysine. The stoichiometry of the salts formed from the compounds of the invention can moreover be an integral or non-integral multiple of one.

It is likewise possible for the compounds of the invention to be in the form of their solvates and, in particular, hydrates which can be obtained for example by crystallization from a solvent or from aqueous solution. It is moreover possible for one, two, three or any number of solvate or water molecules to combine with the compounds of the invention to give solvates and hydrates.

By the term "solvate" is meant a hydrate, an alcoholate, or other solvate of crystallization.

It is known that chemical substances form solids which exist in different order states which are referred to as polymorphic forms or modifications. The various modifications of a polymorphic substance may differ greatly in their physical properties. The compounds of the invention can exist in various polymorphic forms and certain modifications may moreover be metastable. All these polymorphic forms of the compounds are to be regarded as belonging to the invention.

The compounds of the invention are surprisingly characterized by a strong and/or selective inhibition of LPA receptors, preferably LPA receptor 1, LPA receptor 2, LPA receptor 3, LPA receptor 4, LPA receptor 5 or LPA receptor 6, most preferably LPA receptor 2.

Due to their surprisingly strong and/or selective receptor inhibition, the compounds of the invention can be advantageously administered at lower doses compared to other less potent or selective inhibitors of the prior art while still achieving equivalent or even superior desired biological effects. In addition, such a dose reduction may advantageously lead to less or even no medicinal adverse effects. Further, the high inhibition selectivity of the compounds of the invention may translate into a decrease of undesired side effects on its own regardless of the dose applied.

The compounds of the invention being LPA receptor inhibitors generally have an inhibition constant $IC_{50}$ of less than about 10 μM, and preferably less than about 1 μM.

The compounds according to the invention preferably exhibit an advantageous biological activity, which is easily demonstrated in enzyme-based assays, for example assays as described herein. In such enzyme-based assays, the compounds according to the invention preferably exhibit and cause an inhibiting effect, which is usually documented by $IC_{50}$ values in a suitable range, preferably in the micromolar range and more preferably in the nanomolar range.

As discussed herein, the LPA receptor signaling pathways are relevant for various diseases. Accordingly, the compounds according to the invention are useful in the prophylaxis and/or treatment of diseases that are dependent on the said signaling pathways by interaction with one or more of the said signaling pathways. The present invention therefore relates to compounds according to the invention as promoters or inhibitors, preferably as inhibitors, of the signaling pathways described herein, particularly the LPA receptor signaling pathways.

The object of the present invention has surprisingly been solved in another aspect by providing the use of a compound of the invention for modulating, preferably inhibiting, LPA receptor mediated biological activity, preferably LPA receptor 1, LPA receptor 2, LPA receptor 3, LPA receptor 4, LPA receptor 5 or LPA receptor 6 mediated biological activity, most preferably LPA receptor 2 mediated biological activity.

The terms "inhibiting, inhibition and/or retardation" are intended to refer for the purposes of the present invention to as follows: "partial or complete inhibiting, inhibition and/or retardation". In this case, it is within the specialist knowledge of the average person skilled in the art to measure and determine such inhibiting, inhibition, and/or retardation by means of the usual methods of measurement and determination. Thus, a partial inhibiting, inhibition and/or retardation, for example, can be measured and determined in relation to a complete inhibiting, inhibition and/or retardation.

The object of the present invention has surprisingly been solved in another aspect by providing a process for manufacturing a compound of the invention, comprising the steps of:

(a) reacting a compound of formula (II)

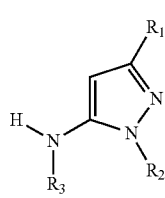

(II)

wherein $R_1$, $R_2$ and $R_3$ have the meaning as defined above, with a compound of formula (III)

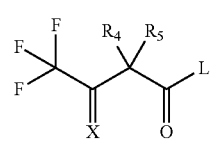

(III)

wherein $R_4$, $R_5$ and X have the meaning as defined above and L denotes a leaving group,
to yield a compound of formula (I)

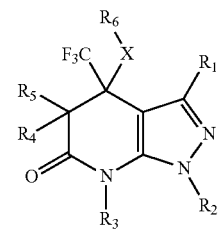

wherein $R_1$, $R_2$, $R_3$, $R_4$, $R_5$, $R_6$ and X have the meaning as defined above,
and, optionally,
b) converting residue $R_6$ as defined above into another residue $R_6$ as defined above, e.g. by introducing an alkyl group,
and optionally
c) converting a base or an acid of the compound of formula (I) into a salt thereof.

In the course of this invention, a "leaving group" is a molecular fragment that departs with a pair of electrons in heterolytic bond cleavage. Leaving groups can be anions or neutral molecules. Common anionic leaving groups are halides such as $Cl^-$, $Br^-$, and $I^-$, and sulfonate esters, such as para-toluenesulfonate or "tosylate" ($TsO^-$). Common neutral molecule leaving groups are water ($H_2O$), ammonia ($NH_3$), and alcohols (ROH).

The ability of a leaving group to depart is correlated with the $pK_a$ of the conjugate acid, with lower $pK_a$ being associated with better leaving group ability. The correlation is not perfect because leaving group ability is a kinetic phenomenon, relating to a reaction's rate, whereas $pK_a$ is a thermodynamic phenomenon, describing the position of an equilibrium. Nevertheless, it is a general rule that more highly stabilized anions act as better leaving groups. Consistent with this rule, strong bases such as alkoxide ($RO^-$), hydroxide ($HO^-$), and amide ($R_2N^-$) are poor leaving groups.

Preferred leaving groups in the course of the present invention are the following:

| Leaving groups ordered approximately in decreasing ability to leave | |
|---|---|
| *R—$N_2^+$ | diazonium salts |
| R—$OR'_2^+$ | |
| R—$OSO_2C_4F_9$ | nonaflates |
| R—$OSO_2CF_3$ | triflates |
| R—$OSO_2F$ | fluorosulfonates |
| R—OTs, R—OMs, etc. | tosylates, mesylates, and similar |
| R—I | iodides |
| R—Br | bromides |
| R—$OH_2^+$ | (Conjugate acid of an alcohol) |

-continued

| Leaving groups ordered approximately in decreasing ability to leave | |
|---|---|
| R—Cl | chlorides, and acyl chloride when attached to carbonyl carbon |
| R—OHR'+ | Conjugate acid of an ether |
| R—ONO$_2$, R—OPO(OH)$_2$ | nitrates, phosphates, and other inorganic esters |
| R—SR'$_2^+$ | |
| R—NR'$_3^+$ | tetraalkylammonium Salts |
| R—F | fluorides |
| R—OCOR | esters, and acid anhydrides when attached to carbonyl carbon |
| R—NH$_3^+$ | ammonium salts |
| R—OAr | phenoxides |
| R—OH | alcohols, and carboxylic acids when attached to carbonyl carbon |
| R—OR | ethers, and esters when attached to carbonyl carbon |

It is uncommon for groups such as H$^-$ (hydrides), R$_3$C$^-$ (alkyl anions, R=alkyl or H), or R$_2$N$^-$ (amides, R=alkyl or H) to depart with a pair of electrons because of the instability of these bases.

Some crude products were subjected to standard chromatography using solvent mixtures containing methanol, ethanol, isopropanol, n-hexane, cyclohexane, dichloromethane, n-heptane or petrol ether, respectively.

For a further detailed description of the manufacturing processes, please refer also to the examples and the following general description of the preferred conditions.

A physiologically acceptable salt of a compound of the invention can also be obtained by isolating and/or treating the compound of the invention obtained by the described reaction with an acid or a base.

The compounds of the invention and also the starting materials for their preparation are, are prepared by methods as described in the examples or by methods known per se, as described in the literature (for example in standard works, such as Houben-Weyl, Methoden der Organischen Chemie [Methods of Organic Chemistry], Georg Thieme Verlag, Stuttgart; Organic Reactions, John Wiley & Sons, Inc., New York), to be precise under reaction conditions which are known and suitable for the said reactions. Use can also be made here of variants which are known per se, but are not mentioned here in greater detail.

The starting materials for the claimed process may, if desired, also be formed in situ by not isolating them from the reaction mixture, but instead immediately converting them further into the compounds of the invention. On the other hand, it is possible to carry out the reaction stepwise.

Preferably, the reaction of the compounds is carried out in the presence of a suitable solvent, which is preferably inert under the respective reaction conditions. Examples of suitable solvents are hydrocarbons, such as hexane, petroleum ether, benzene, toluene or xylene; chlorinated hydrocarbons, such as trichlorethylene, 1,2-dichloroethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether or ethylene glycol dimethyl ether (diglyme); ketones, such as acetone or butanone; amides, such as acetamide, dimethylacetamide, dimethylformamide (DMF) or N-methylpyrrolidinone (NMP); nitriles, such as acetonitrile; sulfoxides, such as dimethyl sulfoxide (DMSO); nitro compounds, such as nitromethane or nitrobenzene; esters, such as ethyl acetate, or mixtures of the said solvents or mixtures with water. Polar solvents are in general preferred. Examples for suitable polar solvents are chlorinated hydrocarbons, alcohols, glycol ethers, nitriles, amides and sulfoxides or mixtures thereof. More preferred are amides, especially dimethylformamide (DMF).

As stated above, the reaction temperature is between about −100° C. and 300° C., depending on the reaction step and the conditions used.

Reaction times are generally in the range between some minutes and several days, depending on the reactivity of the respective compounds and the respective reaction conditions. Suitable reaction times are readily determinable by methods known in the art, for example reaction monitoring. Based on the reaction temperatures given above, suitable reaction times generally lie in the range between 10 min and 48 hrs.

A base of a compound of the invention can be converted into the associated acid-addition salt using an acid, for example by reaction of equivalent amounts of the base and the acid in a preferably inert solvent, such as ethanol, followed by evaporation. Suitable acids for this reaction are, in particular, those which give physiologically acceptable salts. Thus, it is possible to use inorganic acids, for example sulfuric acid, sulfurous acid, dithionic acid, nitric acid, hydrohalic acids, such as hydrochloric acid or hydrobromic acid, phosphoric acids, such as, for example, orthophosphoric acid, sulfamic acid, furthermore organic acids, in particular aliphatic, alicyclic, araliphatic, aromatic or heterocyclic monobasic or polybasic carboxylic, sulfonic or sulfuric acids, for example formic acid, acetic acid, propionic acid, hexanoic acid, octanoic acid, decanoic acid, hexadecanoic acid, octadecanoic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, trimethoxybenzoic acid, adamantanecarboxylic acid, p-toluenesulfonic acid, glycolic acid, embonic acid, chlorophenoxyacetic acid, aspartic acid, glutamic acid, proline, glyoxylic acid, palmitic acid, parachlorophenoxyisobutyric acid, cyclohexanecarboxylic acid, glucose 1-phosphate, naphthalenemono- and -disulfonic acids or laurylsulfuric acid.

Salts with physiologically unacceptable acids, for example picrates, can be used to isolate and/or purify the compounds of the invention.

On the other hand, compounds of the invention can be converted into the corresponding metal salts, in particular alkali metal salts or alkaline earth metal salts, or into the corresponding ammonium salts, using bases (for example sodium hydroxide, potassium hydroxide, sodium carbonate or potassium carbonate). Suitable salts are furthermore substituted ammonium salts, for example the dimethyl-, diethyl- and diisopropylammonium salts, monoethanol-, diethanol- and diisopropanolammonium salts, cyclohexyl- and dicyclohexylammonium salts, dibenzylethylenediammonium salts, furthermore, for example, salts with arginine or lysine.

If desired, the free bases of the compounds of the invention can be liberated from their salts by treatment with strong bases, such as sodium hydroxide, potassium hydroxide, sodium carbonate or potassium carbonate, so long as no further acidic groups are present in the molecule. In the cases where the compounds of the invention have free acid groups, salt formation can likewise be achieved by treatment with bases. Suitable bases are alkali metal hydroxides, alkaline earth metal hydroxides or organic bases in the form of primary, secondary or tertiary amines.

Every reaction step described herein can optionally be followed by one or more working up procedures and/or isolating procedures. Suitable such procedures are known in the art, for example from standard works, such as Houben-Weyl, Methoden der organischen Chemie [Methods of Organic Chemistry], Georg-Thieme-Verlag, Stuttgart). Examples for such procedures include, but are not limited to evaporating a solvent, distilling, crystallization, fractionised crystallization, extraction procedures, washing procedures, digesting procedures, filtration procedures, chromatography, chromatography by HPLC and drying procedures, especially drying procedures in vacuo and/or elevated temperature.

The object of the present invention has surprisingly been solved in another aspect by providing a medicament comprising at least one compound of the invention. In a preferred embodiment, such medicament in addition explicitly comprises compound 2 (4-Hydroxy-3-phenyl-4-trifluoromethyl-1,4,5,7-tetrahydro-pyrazolo[3,4-b]pyridin-6-one) of the present invention.

The object of the present invention has surprisingly been solved in another aspect by providing a medicament comprising at least one compound of the invention for use in the treatment and/or prophylaxis of physiological and/or pathophysiological conditions selected from the group consisting of: "cancer, tumour, malignant tumours, benign tumours, solid tumours, sarcomas, carcinomas, hyperproliferative disorders, carcinoids, Ewing sarcomas, Kaposi sarcomas, brain tumours, tumours originating from the brain and/or the nervous system and/or the meninges, gliomas, glioblastomas, neuroblastomas, stomach cancer, kidney cancer, kidney cell carcinomas, prostate cancer, prostate carcinomas, connective tissue tumours, soft tissue sarcomas, pancreas tumours, liver tumours, head tumours, neck tumours, laryngeal cancer, oesophageal cancer, thyroid cancer, osteosarcomas, retinoblastomas, thymoma, testicular cancer, lung cancer, lung adenocarcinoma, small cell lung carcinoma, bronchial carcinomas, breast cancer, mamma carcinomas, intestinal cancer, colorectal tumours, colon carcinomas, rectum carcinomas, gynaecological tumours, ovary tumours/ovarian tumours, uterine cancer, cervical cancer, cervix carcinomas, cancer of body of uterus, corpus carcinomas, endometrial carcinomas, urinary bladder cancer, urogenital tract cancer, bladder cancer, skin cancer, epithelial tumours, squamous epithelial carcinoma, basaliomas, spinaliomas, melanomas, intraocular melanomas, leukaemias, monocyte leukaemia, chronic leukaemias, chronic myelotic leukaemia, chronic lymphatic leukemia, acute leukaemias, acute myelotic leukaemia, acute lymphatic leukemia, lymphomas, opthalmic diseases, choroidal neovascularization, diabetic retinopathy, inflammatory diseases, arthritis, neurodegeneration, transplant rejection, metastatic growth, fibrosis, restenosis, HIV infection, atherosclerosis, inflammation, heart failure, cardiomyopathy, myocardial infarction, myocardial remodeling, vascular remodeling, hypertension, peripheral arterial occlusive disease, restenosis, thrombosis, vascular permeability disorders, inflammatory diseases, rheumatoid arthritis, osteoarthritis, renal diseases, renal papillary necrosis, renal failure, pulmonary diseases, chronic obstructive pulmonary disease, asthma, acute respiratory dystress syndrome, immunological diseases, allergic diseases, tumor growth, metastasis, metabolic diseases, fibrotic diseases, pulmonary fibrosis, cardiac fibrosis, vascular fibrosis, perivascular fibrosis, renal fibrosis, liver fibrosis, fibrosing skin conditions, psoriasis, pain, pruritis, retinal ischemia/reperfusion damage, macular degeneration, psychiatric disorders, neurodegenerative diseases, cerebral nerve disorders, peripheral nerve disorders, endocrinic disorders, hyperthyroidism, scarring disorders or for cardioprotection or renoprotection and disorders of wound healing, angiogenesis, cardiovascular system, bone, CNS and/or PNS." In a preferred embodiment, such medicament in addition explicitly comprises compound 2 (4-Hydroxy-3-phenyl-4-trifluoromethyl-1,4,5,7-tetrahydro-pyrazolo[3,4-b]pyridin-6-one) of the present invention. A corresponding use for the preparation of a medicament for the treatment and/or prophylaxis of the aforementioned conditions is intended to be comprised. A corresponding method of treatment administering at least one compound of the invention to a patient in need thereof is also intended to be comprised.

Compounds of the invention may be used in combination with one or more other active substances (ingredients, drugs) in the treatment, prevention, suppression or amelioration of diseases or conditions for which compounds of the invention or the other substances have utility. Typically the combination of the drugs is safer or more effective than either drug alone, or the combination is safer or more effective than would it be expected based on the additive properties of the individual drugs. Such other drug(s) may be administered, by a route and in an amount commonly used contemporaneously or sequentially with a compound of the invention. When a compound of the invention is used contemporaneously with one or more other drugs, a combination product containing such other drug(s) and the compound of the invention is preferred. However, combination therapy also includes therapies in which the compound of the invention and one or more other drugs are administered on different overlapping schedules. It is contemplated that when used in combination with other active ingredients, the compound of the present invention or the other active ingredient or both may be used effectively in lower doses than when each is used alone. Accordingly, the pharmaceutical compositions of the present invention include those that contain one or more other active ingredients, in addition to a compound of the invention.

Examples of other active substances (ingredients, drugs) that may be administered in combination with a compound of the invention, and either administered separately or in the same pharmaceutical composition, include, but are not limited to the compounds classes and specific compounds listed in Table 1:

TABLE 1

| | | |
|---|---|---|
| Alkylating agents | Cyclophosphamide | Lomustine |
| | Busulfane | Procarbazine |
| | Ifosfamide | Altretamine |
| | Melphalane | Estramustinphosphate |
| | Hexamethylmelamine | Mechlorethamine |
| | Thiotepa | Streptozocine |
| | Chlorambucil | Temozolomide |
| | Dacarbazine | Semustine |
| | Carmustine | |
| Platinum agents | Cisplatin | Carboplatin |
| | Oxaliplatin | ZD-0473 (AnorMED) |
| | Spiroplatin | Lobaplatin (AeternaZentaris) |

TABLE 1-continued

| | | |
|---|---|---|
| | Carboxyphthalatoplatinum<br>Tetraplatin<br>Ormiplatin<br>Iproplatin | Satraplatin (Johnson Matthey)<br>BBR-3464 (Hoffrnann-La Roche)<br>SM-11355 (Sumitomo)<br>AP-5280 (Access) |
| Antimetabolites | Azacytidine<br>Gemcitabine<br>Capecitabine<br>5-Fluoruracil<br>Floxuridine<br>2-Chlordesoxyadenosine<br>6-Mercaptopurine<br>6-Thioguanine<br>Cytarabine<br>2-Fluordesoxycytidine<br>Methotrexate<br>Idatrexate | Tomudex<br>Trimetrexate<br>Deoxycoformycine<br>Fludarabine<br>Pentostatine<br>Raltitrexede<br>Hydroxyurea<br>Decitabine (SuperGen)<br>Clofarabine (Bioenvision)<br>Irofulven (MGI Pharma)<br>DMDC (Hoffmann-La Roche)<br>Ethinylcytidine (Taiho) |
| Topoisomerase inhibitors | Amsacrine<br>Epirubicine<br>Etoposide<br>Teniposide or Mitoxantrone<br>Irinotecane (CPT-11)<br>7-Ethyl-10-hydroxycamptothecine<br>Topotecane<br>Dexrazoxanet (TopoTarget)<br>Pixantrone (Novuspharrna)<br>Rebeccamycin-Analogue (Exelixis)<br>BBR-3576 (Novuspharrna) | Rubitecane (SuperGen)<br>Exatecanmesylate (Daiichi)<br>Quinamed (ChemGenex)<br>Gimatecane (Sigma- Tau)<br>Diflomotecane (Beaufour-Ipsen)<br>TAS-103 (Taiho)<br>Elsamitrucine (Spectrum)<br>J-107088 (Merck & Co)<br>BNP-1350 (BioNumerik)<br>CKD-602 (Chong Kun Dang)<br>KW-2170 (Kyowa Hakko) |
| Antitumour antibiotics | Dactinomycin (Actinomycin D)<br>Doxorubicin (Adriamycin)<br>Deoxyrubicin<br>Valrubicin<br>Daunorubicin (Daunomycin)<br>Epirubicin<br>Therarubicin<br>Idarubicin<br>Rubidazone<br>Plicamycinp<br>Porfiromycin<br>Cyanomorpholinodoxorubicin<br>Mitoxantron (Novantron) | Amonafide<br>Azonafide<br>Anthrapyrazole<br>Oxantrazole<br>Losoxantrone<br>Bleomycinsulfate (Blenoxan)<br>Bleomycinacid<br>Bleomycin A<br>Bleomycin B<br>Mitomycin C<br>MEN-10755 (Menarini)<br>GPX-100 (Gem Pharmaceuticals) |
| Antimitotic agents | Paclitaxel<br>Docetaxel<br>Colchicin<br>Vinblastine<br>Vincristine<br>Vinorelbine<br>Vindesine<br>Dolastatine 10 (NCI)<br>Rhizoxine (Fujisawa)<br>Mivobuline (Warner-Lambert)<br>Cemadotine (BASF)<br>RPR 109881A (Aventis)<br>TXD 258 (Aventis)<br>Epothilon B (Novartis)<br>T 900607 (Tularik)<br>T 138067 (Tularik)<br>Cryptophycin 52 (Eli Lilly)<br>Vinflunine (Fabre)<br>Auristatine PE (Teikoku Hormone)<br>BMS 247550 (BMS)<br>BMS 184476 (BMS)<br>BMS 188797 (BMS)<br>Taxoprexine (Protarga) | SB 408075 (GlaxoSmithKline)<br>E7010 (Abbott)<br>PG-TXL (Cell Therapeutics)<br>IDN 5109 (Bayer)<br>A 105972 (Abbott)<br>A 204197 (Abbott)<br>LU 223651 (BASF)<br>D 24851 (ASTA Medica)<br>ER-86526 (Eisai)<br>Combretastatine A4 (BMS)<br>Isohomohalichondrin-B (PharmaMar)<br>ZD 6126 (AstraZeneca)<br>PEG-Paclitaxel (Enzon)<br>AZ10992 (Asahi)<br>!DN-5109 (Indena)<br>AVLB (Prescient NeuroPharma)<br>Azaepothilon B (BMS)<br>BNP- 7787 (BioNumerik)<br>CA-4-Prodrug (OXiGENE)<br>Dolastatin-10 (NrH)<br>CA-4 (OXiGENE) |
| Aromatase inhibitors | Aminoglutethimide<br>Letrozole<br>Anastrazole<br>Formestane | Exemestane<br>Atamestane (BioMedicines)<br>YM-511 (Yamanouchi) |
| Thymidylatesynthase inhibitors | Pemetrexed (Eli Lilly)<br>ZD-9331 (BTG) | Nolatrexed (Eximias)<br>CoFactor ™ (BioKeys) |
| DNA antagonists | Trabectedine (PharmaMar)<br>Glufosfamide (Baxter International)<br>Albumin + 32P (Isotope Solutions) | Mafosfamide (Baxter International)<br>Apaziquone (Spectrum Pharmaceuticals)<br>O6-Benzylguanine (Paligent) |

TABLE 1-continued

| | | |
|---|---|---|
| | Thymectacine (NewBiotics) | |
| | Edotreotide (Novartis) | |
| Farnesyltransferase inhibitors | Arglabine (NuOncology Labs) | Tipifarnibe (Johnson & Johnson) |
| | Ionafarnibe (Schering-Plough) | Perillylalcohol (DOR BioPharma) |
| | BAY-43-9006 (Bayer) | |
| Pump inhibitors | CBT-1 (CBA Pharma) | Zosuquidar-Trihydrochloride (Eli Lilly) |
| | Tariquidar (Xenova) | Biricodar-Dicitrate (Vertex) |
| | MS-209 (Schering AG) | |
| Histoneacetyltransferase inhibitors | Tacedinaline (Pfizer) | Pivaloyloxymethylbutyrate (Titan) |
| | SAHA (Aton Pharma) | |
| | MS-275 (Schering AG) | Depsipeptide (Fujisawa) |
| Metalloproteinase inhibitors/ Ribonucleosidereduktase inhibitors | Neovastat (Aeterna Laboratories) | CMT -3 (CollaGenex) |
| | | BMS-275291 (Celltech) |
| | Marimastat (British Biotech) | Tezacitabine (Aventis) |
| | Galliummaltolate (Titan) | Didox (Molecules for Health) |
| | Triapine (Vion) | |
| TNF-alpha agonists/ antagonists | Virulizine (Lorus Therapeutics) | Revimide (Celgene) |
| | CDC-394 (Celgene) | |
| Endothelin-A receptor antagonists | Atrasentane (Abbot) | YM-598 (Yamanouchi) |
| | ZD-4054 (AstraZeneca) | |
| Retinoic acid receptor agonists | Fenretinide (Johnson & Johnson) | Alitretinoin (Ligand) |
| | LGD-1550 (Ligand) | |
| Immunomodulators | Interferon | Dexosome therapy (Anosys) |
| | Oncophage (Antigenics) | Pentrix (Australian Cancer Technology) |
| | GMK (Progenies) | |
| | Adenocarzinoma vaccine (Biomira) | JSF-154 (Tragen) |
| | | Cancer vaccine (Intercell) |
| | CTP-37 (AVI BioPharma) | Noreline (Biostar) |
| | JRX-2 (Immuno-Rx) | BLP-25 (Biomira) |
| | PEP-005 (Peplin Biotech) | MGV (Progenics) |
| | Synchrovax vaccine (CTL Immuno) | 13-Alethine (Dovetail) |
| | Melanoma vaccine (CTL Immuno) | CLL-Thera (Vasogen) |
| | p21-RAS vaccine (GemVax) | |
| Hormonal and anti-hormonal agents | Estrogens | Prednisone |
| | Conjugated Estrogens | Methylprednisolone |
| | Ethinylestradiole | Prednisolone |
| | Chlorotrianisen | Aminoglutethimide |
| | Idenestrole | Leuprolide |
| | Hydroxyprogesteroncaproate | Goserelin |
| | Medroxyprogesterone | Leuporelin |
| | Testosterone | Cetrorelix |
| | Testosteronpropionate | Bicalutamide |
| | Fluoxymesterone | Flutamide |
| | Methyltestosterone | Octreotide |
| | Diethylstilbestrole | Nilutamide |
| | Megestrole | Mitotane |
| | Tamoxifen | P-04 (Novogen) |
| | Toremofine | 2-Methoxyoestradiol (EntreMed) |
| | Dexamethasone | Arzoxifen (Eli Lilly) |
| Photodynamic agents | Talaporfine (Light Sciences) | Pd-Bacteriopheophorbide (Yeda) |
| | Theralux (Theratechnologies) | |
| | Motexafin Gadolinium (Pharmacyclics) | Lutetium-Texaphyrine (Pharmacyclics) |
| | | Hypericine |
| Tyrosinkinase inhibitors | Imatinib (Novartis) | Kahalid F (PharmaMar) |
| | Leflunomid (Sugen/Pharmacia) | CEP-701 (Cephalon) |
| | | CEP-751 (Cephalon) |
| | ZDI839 (AstraZeneca) | MLN518 (Millenium) |
| | Erlotinib (Oncogene Science) | PKC412 (Novartis) |
| | Canertjnib (Pfizer) | Phenoxodiol O |
| | Squalamin (Genaera) | Trastuzumab (Genentech) |
| | SU5416 (Pharmacia) | C225 (ImClone) |
| | SU6668 (Pharmacia) | rhu-Mab (Genentech) |
| | ZD4190 (AstraZeneca) | MDX-H210 (Medarex) |
| | ZD6474 (AstraZeneca) | 2C4 (Genentech) |
| | Vatalanib (Novartis) | MDX-447 (Medarex) |
| | PKI166 (Novartis) | ABX-EGF (Abgenix) |
| | GW2016 (GlaxoSmithKline) | IMC-1C11 (ImClone) |
| | EKB-509 (Wyeth) | |
| | EKB-569 (Wyeth) | |
| Different agents | SR-27897 (CCK-A inhibitor, Sanofi-Synthelabo) | BCX-1777 (PNP inhibitor, BioCryst) |
| | Tocladesine (cyclic-AMP agonist, Ribapharm) | Ranpirnase (Ribonuclease stimulans, Alfacell) |

TABLE 1-continued

| | |
|---|---|
| Alvocidib (CDK inhibitor, Aventis) | Galarubicin (RNA synthesis inhibitor, Dong-A) |
| CV-247 (COX-2 Inhibitor, Ivy Medical) | Tirapazamin (reducing agent, SRI International) |
| P54 (COX-2 inhibitor, Phytopharm) | N-Acetylcystein (reducing agent, Zambon) |
| CapCell ™ (CYP450 stimulans, Bavarian Nordic) | R-Flurbiprofen (NF-kappaB inhibitor, Encore) |
| GCS-IOO (gal3 antagonist, GlycoGenesys) | 3CPA (NF-kappaB inhibitor, Active Biotech) |
| G17DT immunogen (Gastrin inhibitor, Aphton) | Seocalcitol (Vitamin-D receptor agonist, Leo) |
| Efaproxiral (Oxygenator, Allos Therapeutics) | 131-I-TM-601 (DNA antagonist, TransMolecular) |
| PI-88 (Heparanase inhibitor, Progen) | Eflornithin (ODC inhibitor, ILEX Oncology) |
| Tesmilifen (Histamine antagonist, YM BioSciences) | Minodronic acid (Osteoclasts inhibitor, Yamanouchi) |
| Histamine (Histamine-H2 receptor agonist, Maxim) | Indisulam (p53 stimulans, Eisai) |
| Tiazofurin (IMPDH inhibitor, Ribapharm) | Aplidin (PPT inhibitor, PharmaMar) |
| Cilengitide (Integrine antagonist, Merck KGaA) | Rituximab (CD20 antibody, Genentech) |
| SR-31747 (IL-1 antagonist, Sanofi-Synthelabo) | Gemtuzumab (CD33 antibody, Wyeth Ayerst) |
| CCI-779 (mTOR kinase inhibitor, Wyeth) | PG2 (Hematopoesis enhancer, Pharmagenesis) |
| Exisulind (PDE-V inhibitor, Cell Pathways) | Immunol ™ (Triclosan oral irrigation, Endo) |
| CP-461 (PDE-V inhibitor, Cell Pathways) | Triacetyluridine (Uridine prodrug, Wellstat) |
| AG-2037 (GART inhibitor, Pfizer) | SN-4071 (sarcoma agent, Signature BioScience) |
| WX-UK1 (Plasminogen activator inhibitor, Wilex) | TransMID-107 ™ (Immunotoxine, KS Biomedix) |
| PBI-1402 (PMN stimulans, ProMetic LifeSciences) | PCK-3145 (Apoptosis enhancer, Procyon) |
| Bortezomib (Proteasome inhibitor, Millennium) | Doranidazole (Apoptosis enhancer, Pola) |
| SRL-172 (T-cell stimulans, SR Pharma) | CHS-828 (cytotoxic agent, Leo) |
| TLK-286 (Glutathione-S-transferase inhibitor, Telik) | trans-Retinoic acid (Differentiator, NIH) |
| PT-100 (Growth factor agonist, Point Therapeutics) | MX6 (Apoptosis enhancer, MAXIA) |
| Midostaurin (PKC inhibitor, Novartis) | Apomin (Apoptosis enhancer, ILEX Oncology) |
| Bryostatin-1 (PKC stimulans, GPC Biotech) | Urocidine (Apoptosis enhancer, Bioniche) |
| CDA-II (Apoptosis enhancer, Everlife) | Ro-31-7453 (Apoptosis enhancer, La Roche) |
| SDX-101 (Apoptosis enhancer, Salmedix) | Brostallicin (Apoptosis enhancer, Pharmacia) |
| Ceflatonin (Apoptosis enhancer, ChemGenex) | |

In a preferred embodiment, a compound of the invention is administered in combination with one or more known antitumor agents, such as the following: estrogen receptor modulators, androgen receptor modulators, retinoid receptor modulators, cytotoxics, antiproliferative agents, prenyl proteintransferase inhibitors, HMG-CoA-reductase inhibitors, HIV protease inhibitors, reverse transcriptase inhibitors, angiogenesis inhibitors. The compounds of the present inventions are particularly suitable for administration at the same time as radiotherapy.

The compounds of the invention are in particular well suited for administration in combination with radiotherapy. The synergistic effects of VEGF inhibition in combination with radiotherapy are known to the skilled artisan (WO 00/61186).

The term "estrogen receptor modulators" in the course of the present invention refers to compounds that interfere with or inhibit the binding of estrogen to estrogen receptor—independently from the mode of action. Non-limiting examples of estrogen receptor modulators are tamoxifen, raloxifen, idoxifen, LY353381, LY 117081, toremifen, fulvestrant, 4-[7-(2, 2-Dimethyl-1-oxopropoxy-4-methyl-2-[4-[2-(1-piperidinyl) ethoxy]phenyl]-2H-1-benzopyran-3-yl]phenyl-2,2-dimethyl-propanoate, 4,4'-Dihydroxybenzophenon-2,4-dinitrophenylhydrazone and SH646.

The term "androgen receptor modulators" in the course of the present invention refers to compounds that interfere with or inhibit the binding of androgens to androgen receptor—independently from the mode of action. Non-limiting examples of androgen receptor modulators are finasteride and other 5alpha-reductase inhibitors, nilutamide, flutamide, bicalutamide, liarozole and abirateron acetate.

The term "retinoid receptor modulators" in the course of the present invention refers to compounds that interfere with or inhibit the binding of retinoids to retinoid receptor—independently from the mode of action. Non-limiting examples of retinoid receptor modulators are bexaroten, tretinoin, 13-cis-retinoic acid, 9-cis-retinoic acid, alpha-difluoromethylornithine, ILX23-7553, trans-N-(4'-Hydroxyphenyl)retinamide and N-4-carboxyphenylretinamide.

The term "cytotoxics" in the course of the present invention refers to compounds that primarily trigger cell death through direct action on cell function(s) or which interfere with or inhibit cell myosis, such as alkylating agents, tumor necrosis factors, intercalating agents, microtubule inhibitors and topoisomerase inhibitors. Non-limiting examples of cytotoxics are tirapazimin, sertenef, cachectine, ifosfamide, tasonermine, lonidamine, carboplatin, altretamine, prednimustine, dibromodulcit, ranimustine, fotemustine, nedaplatin, oxaliplatin, temozolomide, heptaplatin, estramustin, improsulfantosylate, trofosfamide, nimustine, dibrospidium-chloride, pumitepa, lobaplatin, satraplatin, profiromycin, cisplatin, irofulven, dexifosfamide, cis-amindichloro(2-methylpyridine)platin, benzylguanine, glufosfamide, GPX100, (trans, trans,trans)-bis-mu-(hexane-1,6-diamine)-mu-[diamine-platin(II)]bis-[diamine(chloro)platin(II)]-tetrachloride, diarizidinylspermine, arsenium trioxide, 1-(11-Dodecylamino-10-hydroxyundecyl)-3,7-dimethylxanthine, zorubicin, idarubicin, daunorubicin, bisantren, mitoxantron, pirarubicin, pinafide, valrubicine, amrubicine, antineoplaston, 3'-desamino-3'-morpholino-13-desoxo-10-hydroxycaminomycin, annamycin, galarubicin, elinafide, MEN10755 and 4-desmethoxy-3-desamino-3-aziridinyl-4-methylsulfonyl-daunorubicin (WO 00/50032).

Non-limiting examples of microtubule inhibitors are paclitaxel, vindesine-sulfate, 3',4'-dideshydro-4'-desoxy-8'-norvincaleukoblastine, docetaxol, rhizoxine, dolastatine, mivobuline-isethionate, auristatine, cemadotine, RPR109881, BMS184476, vinflunine, cryptophycine, 2,3,4,5,6-pentafluoro-N-(3-fluoro-4-methoxyphenyl)-benzenesulfonamide, anhydrovinblastine, N,N-dimethyl-L-valyl-L-valyl-N-methyl-L-valyl-L-prolyl-L-proline-t-butylamide, TDX258 and BMS188797.

Non-limiting examples of topoisomerase inhibitors are topotecane, hycaptamine, irinotecane, rubitecane, 6-ethoxypropionyl-3',4'-O-exo-benzylidene-chartreusine, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzoidOpyrano-[3',4':b,7] indolizino[1,2b]quiinoline-10,13(9H,15H)-dione, lurtotecane, 7-[2-(N-isopropylamino)ethyl]-(20S)camptothecine, BNP1350, BNPI1100, BN80915, BN80942, etoposide-phosphate, teniposide, sobuzoxane, 2'-dimethylamino-2'-desoxy-etoposide, GL331, N-[2-(dimethylamino)ethyl]-9-hydroxy-5,6-dimethyl-6H-pyrido[4,3-b]carbazole-1-carboxamide, asulacrine, (5a,5aB,8aa,9b)-9-[2-[N-[2-(dimethylamino)ethyl]-N-methylamino]ethyl]-5-[4-hydroxy-3,5-dimethoxyphenyl]-5,5a,6,8,8a,9-hexohydrofuro(3',4':6,7)naphtho(2,3-d)-1,3-dioxol-6-one, 2,3-(methylendioxy)-5-methyl-7-hydroxy-8-methoxybenzo[c]phenanthridinium, 6,9-bis[(2-aminoethyl)amino]-benzo[g]isoquinoline-5,10-dione, 5-(3-aminopropylamino)-7,10-dihydroxy-2-(2-hydroxyethylaminomethyl)-6H-pyrazolo[4,5,1-de]-acridine-6-one, N-[1-[2(diethylamino)ethylamino]-7-methoxy-9-oxo-9H-thioxane-then-4-ylmethyl]formamide, N-(2-(dimethyl-amino)-ethyl)acridine-4-carboxamide, 6-[[2-(dimethylamino)-ethyl]amino]-3-hydroxy-7H-indeno[2,1-c]quinolin-7-one and dimesna.

Non-limiting examples of antiproliferative agents are antisense RNA- and antisense-DNA oligonucleotides, such as G3139, ODN698, RVASKRAS, GEM231 and INX3001, as well as antimetabolites scuh as enocitabine, carmofur, tegafur, pentostatine, doxifluridine, trimetrexate, fludarabine, capecitabine, galocitabine, cytarabin-ocfosfate, fosteabine sodiumhydrate, raltitrexed, paltitrexide, emitefur, tiazof urine, decitabine, nolatrexed, pemetrexed, nelzarabine, 2'-desoxy-2'-methylidencytidine, 2'-fluoromethylen-2'-desoxycytidine, N-[5-(2,3-dihydrobenzofuryl)sulfonyl]-N'-(3, 4-dichlorophenyl)urea, N6-[4-desoxy-4-[N2-[2(E),4(E)-tetradecadienoyl]glycylamino]-L-glycero-B-L-manno-heptopyranosyl]adenine, aplidine, ecteinascidine, troxacitabine, 4-[2-amino-4-oxo-4,6,7,8-tetrahydro-3H-pyrimidino[5,4-b][1,4]thiazine-6-yl-(S)-ethyl]-2,5-thienoyl-L-glutaminic acid, aminopterine, 5-fluorouracil, alanosine, 11-acetyl-8-(carbamoyloxymethyl)-4-formyl-6-methoxy-14-oxa-1,11-diaza-tetracyclo-(7.4.1.0.0)-tetradeca-2,4,6-trien-9-ylacetic acid ester, swainsonine, lometrexole, dexrazoxane, methioninase, 2'-cyan-2'-desoxy-N4-palmitoyl-1-B-D-arabinofuranosylcytosine and 3-aminopyridine-2-carboxaldehyde-thiosemicarbazone.

"Antiproliferative agents" also comprises monoclonal antibodies against growth factors that have not been listed under "angiogenesis inhibitors", such as trastuzumab, as well as tumor suppressor genes, such as p53.

In another aspect of the invention, a medicament according to above aspects and embodiments is provided, wherein in such medicament comprises at least one additional pharmacologically active substance (drug, ingredient).

In a preferred embodiment the at least one pharmacologically active substance is a substance as described herein.

In another aspect of the invention, a medicament according to above aspects and embodiments is provided, wherein the medicament is applied before and/or during and/or after treatment with at least one additional pharmacologically active substance.

In a preferred embodiment the at least one pharmacologically active substance is a substance as described herein.

In another aspect of the invention, a pharmaceutical composition comprising a therapeutically effective amount of at least one compound of the invention is provided.

In a preferred embodiment, the pharmaceutical composition contains at least one additional compound selected from the group consisting of physiologically acceptable excipients, auxiliaries, adjuvants, diluents, carriers and/or additional pharmaceutically active substance other than the compounds of the invention.

In another aspect of the invention, a pharmaceutical composition is disclosed which comprises at least one compound of the invention, at least one pharmacologically active substance other than the compounds of the invention as described herein; and a pharmaceutically acceptable carrier.

A further embodiment of the present invention is a process for the manufacture of said pharmaceutical compositions, characterized in that one or more compounds according to the invention and one or more compounds selected from the group consisting of solid, liquid or semiliquid excipients, auxiliaries, adjuvants, diluents, carriers and pharmaceutically active agents other than the compounds according to the invention, are converted in a suitable dosage form.

In another aspect of the invention, a kit is provided comprising a therapeutically effective amount of at least one compound of the invention and/or at least one pharmaceutical composition as described herein and a therapeutically effective amount of at least one further pharmacologically active substance other than the compounds of the invention.

The pharmaceutical compositions of the present invention may be administered by any means that achieve their intended purpose. For example, administration may be by oral, parenteral, topical, enteral, intravenous, intramuscular, inhalant, nasal, intraarticular, intraspinal, transtracheal, transocular, subcutaneous, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired. Parenteral administration is preferred. Oral administration is especially preferred.

Suitable dosage forms include, but are not limited to capsules, tablets, pellets, dragees, semi-solids, powders, granules, suppositories, ointments, creams, lotions, inhalants, injections, cataplasms, gels, tapes, eye drops, solution, syrups, aerosols, suspension, emulsion, which can be produced according to methods known in the art, for example as described below:

tablets: mixing of active ingredient/s and auxiliaries, compression of said mixture into tablets (direct compression), optionally granulation of part of mixture before compression.

capsules: mixing of active ingredient/s and auxiliaries to obtain a flowable powder, optionally granulating powder, filling powders/granulate into opened capsules, capping of capsules.

semi-solids (ointments, gels, creams): dissolving/dispersing active ingredient/s in an aqueous or fatty carrier; subsequent mixing of aqueous/fatty phase with complementary fatty/aqueous phase, homogenization (creams only).

suppositories (rectal and vaginal): dissolving/dispersing active ingredient/s in carrier material liquified by heat (rectal: carrier material normally a wax; vaginal: carrier normally a heated solution of a gelling agent), casting said mixture into suppository forms, annealing and withdrawal suppositories from the forms.

aerosols: dispersing/dissolving active agent/s in a propellant, bottling said mixture into an atomizer.

In general, non-chemical routes for the production of pharmaceutical compositions and/or pharmaceutical preparations comprise processing steps on suitable mechanical means known in the art that transfer one or more compounds of the invention into a dosage form suitable for administration to a patient in need of such a treatment. Usually, the transfer of one or more compounds of the invention into such a dosage form comprises the addition of one or more compounds, selected from the group consisting of carriers, excipients, auxiliaries and pharmaceutical active ingredients other than the compounds of the invention. Suitable processing steps include, but are not limited to combining, milling, mixing, granulating, dissolving, dispersing, homogenizing, casting and/or compressing the respective active and non-active ingredients. Mechanical means for performing said processing steps are known in the art, for example from Ullmann's Encyclopedia of Industrial Chemistry, 5th Edition. In this respect, active ingredients are preferably at least one compound of the invention and one or more additional compounds other than the compounds of the invention, which show valuable pharmaceutical properties, preferably those pharmaceutical active agents other than the compounds of the invention, which are disclosed herein.

Particularly suitable for oral use are tablets, pills, coated tablets, capsules, powders, granules, syrups, juices or drops, suitable for rectal use are suppositories, suitable for parenteral use are solutions, preferably oil-based or aqueous solutions, furthermore suspensions, emulsions or implants, and suitable for topical use are ointments, creams or powders. The compounds of the invention may also be lyophilised and the resultant lyophilisates used, for example, for the preparation of injection preparations. The preparations indicated may be sterilised and/or comprise assistants, such as lubricants, preservatives, stabilisers and/or wetting agents, emulsifiers, salts for modifying the osmotic pressure, buffer substances, dyes, flavours and/or a plurality of further active ingredients, for example one or more vitamins.

Suitable excipients are organic or inorganic substances, which are suitable for enteral (for example oral), parenteral or topical administration and do not react with the compounds of the invention, for example water, vegetable oils, benzyl alcohols, alkylene glycols, polyethylene glycols, glycerol triacetate, gelatine, carbohydrates, such as lactose, sucrose, mannitol, sorbitol or starch (maize starch, wheat starch, rice starch, potato starch), cellulose preparations and/or calcium phosphates, for example tricalcium phosphate or calcium hydrogen phosphate, magnesium stearate, talc, gelatine, tragacanth, methyl cellulose, hydroxypropylmethylcellulose, sodium carboxymethylcellulose, polyvinyl pyrrolidone and/or vaseline.

If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries include, without limitation, flow-regulating agents and lubricants, for example, silica, talc, stearic acid or salts thereof, such as magnesium stearate or calcium stearate, and/or polyethylene glycol. Dragee cores are provided with suitable coatings, which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices or to provide a dosage form affording the advantage of prolonged action, the tablet, dragee or pill can comprise an inner dosage and an outer dosage component me latter being in the form of an envelope over the former. The two components can be separated by an enteric layer, which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, acetyl alcohol, solutions of suitable cellulose preparations such as acetyl-cellulose phthalate, cellulose acetate or hydroxypropylmethyl-cellulose phthalate, are used. Dye stuffs or pigments may be added to the tablets or dragee coatings, for example, for identification or in order to characterize combinations of active compound doses.

Suitable carrier substances are organic or inorganic substances which are suitable for enteral (e.g. oral) or parenteral administration or topical application and do not react with the novel compounds, for example water, vegetable oils, benzyl alcohols, polyethylene glycols, gelatin, carbohydrates such as lactose or starch, magnesium stearate, talc and petroleum jelly. In particular, tablets, coated tablets, capsules, syrups, suspensions, drops or suppositories are used for enteral administration, solutions, preferably oily or aqueous solutions, furthermore suspensions, emulsions or implants, are used for parenteral administration, and ointments, creams or powders are used for topical application. The compounds of the invention can also be lyophilized and the lyophilizates obtained can be used, for example, for the production of injection preparations.

The preparations indicated can be sterilized and/or can contain excipients such as lubricants, preservatives, stabilizers and/or wetting agents, emulsifiers, salts for affecting the osmotic pressure, buffer substances, colorants, flavourings and/or aromatizers. They can, if desired, also contain one or more further active compounds, e.g. one or more vitamins.

Other pharmaceutical preparations, which can be used orally include push-fit capsules made of gelatine, as well as soft, sealed capsules made of gelatine and a plasticizer such as glycerol or sorbitol. The push-fit capsules can contain the active compounds in the form of granules, which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

The liquid forms in which the novel compositions of the present invention may be incorporated for administration orally include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatine.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400).

Aqueous injection suspensions may contain substances, which increase the viscosity of the suspension, including, for example, sodium carboxymethyl cellulose, sorbitol, and/or dextran, optionally, the suspension may also contain stabilizers.

For administration as an inhalation spray, it is possible to use sprays in which the active ingredient is either dissolved or suspended in a propellant gas or propellant gas mixture (for example $CO_2$ or chlorofluorocarbons). The active ingredient is advantageously used here in micronized form, in which case one or more additional physiologically acceptable solvents may be present, for example ethanol. Inhalation solutions can be administered with the aid of conventional inhalers.

Possible pharmaceutical preparations, which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatine rectal capsules, which consist of a combination of the active compounds with a base. Possible base materials include, for example, liquid triglycerides, polyethylene glycols, or paraffin hydrocarbons.

For use in medicine, the compounds of the present invention will be in the form of pharmaceutically acceptable salts. Other salts may, however, be useful in the preparation of the compounds of the invention or of their pharmaceutically acceptable salts. Suitable pharmaceutically acceptable salts of the compounds of this invention include acid addition salts which may, for example be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic bases, e.g. quaternary ammonium salts.

The pharmaceutical preparations can be employed as medicaments in human and veterinary medicine. As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function. Said therapeutic effective amount of one or more of the compounds of the invention is known to the skilled artisan or can be easily determined by standard methods known in the art.

The compounds of the invention and the additional active substances are generally administered analogously to commercial preparations. Usually, suitable doses that are therapeutically effective lie in the range between 0.0005 mg and 1000 mg, preferably between 0.005 mg and 500 mg and especially between 0.5 mg and 100 mg per dose unit. The daily dose is preferably between about 0.001 mg/kg and 10 mg/kg of body weight.

Those of skill will readily appreciate that dose levels can vary as a function of the specific compound, the severity of the symptoms and the susceptibility of the subject to side effects. Some of the specific compounds are more potent than others. Preferred dosages for a given compound are readily determinable by those of skill in the art by a variety of means. A preferred means is to measure the physiological potency of a given compound.

For the purpose of the present invention, all mammalian species are regarded as being comprised. In a preferred embodiment, such mammals are selected from the group consisting of "primate, human, rodent, equine, bovine, canine, feline, domestic animals, cattle, livestock, pets, cow, sheep, pig, goat, horse, pony, donkey, hinny, mule, hare, rabbit, cat, dog, guinea pig, hamster, rat, mouse". More preferably, such mammals are humans. Animal models are of interest for experimental investigations, providing a model for treatment of human diseases.

The specific dose for the individual patient depends, however, on the multitude of factors, for example on the efficacy of the specific compounds employed, on the age, body weight, general state of health, the sex, the kind of diet, on the time and route of administration, on the excretion rate, the kind of administration and the dosage form to be administered, the pharmaceutical combination and severity of the particular disorder to which the therapy relates. The specific therapeutic effective dose for the individual patient can readily be determined by routine experimentation, for example by the doctor or physician, which advises or attends the therapeutic treatment.

In the case of many disorders, the susceptibility of a particular cell to treatment with the subject compounds may be determined by in vitro testing. Typically a culture of the cell is combined with a subject compound at varying concentrations for a period of time sufficient to allow the active agents to show a relevant reaction, usually between about one hour and one week. For in vitro testing, cultured cells from a biopsy sample may be used.

Even without further details, it is assumed that a person skilled in the art will be able to utilise the above description in the broadest scope. The preferred embodiments should therefore merely be regarded as descriptive disclosure, which is absolutely not limiting in any way.

Above and below, all temperatures are indicated in ° C. In the following examples, "conventional work-up" means that, if necessary, the solvent is removed, water is added if necessary, the pH is adjusted, if necessary, to between 2 and 10, depending on the constitution of the end product, the mixture is extracted with ethyl acetate or dichloromethane, the phases are separated, the organic phase is washed with saturated NaHCO$_3$ solution, if desired with water and saturated NaCl solution, is dried over sodium sulfate, filtered and evaporated, and the product is purified by chromatography on silica gel, by preparative HPLC and/or by crystallisation. The purified compounds are, if desired, freeze-dried.

List of Abbreviations and Acronyms:

AcOH acetic acid, anh anhydrous, atm atmosphere(s), BOC tert-butoxycarbonyl CDI 1,1'-carbonyl diimidazole, conc concentrated, d day(s), dec decomposition, DIAD diisopropyl azodicarboxylate, DMAC NN-dimethylacetamide, DMPU 1,3-dimethyl-3,4,5,6-tetrahydro-2(IH)-pyrimidinone, DMF NN-dimethylformamide, DMSO dimethylsulfoxide, DPPA diphenylphosphoryl azide, EDCI 1-(3-dimethylaminopropyl)-3-ethylcarbodiimide, EtOAc ethyl acetate, EtOH ethanol (100%), Et$_2$O diethyl ether, Et$_3$N triethylamine, h hour(s), MeOH methanol, pet. ether petroleum ether (boiling range 30-60° C.), PPh$_3$ triphenylphospine, temp. temperature, THF tetrahydrofuran, TFA trifluoroAcOH, Tf trifluoromethanesulfonyl.

The contents of all cited references are hereby incorporated by reference in their entirety. The invention is explained in more detail by means of the following examples without, however, being restricted thereto.

EXAMPLES

I. Synthesis of Selected Compounds of the Invention

Example 1

3-(3-Fluoro-phenyl)-4-hydroxy-4-trifluoromethyl-1,4,5,7-tetrahydro-pyrazolo[3,4-b]pyridin-6-one

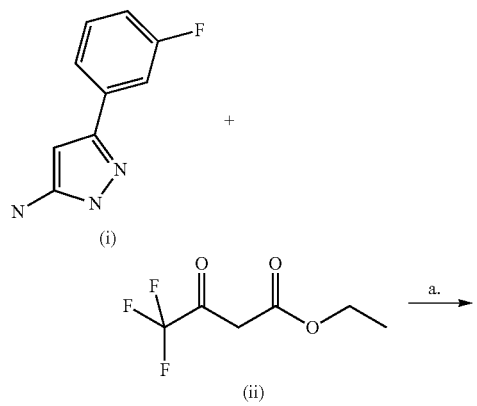

-continued

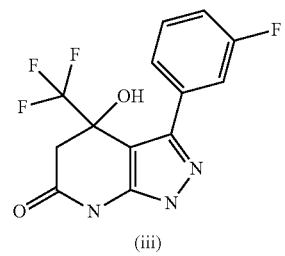

a. 5-(3-Fluoro-phenyl)-2H-pyrazol-3-ylamine (i) (100 mg, 0.56 mmol) was dissolved in glacial acetic acid (1 mL), Ethyl-4,4,4-trifluoracetoacetate (0.12 mL, 0.84 mmol) was added at RT and stirring was continued for 2.5 h at 120° C. The mixture was evaporated to dryness and the isomeric mixture was directly purified by preparative HPLC (Agilent 1100 Series, Chromolith prep RP-18e, 100-25). A colorless solid (110 mg, 0.35 mmol, 62%) was obtained, characterized as compound (iii).

In analogy to this procedure the following compounds of the invention were synthesized: compounds 2, 3, 5, 6, 8, 9, 12, 13, 14, 15, 16, 17, 22 and 28 to 33.

Alternative Synthesis:

b. 5-(3-Fluoro-phenyl)-2H-pyrazol-3-ylamine (i) (100 mg, 0.56 mmol) was dissolved in ethanol or isopropanol (1 mL), Ethyl-4,4,4-trifluoracetoacetat (0.12 mL, 0.84 mmol) was added at RT and the mixture was stirred for additional 4 h at reflux. The mixture was evaporated to dryness and directly purified by silica gel flash chromatography (Dichloromethane/Ethyl acetate). A colorless compound (iii) was obtained (92 mg, 0.29 mmol, 52%).

Example 2

3-(3-Methoxy-phenyl)-4-hydroxy-4-trifluoromethyl-1,4,5,7-tetrahydro-pyrazolo[3,4-b]pyridin-6-one

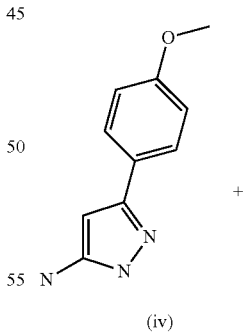

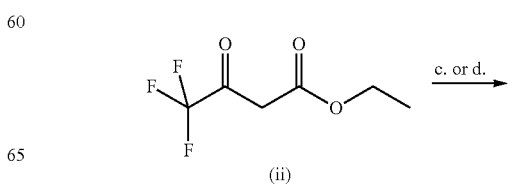

c=1.53 g/L in MeOH) and compound 21 (amount of rotation: $[\alpha]_D^{20}$=+32.0±3.1)(°) mL/(dm*g), c=1.65 g/L in MeOH)].

Example 4

4-Hydroxy-1-methyl-3-phenyl-4-trifluoromethyl-1,4,5,7-tetrahydro-pyrazolo[3,4-b]pyridin-6-one

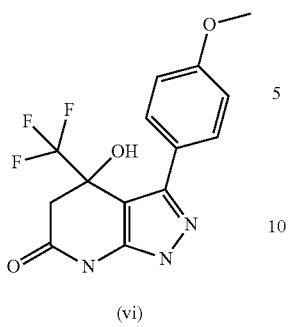

c. 5-(4-Methoxy-phenyl)-2H-pyrazol-3-ylamine (iv) (100 mg, 0.53 mmol) was dissolved in toluene (1 mL), Ethyl-4,4,4-trifluoracetoacetat (0.12 mL, 0.78 mmol) was added by RT and stirring was continued for 2.5 h at 120° C. The mixture was evaporated to dryness and directly purified by silica gel flash chromatography (Methanol/Dioxan). A colorless compound (vi) was obtained (72.5 mg, 0.22 mmol, 42).

d. 5-(4-Methoxy-phenyl)-2H-pyrazol-3-ylamine (iv) (100 mg, 0.53 mmol) and Ethyl-4,4,4-trifluoracetoacetat (0.12 mL, 0.78 mmol) was stirred without solvent for 2.5 h at 120° C. The mixture was evaporated to dryness and directly purified by silica gel flash chromatography (Methanol/Dioxan). A colorless solid (74.0 mg, 0.23 mmol, 43%) was obtained, characterized as compound (vi).

Example 3

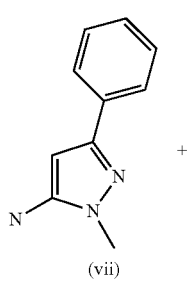

(iii)

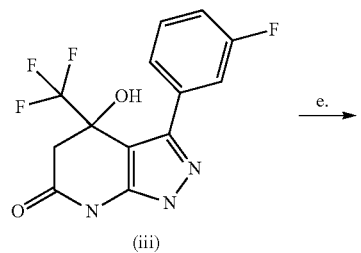

(iiia)     (iiib)

e. 50 mg of the racemic mixture (iii) was dissolved in ethanol (5 mL) and separated into enantiomers by chiral HPLC (column: 5×50 cm Chiralpak AD, 20 μm, flow rate: 120 mL/min, n-Heptan/Ethanol 70/30). Compounds (iiia) (21 mg) and (iiib) (22 mg) were obtained [compounds 20 (amount of rotation: $[\alpha]_D^{20}$=−31.53.3)(°) mL/(dm*g),

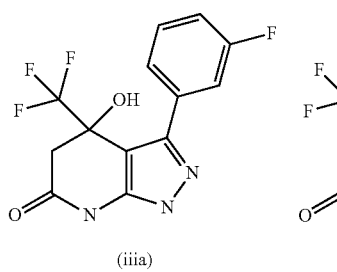

(vii)

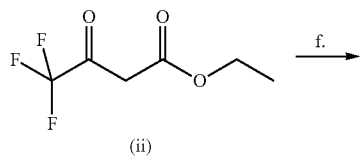

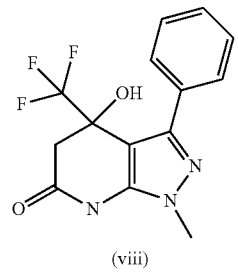

(viii)

f. 2-Methyl-5-phenyl-2H-pyrazol-3-ylamine (vii) (100 mg, 0.58 mmol) was dissolved in glacial acetic acid (1 mL), ethyl-4,4,4-trifluoracetoacetate (0.13 mL, 0.85 mmol) was added at RT and stirring was continued for 2.5 h at 120° C. The mixture was evaporated to dryness and the isomeric mixture was directly purified by preparative HPLC (Agilent 1100 Series, Chromolith prep RP-18e, 100-25). A colorless solid (29 mg, 0.09 mmol, 16%) was obtained, characterized as compound (viii).

In analogy to this procedure the following compounds of the invention were synthesized: compounds 4, 7, 18 and 19.

Example 5

4-Hydroxy-5-methoxy-3-phenyl-4-trifluoromethyl-1,4,5,7-tetrahydro-pyrazolo[3,4-b]pyridin-6-one

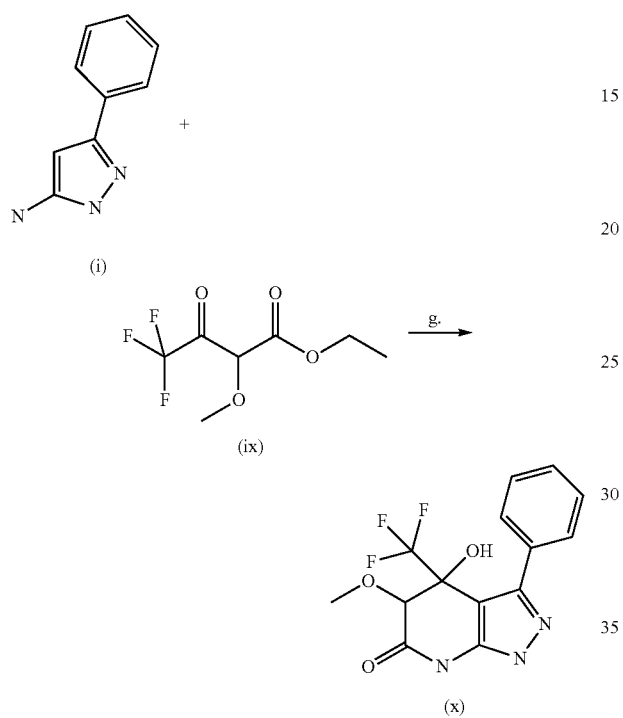

g. 5-Phenyl-2H-pyrazol-3-ylamine (i) (100 mg, 0.62 mmol) was dissolved in glacial acetic acid (1 mL), 4,4,4-Trifluoro-2-methoxy-3-oxo-butyric acid ethyl ester (95%, 0.17 mL, 0.92 mmol) was added at RT and stirring was continued for 15 h at 120° C. The mixture was evaporated to dryness and the isomeric mixture was directly purified by preparative HPLC (Agilent 1100 Series, Chromolith prep RP-18e, 100-25). A colorless solid (92 mg, 0.28 mmol, 46%) was obtained, characterized as compound (x).

In analogy to this procedure the following compounds of the invention were synthesized: compounds 24 to 27.

Example 6

4-Hydroxy-5-methoxy-3-phenyl-4-trifluoromethyl-1,4,5,7-tetrahydro-pyrazolo[3,4-b]pyridin-6-one

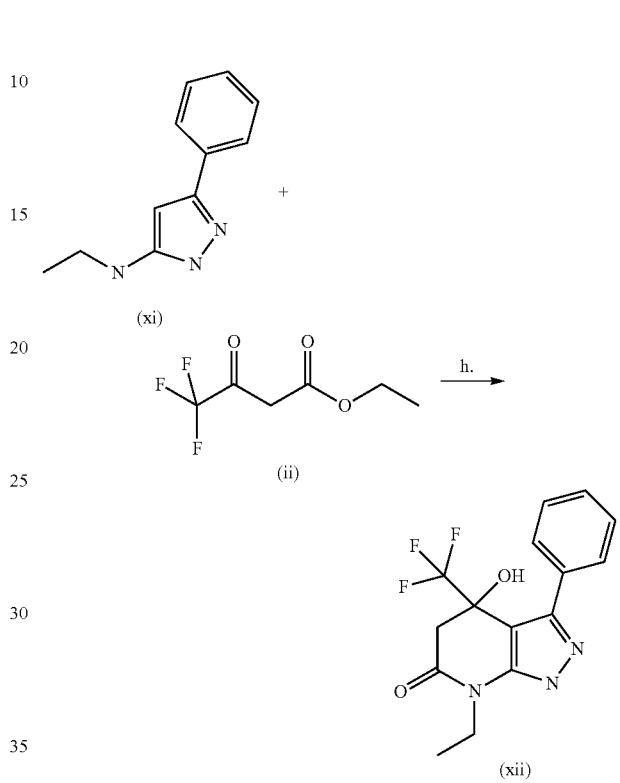

h. Ethyl-(5-phenyl-2H-pyrazol-3-yl)-amine (xi) (100 mg, 0.53 mmol, synthesized according to Journal of Heterocyclic Chemistry 1988, 25: 1387-90) was dissolved in glacial acetic acid (1 mL), Ethyl-4,4,4-trifluoracetoacetate (0.12 mL, 0.80 mmol) was added at RT and stirring was continued for 4 h at 120° C. The mixture was evaporated to dryness and directly purified by silica gel flash chromatography (Methanol/Dioxan). A colorless solid (113 mg, 0.35 mmol, 66%) was obtained, characterized as compound (xii).

II. Physicochemical Characterization of the Compounds of the Invention

TABLE 2

| Compound | Chemical name | MW [g/mol] | [M + 1]$^+$ | HPLC Rt [min]$^1$ | HPLC/ MS Rt [min]$^2$ | NMR or amount of rotation |
|---|---|---|---|---|---|---|
| 1 | 3-(3-Fluoro-phenyl)-4-hydroxy-4-trifluoromethyl-1,4,5,7-tetrahydro-pyrazolo[3,4-b]pyridin-6-one | 315.23 | 316 | 3.15 | 1.800 | $^1$H NMR (400 MHz, DMSO) δ 12.91 (s, 1H), 10.69 (s, 1H), 7.81-7.75 (m, 1H), 7.70 (d, J = 8.0, 1H), 7.49 (td, J = 8.1, 6.4, 1H), 7.24 (td, J = 8.3, 2.0, 1H) 7.12 (s, 1H), 3.01 (d, J = 16.5, 1H), 2.80 (J = 16.5, 1H). |

TABLE 2-continued

| Compound | Chemical name | MW [g/mol] | [M + 1]+ | HPLC Rt [min][1] | HPLC/ MS Rt [min][2] | NMR or amount of rotation |
|---|---|---|---|---|---|---|
| 2 | 4-Hydroxy-3-phenyl-4-trifluoromethyl-1,4,5,7-tetrahydro-pyrazolo[3,4-b]pyradin-6-one | 297.24 | 298 | | 1.618 | $^1$H NMR (300 MHz, DMSO) δ 12.75 (s, 1H), 10.63 (s, 1H), 7.84 (dd, J = 8.0, 1.5, 2H), 7.48-7.36 (m, 3H), 6.93 (s, 1H), 2.98 (d, J = 16.6, 1H), 2.79 (d, J = 16.5, 1H). |
| 3 | 4-Hydroxy-3-(4-methoxy-phenyl)-4-trifluoromethyl-1,4,5,7-tetrahydro-pyrazolo[3,4-b]pyradin-6-one | 327.26 | 328 | 3.04 | 1.764 | $^1$H NMR (400 MHz, DMSO) δ 12.64 (s, 1H), 10.62 (s, 1H), 7.80 (d, J = 8.9, 2H), 7.00 (d , J = 8.9, 2H) 6.95 (s, 1H), 3.79 (s, 3H), 2.97 (d, J = 16.5, 1H), 2.77 (d, J = 16.4, 1H). |
| 4 | 4-Hydroxy-1-methyl-3-phenyl-4-trifluoromethyl-1,4,5,7-tetrahydro-pyrazolo[3,4-b]pyridin-6-one | 311.26 | 312 | 3.15 | 1.822 | $^1$H NMR (400 MHz, DMSO) δ 11.05 (s, 1H), 7.99-7.95 (m, 2H), 7.38-7.26 (m, 3H), 7.01 (s, 1H), 3.74 (s, 3H), 3.06 (d, J = 16.3, 1H), 2.82 (d, J = 16.4, 1H). |
| 5 | 3-(4-Chloro-phenyl)-4-hydroxy-4-trifluoromethyl-1,4,5,7-tetrahydro-pyrazolo[3,4-b]pyridin-6-one | 331.68 | 333 | 3.41 | 1.926 | $^1$H NMR (400 MHz, DMSO) δ 12.85 (s, 1H), 10.68 (s, 1H), 7.87 (d, J = 8.6, 2H), 7.52 (d, J = 8.6, 2H), 7.05 (s, 1H), 2.99 ( d, J = 16.6, 1H), 2.79 (d, J = 16.5, 1H). |
| 6 | 4-Hydroxy-3-p-tolyl-4-trifluoromethyl-1,4,5,7-tetrahydro-pyrazolo[3,4-b]pyridin-6-one | 311.26 | 312 | 3.23 | 1.855 | $^1$H NMR (400 MHz, DMSO) δ 12.68 (s, 1H), 10.62 (s, 1H), 7.74 (d, J = 8.1, 2H), 7.24 (d, J = 8.1, 2H), 6.92 (s, 1H), 2.97 (d, J = 16.5, 1H) 2.77 (d, J = 16.4, 1H), 2.33 (s, 3H). |
| 7 | 4-Hydroxy-1-methyl-3-thiophen-2-yl-4-trifluoromethyl-1,4,5,7-tetrahydro-pyrazolo[3,4-b]pyridin-6-one | 317.29 | 318 | 3.12 | 1.816 | |
| 8 | 4-Hydroxy-3-thiophen-2-yl-4-trifluoromethyl-1,4,5,7-tetrahydro-pyrazolo[3,4-b]pyridin-6-one | 303.26 | 304 | 2.75 | 1.672 | $^1$H NMR (400 MHz, DMSO) δ 12.85 (s, 1H), 10.64 (s, 1H), 7.69-7.59 (m, 2H), 7.14-7.10 (s, 1H), 7.01 (s, 1H), 2.99 (d, J = 16.4, 1H), 2.76 (d, J = 16.4, 1H). |
| 9 | 3-(3,5-Dimethoxy-phenyl)-4-hydroxy-4-trifluoromethyl- | 357.29 | 358 | 3.25 | 1.822 | $^1$H NMR (400 MHz, DMSO) δ 12.79 (s, 1H), 10.65 (s, 1H), 7.13 (d, J = 2.2, 2H), |

TABLE 2-continued

| Compound | Chemical name | MW [g/mol] | [M + 1]+ | HPLC Rt [min][1] | HPLC/ MS Rt [min][2] | NMR or amount of rotation |
|---|---|---|---|---|---|---|
|  | 1,4,5,7-tetrahydro-pyrazolo[3,4-b]pyridin-6-one |  |  |  |  | 7.06 (s, 1H), 6.53 (t, J = 2.2, 1H), 3.77 (s, 6H), 2.99 (d, J = 16.6, 1H), 2.79 (d, J = 16.4, 1H). |
| 10 | (S)-4-Hydroxy-3-phenyl-4-trifluoromethyl-1,4,5,7-tetrahydro-pyrazolo[3,4-b]pyridin-6-one | 297.24 | 298 | 2.93 | 1.721 | Amount of rotation: $[\alpha]_D^{20} = -26.0 \pm 1.9$ (°) mL/(dm*g), c = 2.70 g/L in MeOH |
| 11 | (R)-4-Hydroxy-3-phenyl-4-trifluoromethyl-1,4,5,7-tetrahydro-pyrazolo[3,4-b]pyridin-6-one | 297.24 | 298 | 2.91 | 1.723 | Amount of rotation: $[\alpha]_D^{20} = +26.0 \pm 2.2$ (°) mL/(dm*g), c = 2.85 g/L in MeOH |
| 12 | 3-(4-Bromo-phenyl)-4-hydroxy-4-trifluoromethyl-1,4,5,7-tetrahydro-pyrazolo[3,4-b]pyridin-6-one | 376.13 | 376, 378 | 3.39 | 1.901 |  |
| 13 | 3-(3-Bromo-phenyl)-4-hydroxy-4-trifluoromethyl-1,4,5,7-tetrahydro-pyrrazolo[3,4-b]pyridin-6-one | 376.13 | 376, 378 | 3.36 | 1.870 | $^1$H NMR (400 MHz, DMSO) δ 12.92 (s, 1H), 10.71 (s, 1H), 8.12 (t, J = 1.7, 1H), 7.85 (d, J = 8.1, 1H) 7.61 (dd, J = 8.0, 1.0, 1H), 7.42 (t, J = 7.9, 1H), 7.13 (s, 1H), 3.00 (d, J = 16.6, 1H), 2.79 (d, J = 16.4, 1H). |
| 14 | 3-(3-Chloro-phenyl)-4-hydroxy-4-trifluoromethyl-1,4,5,7-tetrahydro-pyrazolo[3,4-b]pyridin-6-one | 331.68 | 333 | 3.28 | 1.838 | $^1$H NMR (400 MHz, DMSO) δ 12.93 (s, 1H), 10.72 (s, 1H), 7.99 (s, 1H), 7.84-7.78 (m, 1H), 7.51-7.47 (m, 2H), 7.15 (s, 1H), 3.01 (d, J = 16.5, 1H), 2.80 (d, J = 16.5, 1H). |
| 15 | 4-Hydroxy-4-trifluoromethyl-3-(3-trifluoromethyl-phenyl)-1,4,5,7-tetrahydro-pyrazolo[3,4-b]pyridin-6-one | 365.23 | 366 | 3.49 | 1.947 | $^1$H NMR (400 MHz, DMSO) δ 13.04 (s, 1H), 10.75 (s, 1H), 8.34 (s, 1H), 8.14 (d, J = 7.9, 1H), 7.78 (d, J = 7.8, 1H) 7.71 (t, J = 7.8, 1H), 7.21 (s, 1H), 3.03 (d, J = 16.6, 1H), 2.81 (d, J = 16.4, 1H). |
| 16 | 3-Cyclopropyl-4-hydroxy-4-trifluoromethyl-1,4,5,7-tetrahydro-pyrazolo[3,4- | 261.20 | 262 | 1.84 | 1.455 |  |

TABLE 2-continued

| Compound | Chemical name | MW [g/mol] | [M + 1]+ | HPLC Rt [min][1] | HPLC/ MS Rt [min][2] | NMR or amount of rotation |
|---|---|---|---|---|---|---|
| 17 | b]pyridin-6-one<br>3-(4-Fluoro-phenyl)-4-hydroxy-4-trifluoromethyl-1,4,5,7-tetrahydro-pyrazolo[3,4-b]pyridin-6-one | 315.23 | 316 | 2.99 | 1.804 | $^1$H NMR (400 MHz, DMSO) δ 12.80 (s, 1H), 10.67 (s, 1H), 7.91-7.85 (m, 2H), 7.33-7.27 (m, 2H), 7.03 (s, 1H), 2.98 (d, J = 16.4, 1H), 2.79 (d, J = 16.4, 1H). |
| 18 | 3-(4-Chloro-phenyl)-4-hydroxy-1-methyl-4-trifluoromethyl-1,4,5,7-tetrahydro-pyrazolo[3,4-b]pyradin-6-one | 345.71 | 347 | 3.63 | 2.068 | |
| 19 | 4-Hydroxy-1,3-diphenyl-4-trifluoromethyl-1,4,5,7-tetrahydro-pyrazolo[3,4-b]pyridin-6-one | 373.33 | 374 | 3.95 | 2.205 | |
| 20 | (S)-3-(3-Fluoro-phenyl)-4-hydroxy-4-trifluoromethyl-1,4,5,7-tetrahydro-pyrazolo[3,4-b]pyridin-6-one | 315.23 | 316 | 2.96 | 1.812 | Amount of rotation: $[\alpha]_D^{20} = -31.5 \pm 3.3$ (°) mL/(dm*g), c = 1.53 g/L in MeOH |
| 21 | (R)-3-(3-Fluoro-phenyl)-4-hydroxy-4-trifluoromethyl-1,4,5,7-tetrahydro-pyrazolo[3,4-b]pyridin-6-one | 315.23 | 316 | 2.99 | 1.811 | Amount of rotation: $[\alpha]_D^{20} = +32.0 \pm 3.1$ (°) mL/(dm*g), c = 1.65 g/L in MeOH |
| 22 | 4-Hydroxy-3-pyridin-4-yl-4-trifluoromethyl-1,4,5,7-tetrahydro-pyrazolo[3,4-b]pyridin-6-one | 298.22 | 299 | | 1.267 | $^1$H NMR (400 MHz, DMSO) δ 13.17 (s, 1H), 10.76 (s, 1H), 8.66 (d, J = 5.8, 2H), 7.91 (d, J = 5.8, 2H), 7.25 (s, 1H), 3.05 (d, J = 16.6, 1H), 2.83 (d, J = 16.5, 1H). |
| 23 | 4-Hydroxy-7-ethyl-3-phenyl-4-trifluoromethyl-1,4,5,7-tetrahydro-pyrazolo[3,4-b]pyridin-6-one | 325.29 | 326 | | 1.896 | |
| 24 | 4-Hydroxy-5-methyl-3-phenyl-4-trifluoromethyl-1,4,5,7-tetrahydro- | 311.27 | 312 | 2.83<br>3.01 | 1.76<br>1.81 | |

TABLE 2-continued

| Compound | Chemical name | MW [g/mol] | [M + 1]+ | HPLC Rt [min]1 | HPLC/MS Rt [min]2 | NMR or amount of rotation |
|---|---|---|---|---|---|---|
| | pyrazolo[3,4-b]pyridin-6-one | | | | | |
| 25 | 4-Hydroxy-5-ethyl-3-phenyl-4-trifluoromethyl-1,4,5,7-tetrahydro-pyrazolo[3,4-b]pyridin-6-one | 325.29 | 326 | 3.15 | 1.81 | 1H NMR (400 MHZ, DMSO, one diastereomer) δ 12.67 (s, 1H), 10.42 (s, 1H), 7.93-7.77 (m, 2H), 7.52-7.31 (m, 3H), 6.67 (s, 1H), 2.50-2.46 (m, 2H, covered by DMSO-signal), 2.05-1.93 (m, 1H), 1.37-1.26 (m, 1H), 0.91 (t, J = 7.8, 3H). |
| 26 | 4-Hydroxy-5-(2-hydroxy-ethyl)-3-phenyl-4-trifluoromethyl-1,4,5,7-tetrahydro-pyrazolo[3,4-b]pyridin-6-one | 341.29 | 342 | 2.64 | 1.7 | 1H NMR (400 MHz, DMSO, d-TFA exchanged) δ 7.91-7.80 (m, 2H), 7.55-7.38 (m, 3H), 3.69-3.52 (m, 2H), 2.87 (dd, J = 9.3, 4.5, 1H), 2.28-2.17 (m, 1H), 1.65-1.55 (m, 1H). |
| 27 | 4-Hydroxy-5-methoxy-3-phenyl-4-trifluoromethyl-1,4,5,7-tetrahydro-pyrazolo[3,4-b]pyridin-6-one | 327.27 | 328 | 3.09 | 1.79 | 1H NMR (400 MHz, DMSO, d-TFA exchanged) δ 7.91-7.87 (m, 2H), 7.50-7.38 (m, 3H), 3.70 (s, 1H), 3.52 (s, 3H). |
| 28 | 3-Benzyl-4-hydroxy-4-trifluoromethyl-1,4,5,7-tetrahydro-pyrazolo[3,4-b]pyridin-6-one | 311.27 | 312 | 3.04 | 1.81 | |
| 29 | 4-Hydroxy-3-(1H-indol-3-yl)-4-trifluoromethyl-1,4,5,7-tetrahydro-pyrazolo[3,4-b]pyridin-6-one | 336.27 | 337 | 2.72 | 1.72 | 1H NMR (400 MHz, DMSO) δ 12.39 (s, 1H), 11.40 (s, 1H), 10.57 (s, 1H), 7.84 (d, J = 2.7, 1H), 7.77 (d, J = 8.0 1H), 7.45 (d, J = 8.0, 1H), 7.18-7.13 (m, 1H), 7.11-7.06 (m, 1H), 6.81 (s, 1H), 2.96 (d, J = 16.5, 1H), 2.78 (d, J = 16.3, 1H). |
| 30 | 3-Furan-2-yl-4-hydroxy-4-trifluoromethyl-1,4,5,7-tetrahydro-pyrazolo[3,4-b]pyridin-6-one | 287.2 | 288 | 2.37 | 1.66 | 1H NMR (500 MHz, DMSO) δ 12.98 (s, 1H), 10.65 (s, 1H), 7.79 (d, J = 1.3, 1H), 7.07 (d, J = 3.4, 1H), 7.00 (s, 1H), 6.62 (dd, J = 3.4, 1.8, 1H), 2.98 (d, J = 16.5, 1H), 2.78 (d, J = 16.4, 1H). |
| 31 | 3-(3,4-Dimethoxy-phenyl)-4-hydroxy-4-trifluoromethyl-1,4,5,7- | 357.29 | 358 | 3.77 | 1.69 | 1H NMR (400 MHz, DMSO) δ 12.66 (s, 1H), 10.60 (s, 1H), 7.58 (d, J = 2.0, 1H), 7.44 (dd, J = 8.4, |

TABLE 2-continued

| Compound | Chemical name | MW [g/mol] | [M + 1]+ | HPLC Rt [min][1] | HPLC/ MS Rt [min][2] | NMR or amount of rotation |
|---|---|---|---|---|---|---|
| | tetrahydro-pyrazolo[3,4-b]pyridin-6-one | | | | | 2.1, 1H), 7.07 (s, 1H), 7.01 (d, J = 8.4, 1H) 3.78 (d, J = 8.5, 6H), 2.98 (d, J = 16.5, 1H), 2.80 (d, J = 16.5, 1H). |
| 32 | 4-Hydroxy-3-(3-methoxy-phenyl)-4-trifluoromethyl-1,4,5,7-tetrahydro-pyrazolo[3,4-b]pyridin-6-one | 327.26 | 328 | 2.69 | 1.75 | |
| 33 | 3-(1,5-Dimethyl-1H-pyrazol-4-yl)-4-hydroxy-4-trifluoromethyl-1,4,5,7-tetrahydro-pyrazolo[3,4-b]pyridin-6-one | 315.25 | 316 | 2.61 | 1.49 | $^1$H NMR (400 MHz, DMSO) δ 12.28 (s, 1H), 10.59 (s, 1H), 7.53 (s, 1H), 6.63 (s, 1H), 3.76 (s, 3H), 2.89 (d, J = 16.4, 1H), 2.75 (d, J = 16.4, 1H), 2.24 (s, 3H). |
| 34 | 7-Ethyl-4-hydroxy-3-phenyl-4-trifluoromethyl-1,4,5,7-tetrahydro-pyrazolo[3,4-b]pyridin-6-one | 325.29 | 326 | 3.31 | 1.94 | |
| 35 | 4-(3,5-Bis-trifluoromethyl-phenyl)-4-hydroxy-3-phenyl-1,4,5,7-tetrahydro-pyrazolo[3,4-b]pyridin-6-one | 441.33 | 442 | 4.29 | 2.37 | |

[1]HPLC-Method (nonpolar)

Solvent A: Water + 0.1% TFA

Solvent B: Acetonitrile + 0.08% TFA

Flow: 1.5 ml/min

Gradient: 0.0 min 20% B 5.0 min 100% B 5.5 min 100% B 6.0 min 20% B 6.5 min 20% B Column: Chromolith Performance RP18e 100-3

[2] HPLC/MS-Method (polar)

Solvent A: Water + 0.05% Formic Acid

Solvent B: Acetonitrile + 0.04% Formic Acid

Flow: 2.4 ml/min, wavelength: 220 nm

Gradient: 0.0 min 4% B 2.8 min 100% B 3.3 min 100% B 3.4 min 4% B

Column: Chromolith ® Speed ROD RP-18e 50-4.6 mm

III. Biological Assays

Description of the LPA2R Assay
Reagents
Cell Culture

| | |
|---|---|
| cell linie | U2OS, recombinant expressing LPA2R |
| McCoy's Medium | Invitrogen # 26600-021 |
| DMEM | Gibco #41965 |
| Penicillin/Streptomyci | Gibco #15140 |
| FCS | PAA # A15-043 |
| Geniticin | Invitrogen #10131-027 |
| PBS | Gibco |
| HEPES | Gibco #15630-056 |
| HyQ-Tase | HyClone #SV30030.01 |

Assay

| | |
|---|---|
| 10 x HBSS | Gibco #14065 |
| 1M HEPES | Merck #1.10110 |
| NaCl | Merck #1.06404 |
| KCl | Merck #1.04936 |
| $MgSO_4 \times 7H_2O$ | Merck #1.05886 |
| $CaCl_2 \times 2H_2O$ | Merck #1.02382 |
| $D(+)$-Glucose $\times 1H_2O$ | Merck #1.04074 |
| BSA, fatty acid free | Roche #10 77 58 35 001 |
| ligand (LPA), 1-Oleoyl-2-Hydroxy-sn-Glycero-3-Phosphate, Avanti #857130P | |
| probenecid, water soluble | Invitrogen #P36400 |
| detection solution (calcium dye) | Bulk Kit (Mol. Dev. #R8141) |
| mikro plate 384 blck, cl. bottom | Falcon # 353692 |

Cell Cultivation/Propagation

| | |
|---|---|
| medium | McCoy's Medium, 10% FCS, 1 mg/ml Geniticin |
| culture conditions | 37° C., 5% $CO_2$ in T75 flasks |
| harvesting | washing with PBS |
| | detaching with 1 mL HyQ-Tase per flask |
| | incubation 5 min |
| | addition of 10 mL medium |
| | centrifugation |
| | re-suspension with 10 mL culture medium |

LPA2R-calciumflux Assay Protocol

The assay detects intra cellular calcium which is generated by cells upon activation of the LPA2 receptor by its ligand LPA. This transient calcium mobilisation can be monitored using a commercial calcium detection kit (e.g. from Molecular Devices). The main component of such a kit is a dye, which becomes fluorescent when calcium is present—a transient fluorescence signal after laddition of a ligand to a test well are the result. Readers like the FLIPR (from Molecular Devices) can be used to monitor such transient "Ca-flux" signals.

The signals are calculated according to peak maximum minus base line. Compounds which are antogonists of LPA lead to a decreased mobilisation of intracellular calcium and thus to a lower signal. The assay is performed in microplates (384 wells per plate).

The assay itself is run according to the following procedure:

50 uL seed cells (10000 cells/well in DMEM buffer)
  Incubate 24 h at 37° C., 10% $CO_2$
  aspirate medium
50 uL add calcium dye 1×HBSS/HEPES buffer
  incubate 1 h at 37° C. ("loading")
  equilibrate 10 min at RT
5 uL add compounds in HEPES buffer
  shake 10 sec. @ 1000 rpm
  incubate 15 min at RT
20 uL add LPA (in the FLIPR Tetra) in KREBS-Puffer/BSA
  & measurement The cells are seeded in DMEM buffer (DMEM, 10% FCS, 10 mM HEPES, 1% Pen/Strep).

Dye loading is done in HBSS/HEPES buffer (100 mL 10×HBSS+20 mL 1M HEPES+880 mL water, pH 7.4)

The LPA is added in Krebs/BSA buffer (120 mM NaCl, 5 mM KCl, 0.62 mM $MgSO_4$, 1.8 mM $CaCl_2$, 10 mM HEPES, 6 mM D(+)-Glucose, 0.2% BSA, pH 7.4).

The compounds are pre-diluted in HEPES buffer (20 mM, pH 7.4), whereby the final DMSO content in the assay is kept at 1%. The compounds are pre-diluted in order to generate dose response series on the microplates. The dose response series consist of 10 concentrations for each compound from 30 uM final to 1 nM final. From all compound wells the resulting signals are referred to control wells (located on each plate besides the compound wells) in terms of % activity.

$$\% \text{ activity} = \frac{(readout_{compoupd} - readout_{blank})}{(readout_{full} - readout_{blank})} * 100$$

From these % activity values—along with the corresponding compound concentrations—IC50 values are fitted for each compound using standard fitting programs such as Graphpad Prism. Here the method "log(inhibitor) vs. response—Variable slope" is used.

Reader Settings (FLIPR Tetra)
ExcWLength:470__495
Em.Wlength: 515__575
Gain: 50
Exp. Time: 0,4
Exc.Intensity: 80
READ with TF
First read interval: 1,00 s
Number of first reads: 240
Reads before dispense: 10
Second read interval: 1,00 s
Number of second reads: 0
Save Images No

TABLE 3

| Compound | IC50<br>A = >10 μM<br>B = 1-10 μM<br>C = <1 μM |
|---|---|
| 1 | C |
| 2 | C |
| 3 | C |
| 4 | A |
| 5 | B |
| 6 | C |
| 7 | A |
| 8 | C |
| 9 | C |
| 10 | C |
| 11 | A |
| 12 | A |
| 13 | C |
| 14 | C |
| 15 | C |
| 16 | A |
| 17 | C |
| 18 | A |
| 19 | A |

TABLE 3-continued

| Compound | IC50<br>A = >10 μM<br>B = 1-10 μM<br>C = <1 μM |
|---|---|
| 20 | C |
| 21 | A |
| 22 | C |
| 23 |   |
| 24 | B |
| 25 | A |
| 26 | A |
| 27 | A |
| 28 | A |
| 29 | A |
| 30 | A |
| 31 | C |
| 32 | B |
| 33 | B |
| 34 | A |
| 35 | A |

The invention claimed is:

1. A method for modulating an LPA receptor 2, said method comprising modulating said receptor with a compound according to formula (I):

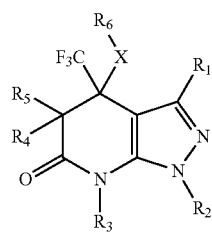

wherein:
R$_1$ denotes aryl, heteroaryl, cycloalkyl, heterocyclyl, arylalkyl, heteroarylalkyl, cycloalkylalkyl or heterocyclylalkyl, which in each case is unsubstituted or substituted with one or more substituents selected from alkyl, cycloalkyl, cycloalkylalkyl, heterocyclyl, heterocyclylalkyl, aryl, arylalkyl, heteroaryl, heteroarylalkyl, halogen, —F, —Cl, —Br, —I, —CN, —CF$_3$, —N$_3$, —NH$_2$, —NHZ1, —NZ2Z3, —NO$_2$, —OH, —OCF$_3$, —SH, —O—SO$_3$H, —OP(O)(OH)$_2$, —CHO, —COOH, —C(O)NH$_2$, —SO$_3$H, —P(O)(OH)$_2$, —C(O)—Z4, —C(O)O—Z5, —C(O)NH—Z6, —C(O)NZ7Z8, —O—Z9, —O(—Z10—O)$_a$—H, —O(—Z11—O)$_b$—Z12, —OC(O)—Z13, —OC(O)—O—Z14, —OC(O)—NHZ15, —O—C(O)—NZ16Z17, —OP(O)(OZ18)(OZ19), —OSi(Z20)(Z21)(Z22), —OS(O$_2$)—Z23, —NHC(O)—NH$_2$, —NHC(O)—Z24, —NZ25C(O)—Z26, —NH—C(O)—O—Z27, —NH—C(O)—NH—Z28, —NH—C(O)—NZ29Z30, —NZ31—C(O)—O—Z32, —NZ33—C(O)—NH—Z34, —NZ35—C(O)—NZ36Z37, —NHS(O$_2$)—Z38, —NZ39S(O$_2$)—Z40, —S—Z41, —S(O)—Z42, —S(O$_2$)—Z43, —S(O$_2$)NH—Z44, —S(O$_2$)NZ45Z46, —S(O$_2$)O—Z47, —P(O)(OZ48)(OZ49), —Si(Z50)(Z51)(Z52), —C(NH)—NH$_2$, —C(NZ53)—NH$_2$, —C(NH)—NHZ54, —C(NH)—NZ55Z56, —C(NZ57)—NHZ58, —C(NZ59)—NZ60Z61, —NH—C(O)—NH—O—Z62, —NH—C(O)—NZ63—O—Z64, —NZ65—C(O)—NZ66—O—Z67, —N(—C(O)—NH—O—Z68)$_2$, —N(—C(O)—NZ69—O—Z70)$_2$, —N(—C(O)—NH—O—Z71)(—C(O)—NZ72—O—Z73), —C(S)—Z74, —C(S)—O—Z75, —C(S)—NH—Z76, —C(S)—NZ77Z78, —C(O)—NH—O—Z79, —C(O)—NZ80—O—Z81, —C(S)—NH—O—Z82, —C(S)—NZ83—O—Z84, —C(O)—NH—NH—Z85, —C(O)—NH—NZ86Z87, —C(O)—NZ88—NZ89Z90, —C(S)—NH—NH—Z91, —C(S)—NH—NZ92Z93, —C(S)—NZ94—NZ95Z96, —C(O)—C(O)—O—Z97, —C(O)—C(O)—NH$_2$, —C(O)—C(O)—NHZ98, —C(O)—C(O)—NZ99Z100, —C(S)—C(O)—O—Z101, —C(O)—C(S)—O—Z102, —C(S)—C(S)—O—Z103, —C(S)—C(O)—NH$_2$, —C(S)—C(O)—NHZ104, —C(S)—C(O)—NZ105Z106, —C(S)—C(S)—NH$_2$, —C(S)—C(S)—NHZ107, —C(S)—C(S)—NZ108Z109, —C(O)—C(S)—NH$_2$, —C(O)—C(S)—NHZ110, —C(O)—C(S)—NZ111Z112;

Z1, Z2, Z3, Z4, Z5, Z6, Z7, Z8, Z9, Z10, Z11, Z12, Z13, Z14, Z15, Z16, Z17, Z18, Z19, Z20, Z21, Z22, Z23, Z24, Z25, Z26, Z27, Z28, Z29, Z30, Z31, Z32, Z33, Z34, Z35, Z36, Z37, Z38, Z39, Z40, Z41, Z42, Z43, Z44, Z45, Z46, Z47, Z48, Z49, Z50, Z51, Z52, Z53, Z54, Z55, Z56, Z57, Z58, Z59, Z60, Z61, Z62, Z63, Z64, Z65, Z66, Z67, Z68, Z69, Z70, Z71, Z72, Z73, Z74, Z75, Z76, Z77, Z78, Z79, Z80, Z81, Z82, Z83, Z84, Z85, Z86, Z87, Z88, Z89, Z90, Z91, Z92, Z93, Z94, Z95, Z96, Z97, Z98, Z99, Z100, Z101, Z102, Z103, Z104, Z105, Z106, Z107, Z108, Z109, Z110, Z111, Z112 are each, independently from each other, selected from alkyl, cycloalkyl, cycloalkylalkyl, heterocyclyl, heterocyclylalkyl, aryl, arylalkyl, heteroaryl, and heteroarylalkyl, and wherein alternatively Z7, Z8 and/or Z16, Z17 and/or Z29, Z30 and/or Z36, Z37 and/or Z45, Z46 and/or Z55, Z56 and/or Z60, Z61 and/or Z77, Z78 and/or Z86, Z87 and/or Z89, Z90 and/or Z92, Z93 and/or Z95, Z96 and/or Z99, Z100 and/or Z105, Z106 and/or Z108, Z109 and/or Z111, Z112 can each, respectively, together form a heterocyclyl;

a is 1, 2, 3, 4, or 5;
b is 1, 2, 3, 4, or 5;
R$_2$ denotes H or alkyl;
R$_3$ denotes H or alkyl;
R$_4$, R$_5$ independently from each other denote H, alkyl, OH-alkyl, alkoxy, halogen, F, Cl, Br, I, CN, NHR, NH$_2$, NR$_2$, S-alkyl or NH-alkyl-OH;
R independently from each other denotes alkyl, aryl, heteroaryl, cycloalkyl or heterocyclyl;
R$_4$ and R$_5$ together can also form cycloalkyl or heterocyclyl;
R$_6$ denotes H;
X denotes O;
and the physiologically acceptable salts, tautomers and stereoisomers thereof, including mixtures thereof in all ratios, with the proviso that the following compound is excluded from formula (I):

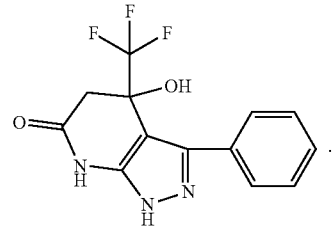 [SMILES: O=C1CC(O)(C(F)(F)F)c2c(-c3ccccc3)n[nH]c2N1]

2. A method according to claim 1, wherein LPA receptor activity is inhibited with said compound according to formula I.

3. A method according to claim 1, wherein R$_1$ denotes aryl, heteroaryl, cycloalkyl or arylalkyl, which in each case is unsubstituted or substituted with one or more substituents selected from halogen, F, Cl, Br, I, CF₃, alkyl, methyl, alkoxy and methoxy.

4. A method according to claim 1, wherein R₂ denotes H, methyl or ethyl.

5. A method according to claim 1, wherein R₃ denotes H, methyl or ethyl.

6. A method according to claim 1, wherein R₄ and R₅ independently from each other denote H, alkyl, OH-alkyl, alkoxy, methyl, ethyl, hydroxy-ethyl or methoxy.

7. A method according to claim 1, wherein
R₁ denotes aryl, heteroaryl, cycloalkyl or arylalkyl, which is unsubstituted or substituted with one or more substituents selected from halogen, F, Cl, Br, I, CF₃, alkyl, methyl, alkoxy and methoxy,
R₂ denotes H, methyl or ethyl,
R₃ denotes H, methyl or ethyl, and
R₄, R₅ independently from each other denote H, alkyl, OH-alkyl, alkoxy, methyl, ethyl, hydroxy-ethyl or methoxy.

8. A method according to claim 3, wherein R₁ is phenyl, thiophenyl, furanyl, pyrazolyl, pyridinyl, indolyl or benzyl, which in each case is unsubstituted or substituted with one or more substituents selected from halogen, F, Cl, Br, I, CF₃, alkyl, methyl, alkoxy and methoxy.

9. A method according to claim 7, wherein R₁ is phenyl, thiophenyl or benzyl, which is unsubstituted or substituted with one or more substituents selected from halogen, F, Cl, Br, I, CF₃, alkyl, methyl, alkoxy and methoxy.

10. A method according to claim 7, wherein R₁ is phenyl, thiophenyl, furanyl, pyrazolyl, pyridinyl, indolyl or benzyl, which in each case is unsubstituted or substituted with one or more substituents selected from halogen, F, Cl, Br, I, CF₃, alkyl, methyl, alkoxy and methoxy.

11. A method according to claim 1, wherein said compound is selected from:

| | | |
|---|---|---|
| 1 | 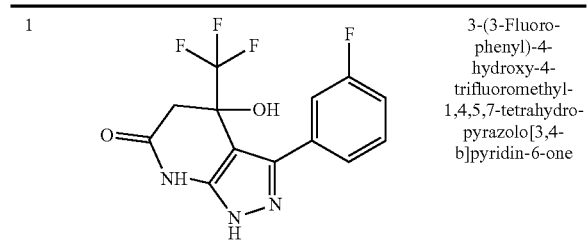 | 3-(3-Fluoro-phenyl)-4-hydroxy-4-trifluoromethyl-1,4,5,7-tetrahydro-pyrazolo[3,4-b]pyridin-6-one |
| 3 | 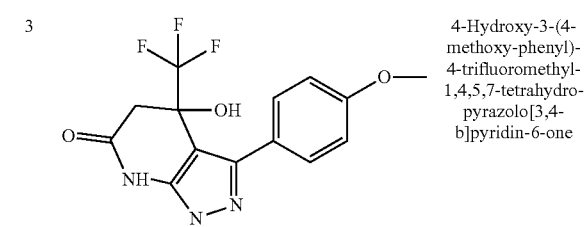 | 4-Hydroxy-3-(4-methoxy-phenyl)-4-trifluoromethyl-1,4,5,7-tetrahydro-pyrazolo[3,4-b]pyridin-6-one |
| 4 | 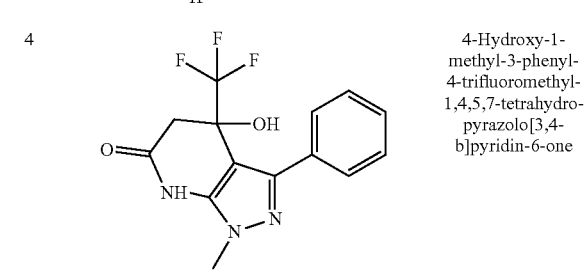 | 4-Hydroxy-1-methyl-3-phenyl-4-trifluoromethyl-1,4,5,7-tetrahydro-pyrazolo[3,4-b]pyridin-6-one |
| 5 | 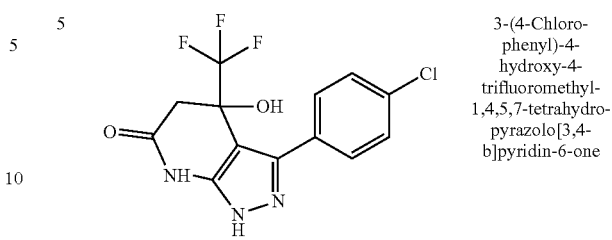 | 3-(4-Chloro-phenyl)-4-hydroxy-4-trifluoromethyl-1,4,5,7-tetrahydro-pyrazolo[3,4-b]pyridin-6-one |
| 6 | 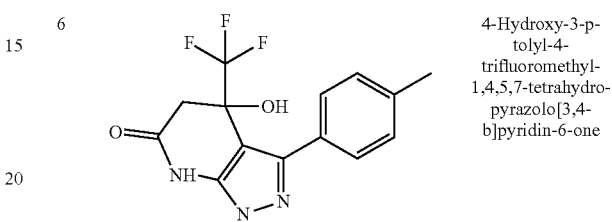 | 4-Hydroxy-3-p-tolyl-4-trifluoromethyl-1,4,5,7-tetrahydro-pyrazolo[3,4-b]pyridin-6-one |
| 7 | 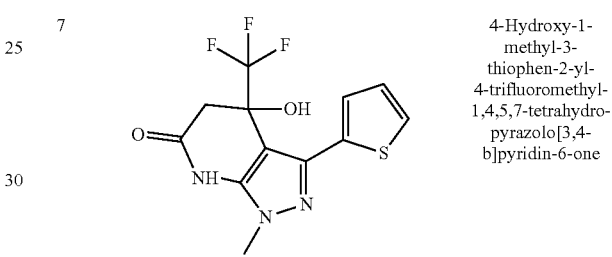 | 4-Hydroxy-1-methyl-3-thiophen-2-yl-4-trifluoromethyl-1,4,5,7-tetrahydro-pyrazolo[3,4-b]pyridin-6-one |
| 8 | 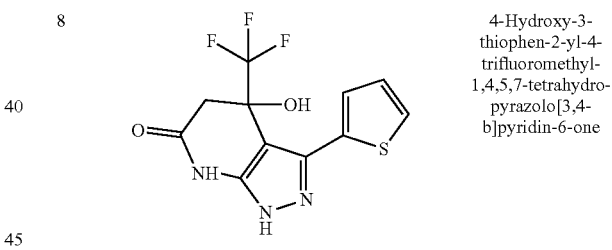 | 4-Hydroxy-3-thiophen-2-yl-4-trifluoromethyl-1,4,5,7-tetrahydro-pyrazolo[3,4-b]pyridin-6-one |
| 9 | 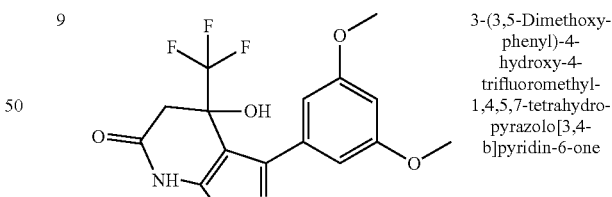 | 3-(3,5-Dimethoxy-phenyl)-4-hydroxy-4-trifluoromethyl-1,4,5,7-tetrahydro-pyrazolo[3,4-b]pyridin-6-one |
| 12 | 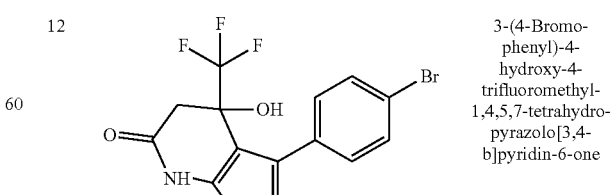 | 3-(4-Bromo-phenyl)-4-hydroxy-4-trifluoromethyl-1,4,5,7-tetrahydro-pyrazolo[3,4-b]pyridin-6-one |

| | | |
|---|---|---|
| 13 | 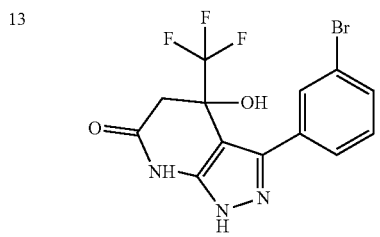 | 3-(3-Bromo-phenyl)-4-hydroxy-4-trifluoromethyl-1,4,5,7-tetrahydro-pyrazolo[3,4-b]pyridin-6-one |
| 14 | 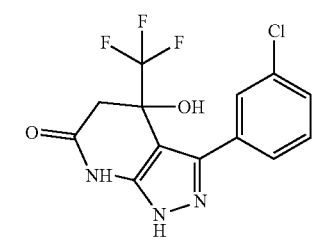 [SMILES: O=C1CC(O)(C(F)(F)F)c2c(-c3cccc(Cl)c3)n[nH]c2N1] | 3-(3-Chloro-phenyl)-4-hydroxy-4-trifluoromethyl-1,4,5,7-tetrahydro-pyrazolo[3,4-b]pyridin-6-one |
| 15 | 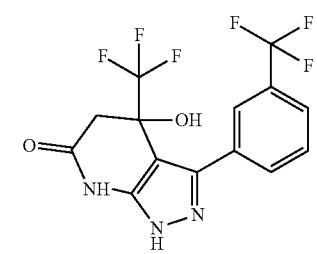 [SMILES: O=C1CC(O)(C(F)(F)F)c2c(-c3cccc(C(F)(F)F)c3)n[nH]c2N1] | 4-Hydroxy-4-trifluoromethyl-3-(3-trifluoromethyl-phenyl)-1,4,5,7-tetrahydro-pyrazolo[3,4-b]pyridin-6-one |
| 16 | 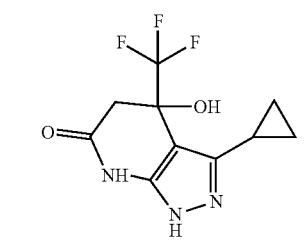 [SMILES: O=C1CC(O)(C(F)(F)F)c2c(C3CC3)n[nH]c2N1] | 3-Cyclopropyl-4-hydroxy-4-trifluoromethyl-1,4,5,7-tetrahydro-pyrazolo[3,4-b]pyridin-6-one |
| 17 | 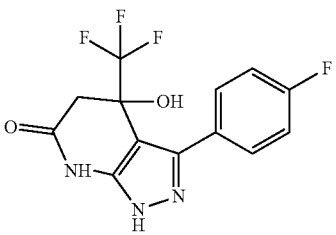 [SMILES: O=C1CC(O)(C(F)(F)F)c2c(-c3ccc(F)cc3)n[nH]c2N1] | 3-(4-Fluoro-phenyl)-4-hydroxy-4-trifluoromethyl-1,4,5,7-tetrahydro-pyrazolo[3,4-b]pyridin-6-one |
| 18 | 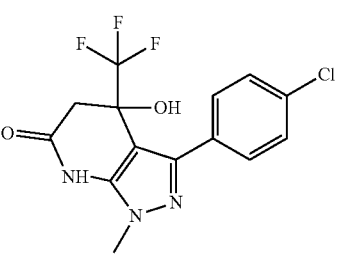 [SMILES: Cn1nc(-c2ccc(Cl)cc2)c2c1NC(=O)CC2(O)C(F)(F)F] | 3-(4-Chloro-phenyl)-4-hydroxy-1-methyl-4-trifluoromethyl-1,4,5,7-tetrahydro-pyrazolo[3,4-b]pyridin-6-one |
| 20 | 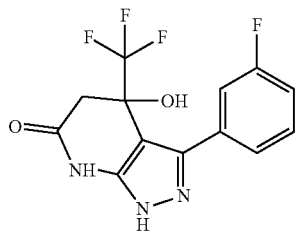 [SMILES: O=C1CC(O)(C(F)(F)F)c2c(-c3cccc(F)c3)n[nH]c2N1] | (−)-3-(3-Fluoro-phenyl)-4-hydroxy-4-trifluoromethyl-1,4,5,7-tetrahydro-pyrazolo[3,4-b]pyridin-6-one |
| 21 | 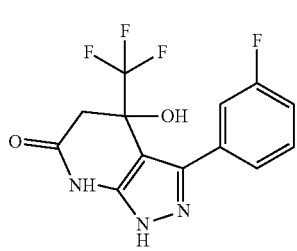 [SMILES: O=C1CC(O)(C(F)(F)F)c2c(-c3cccc(F)c3)n[nH]c2N1] | (+)-3-(3-Fluoro-phenyl)-4-hydroxy-4-trifluoromethyl-1,4,5,7-tetrahydro-pyrazolo[3,4-b]pyridin-6-one |
| 22 | 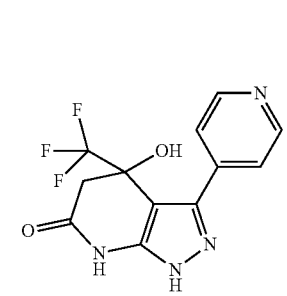 [SMILES: O=C1CC(O)(C(F)(F)F)c2c(-c3ccncc3)n[nH]c2N1] | 4-Hydroxy-3-pyridin-4-yl-4-trifluoromethyl-1,4,5,7-tetrahydro-pyrazolo[3,4-b]pyridin-6-one |
| 23 | 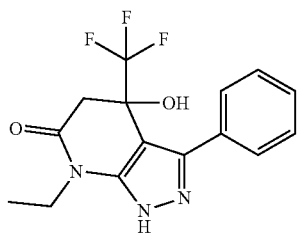 [SMILES: CCN1C(=O)CC(O)(C(F)(F)F)c2c(-c3ccccc3)n[nH]c21] | 4-Hydroxy-7-ethyl-3-phenyl-4-trifluoromethyl-1,4,5,7-tetrahydro-pyrazolo[3,4-b]pyridin-6-one |
| 24 | 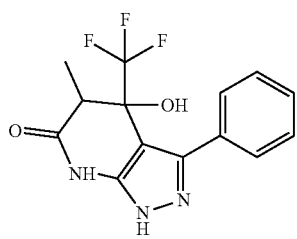 [SMILES: CC1C(=O)Nc2[nH]nc(-c3ccccc3)c2C1(O)C(F)(F)F] | 4-Hydroxy-5-methyl-3-phenyl-4-trifluoromethyl-1,4,5,7-tetrahydro-pyrazolo[3,4-b]pyridin-6-one |
| 25 | 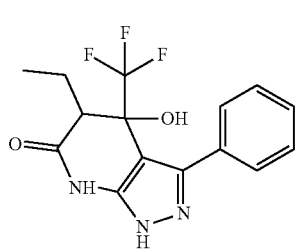 [SMILES: CCC1C(=O)Nc2[nH]nc(-c3ccccc3)c2C1(O)C(F)(F)F] | 4-Hydroxy-5-ethyl-3-phenyl-4-trifluoromethyl-1,4,5,7-tetrahydro-pyrazolo[3,4-b]pyridin-6-one |

| | | |
|---|---|---|
| 26 | | 4-Hydroxy-5-(2-hydroxy-ethyl)-3-phenyl-4-trifluoromethyl-1,4,5,7-tetrahydro-pyrazolo[3,4-b]pyridin-6-one |
| 27 | | 4-Hydroxy-5-methoxy-3-phenyl-4-trifluoromethyl-1,4,5,7-tetrahydro-pyrazolo[3,4-b]pyridin-6-one |
| 28 | | 3-Benzyl-4-hydroxy-4-trifluoromethyl-1,4,5,7-tetrahydro-pyrazolo[3,4-b]pyridin-6-one |
| 29 | | 4-Hydroxy-3-(1H-indol-3-yl)-4-trifluoromethyl-1,4,5,7-tetrahydro-pyrazolo[3,4-b]pyridin-6-one |
| 30 | | 3-Furan-2-yl-4-hydroxy-4-trifluoromethyl-1,4,5,7-tetrahydro-pyrazolo[3,4-b]pyridin-6-one |
| 31 | | 3-(3,4-Dimethoxy-phenyl)-4-hydroxy-4-trifluoromethyl-1,4,5,7-tetrahydro-pyrazolo[3,4-b]pyridin-6-one |
| 32 | | 4-Hydroxy-3-(3-methoxy-phenyl)-4-trifluoromethyl-1,4,5,7-tetrahydro-pyrazolo[3,4-b]pyridin-6-one |
| 33 | | 3-(1,5-Dimethyl-1H-pyrazol-4-yl)-4-hydroxy-4-trifluoromethyl-1,4,5,7-tetrahydro-pyrazolo[3,4-b]pyridin-6-one | and the physiologically acceptable salts, tautomers and stereoisomers thereof, including mixtures thereof in all ratios.

12. A method according to claim 1, wherein $R_1$ is phenyl which is unsubstituted or substituted with one or more substituents selected from alkyl, cycloalkyl, cycloalkylalkyl, heterocyclyl, heterocyclylalkyl, aryl, arylalkyl, heteroaryl, heteroarylalkyl, halogen, —F, —Cl, —Br, —I, —CN, —CF$_3$, —N$_3$, —NH$_2$, —NHZ1, —NZ2Z3, —NO$_2$, —OH, —OCF$_3$, —SH, —O—SO$_3$H, —OP(O)(OH)$_2$, —CHO, —COOH, —C(O)NH$_2$, —SO$_3$H, —P(O)(OH)$_2$, —C(O)—Z4, —C(O)O—Z5, —C(O)NH—Z6, —C(O)NZ7Z8, —O—Z9, —O(—Z10—O)$_a$—H, —O(—Z11—O)$_b$—Z12, —OC(O)—Z13, —OC(O)—O—Z14, —OC(O)—NHZ15, —O—C(O)—NZ16Z17, —OP(O)(OZ18)(OZ19), —OSi(Z20)(Z21)(Z22), —OS(O$_2$)—Z23, —NHC(O)—NH$_2$, —NHC(O)—Z24, —NZ25C(O)—Z26, —NH—C(O)—O—Z27, —NH—C(O)—NH—Z28, —NH—C(O)—NZ29Z30, —NZ31—C(O)—O—Z32, —NZ33—C(O)—NH—Z34, —NZ35—C(O)—NZ36Z37, —NHS(O$_2$)—Z38, —NZ39S(O$_2$)—Z40, —S—Z41, —S(O)—Z42, —S(O$_2$)—Z43, —S(O$_2$)NH—Z44, —S(O$_2$)NZ45Z46, —S(O$_2$)O—Z47, —P(O)(OZ48)(OZ49), —Si(Z50)(Z51)(Z52), —C(NH)—NH$_2$, —C(NZ53)—NH$_2$, —C(NH)—NHZ54, —C(NH)—NZ55Z56, —C(NZ57)—NHZ58, —C(NZ59)—NZ60Z61, —NH—C(O)—NH—O—Z62, —NH—C(O)—NZ63—O—Z64, —NZ65—C(O)—NZ66—O—Z67, —N(—C(O)—NH—O—Z68)$_2$, —N(—C(O)—NZ69—O—Z70)$_2$, —N(—C(O)—NH—O—Z71)(—C(O)—NZ72—O—Z73), —C(S)—Z74, —C(S)—O—Z75, —C(S)—NH—Z76, —C(S)—NZ77Z78, —C(O)—NH—O—Z79, —C(O)—NZ80—O—Z81, —C(S)—NH—O—Z82, —C(S)—NZ83—O—Z84, —C(O)—NH—NH—Z85, —C(O)—NH—NZ86Z87, —C(O)—NZ88—NZ89Z90, —C(S)—NH—NH—Z91, —C(S)—NH—NZ92Z93, —C(S)—NZ94—NZ95Z96, —C(O)—C(O)—O—Z97, —C(O)—C(O)—NH$_2$, —C(O)—C(O)—NHZ98, —C(O)—C(O)—NZ99Z100, —C(S)—C(O)—O—Z101, —C(O)—C(S)—O—Z102, —C(S)—C(S)—O—Z103, —C(S)—C(O)—NH$_2$, —C(S)—C(O)—NHZ104, —C(S)—C(O)—NZ105Z106, —C(S)—C(S)—NH$_2$, —C(S)—C(S)—NHZ107, —C(S)—C(S)—NZ108Z109, —C(O)—C(S)—NH$_2$, —C(O)—C(S)—NHZ110, —C(O)—C(S)—NZ111Z112;

Z1, Z2, Z3, Z4, Z5, Z6, Z7, Z8, Z9, Z10, Z11, Z12, Z13, Z14, Z15, Z16, Z17, Z18, Z19, Z20, Z21, Z22, Z23, Z24, Z25, Z26, Z27, Z28, Z29, Z30, Z31, Z32, Z33, Z34, Z35, Z36, Z37, Z38, Z39, Z40, Z41, Z42, Z43, Z44, Z45, Z46, Z47, Z48, Z49, Z50, Z51, Z52, Z53, Z54, Z55, Z56, Z57, Z58, Z59, Z60, Z61, Z62, Z63, Z64, Z65, Z66, Z67, Z68, Z69, Z70, Z71, Z72, Z73, Z74, Z75, Z76, Z77, Z78, Z79, Z80, Z81, Z82, Z83, Z84, Z85, Z86, Z87, Z88, Z89, Z90, Z91, Z92, Z93, Z94, Z95, Z96, Z97, Z98, Z99, Z100, Z101, Z102, Z103, Z104, Z105, Z106, Z107, Z108, Z109, Z110, Z111, Z112 are each, independently from each other, selected from alkyl, cycloalkyl, cycloalkylalkyl, heterocyclyl, heterocyclylalkyl, aryl, arylalkyl, heteroaryl, and heteroarylalkyl, and wherein alternatively Z7, Z8 and/or Z16, Z17 and/or Z29, Z30 and/or Z36, Z37 and/or Z45, Z46 and/or Z55, Z56 and/or Z60, Z61 and/or Z77, Z78 and/or Z86, Z87 and/or Z89, Z90 and/or Z92, Z93 and/or Z95, Z96 and/or Z99, Z100 and/or Z105, Z106 and/or Z108, Z109 and/or Z111, Z112 can each, respectively, together form a heterocyclyl.

13. A method according to claim 1, wherein $R_1$ is a cycloalkyl selected from cyclopropyl, cyclobutyl, cyclopentyl, cyclohexyl, cycloheptyl, cyclooctyl, cyclodecyl, cyclohexenyl, cyclopentenyl and cyclooctadienyl, which in each case is unsubstituted or substituted as defined in claim 1.

14. A method according to claim 1, wherein $R_1$ is a heterocyclyl selected from pyrrolidinyl, thiapyrrolidinyl, piperidinyl, piperazinyl, oxapiperazinyl, oxapiperidinyl, oxadiazolyl, tetrahydrofuryl, imidazolidinyl, thiazolidinyl, tetrahydropyranyl, morpholinyl, tetrahydrothiophenyl, dihydropyranyl, indolinyl, indolinylmethyl, imidazolidinyl, or 2-aza-bicyclo[2.2.2]octanyl, which in each case is unsubstituted or substituted as defined in claim 1.

15. A method according to claim 1, wherein $R_1$ is an aryl selected from phenyl, biphenyl, naphthyl, 1-naphthyl, 2-naphthyl, anthracenyl, indanyl, indenyl, and 1,2,3,4-tetrahydronaphthyl, which in each case is unsubstituted or substituted as defined in claim 1.

16. A method according to claim 1, wherein $R_1$ is a heteroaryl selected from acridinyl, benzdioxinyl, benzimidazolyl, benzisoxazolyl, benzodioxolyl, benzofuranyl, benzothiadiazolyl, benzothiazolyl, benzothienyl, benzoxazolyl, carbazolyl, cinnolinyl, dibenzofuranyl, dihydrobenzothienyl, furanyl, furazanyl, furyl, imidazolyl, indazolyl, indolinyl, indolizinyl, indolyl, isobenzylfuranyl, isoindolyl, isoquinolinyl, isoquinolyl, isothiazolyl, isoxazolyl, naphthyridinyl, oxadiazolyl, oxazolyl, phenazinyl, phenothiazinyl, phenoxazinyl, phthalazinyl, pteridinyl, purinyl, pyrazinyl, pyrazolyl, pyridazinyl, pyridinyl, pyridyl, pyrimidinyl, pyrimidyl, pyrrolyl, quinazolinyl, quinolinyl, quinolyl, quinoxalinyl, tetrazolyl, thiadiazolyl, thiazolyl, thienyl, thiophenyl, triazinyl, and triazolyl, which in each case is unsubstituted or substituted as defined in claim 1.

17. A method according to claim 1, wherein $R_1$ is:
(a) a cycloalkyl selected from cyclopropyl, cyclobutyl, cyclopentyl, cyclohexyl, cycloheptyl, cyclooctyl, cyclodecyl, cyclohexenyl, cyclopentenyl and cyclooctadienyl, which in each case is unsubstituted or substituted as defined in claim 1,
(b) a heterocyclyl selected from pyrrolidinyl, thiapyrrolidinyl, piperidinyl, piperazinyl, oxapiperazinyl, oxapiperidinyl, oxadiazolyl, tetrahydrofuryl, imidazolidinyl, thiazolidinyl, tetrahydropyranyl, morpholinyl, tetrahydrothiophenyl, dihydropyranyl, indolinyl, indolinylmethyl, imidazolidinyl, or 2-aza-bicyclo[2.2.2]octanyl, which in each case is unsubstituted or substituted as defined in claim 1,
(c) an aryl selected from phenyl, biphenyl, naphthyl, 1-naphthyl, 2-naphthyl, anthracenyl, indanyl, indenyl, and 1,2,3,4-tetrahydronaphthyl, which in each case is unsubstituted or substituted as defined in claim 1, or
(d) a heteroaryl selected from acridinyl, benzdioxinyl, benzimidazolyl, benzisoxazolyl, benzodioxolyl, benzofuranyl, benzothiadiazolyl, benzothiazolyl, benzothienyl, benzoxazolyl, carbazolyl, cinnolinyl, dibenzofuranyl, dihydrobenzothienyl, furanyl, furazanyl, furyl, imidazolyl, indazolyl, indolinyl, indolizinyl, indolyl, isobenzylfuranyl, isoindolyl, isoquinolinyl, isoquinolyl, isothiazolyl, isoxazolyl, naphthyridinyl, oxadiazolyl, oxazolyl, phenazinyl, phenothiazinyl, phenoxazinyl, phthalazinyl, pteridinyl, purinyl, pyrazinyl, pyrazolyl, pyridazinyl, pyridinyl, pyridyl, pyrimidinyl, pyrimidyl, pyrrolyl, quinazolinyl, quinolinyl, quinolyl, quinoxalinyl, tetrazolyl, thiadiazolyl, thiazolyl, thienyl, thiophenyl, triazinyl, and triazolyl, which in each case is unsubstituted or substituted as defined in claim 1.

\* \* \* \* \*